United States Patent [19]
Lewis et al.

[11] Patent Number: 5,989,894
[45] Date of Patent: Nov. 23, 1999

[54] ISOLATED DNA CODING FOR SPIDER SILK PROTEIN, A REPLICABLE VECTOR AND A TRANSFORMED CELL CONTAINING THE DNA

[75] Inventors: Randolph V. Lewis, Laramie, Wyo.; Ming Xu, Calgary, Canada; Michael B. Hinman, Laramie, Wyo.

[73] Assignee: University of Wyoming, Laramie, Wyo.

[21] Appl. No.: 08/317,844

[22] Filed: Oct. 4, 1994

Related U.S. Application Data

[63] Continuation of application No. 07/684,819, Apr. 15, 1991, abandoned, which is a continuation-in-part of application No. 07/511,792, Apr. 20, 1990, abandoned.

[51] Int. Cl.[6] .............................. C12N 1/21; C12N 15/63; C07H 21/04
[52] U.S. Cl. .................. 435/252.3; 435/252.33; 435/320.1; 536/23.5
[58] Field of Search .................... 530/353; 536/23.5; 435/320.1, 69.1, 252.3, 252.33

[56] References Cited

U.S. PATENT DOCUMENTS

| | | | |
|---|---|---|---|
| 4,394,443 | 7/1983 | Weissman et al. | 435/6 |
| 4,727,028 | 2/1988 | Santerre et al. | 435/240.2 |
| 5,171,505 | 12/1992 | Lock | 264/202 |
| 5,245,012 | 9/1993 | Lombardi et al. | 530/353 |

FOREIGN PATENT DOCUMENTS

| | | |
|---|---|---|
| 0294979 | 12/1988 | European Pat. Off. . |
| 2162190 | 1/1986 | United Kingdom . |
| 2205568 | 12/1988 | United Kingdom . |
| 9116351 | 10/1991 | WIPO . |
| WO91/16351 | 10/1991 | WIPO . |

OTHER PUBLICATIONS

Candelas et al. 1981. J. Exp. Zool. 216: 1–6.
Yuen et al. Jan. 1989. Bio Techniques 7(1): 74–82.
Ish–Horowicz et al. 1981. Nucleic Acids Research 9(13): 2989–2998.
Lewis, R.V. 1989. "Cloning and Structure of Different Types of Spider Silk", NTIS Document No. AD–A216217.
Raju et al. 1987. J. Biol. Chem. 262(12): 5755–5762.
Chemical & Engineering News, pp. 24–25, (Jul. 25, 1988).
Randolph V. Lewis, "Cloning and Structure of Different Types of Spider Silk", NTIS Document No. AD–A203 137 (1988).
Nina Hall, New Scientist, p. 39, "Designs on silk weave stronger fibres", Sep. 29, 1988.
F. Lucas, "Spiders and their silks", pp. 20–26 (Jan. 1964).
Work, Textile Research Journal, pp. 650–662 (Oct. 1977).
Work, J. Arachnol., 9:299–308 (1981).
Work, Textile Research Journal, pp. 349–356 (May 1982).
Work et al, J. Arachnol., 10:1–10 (1982).
Xu et al, Proc. Natl. Acad. Sci. USA, vol. 87, pp. 7120–7124 (1990).
Dong et al, Archives of Biochemistry and Biophysics, vol. 284, No. 1, pp. 53–57 (1991).
Chemical Abstracts, (1991) vol. 114, p. 182.
Chemical Abstracts, (1989), vol. 111, p. 182.
Dissertation Abstracts Int'l, (1991), vol. 52, No. 2, p. 669–B.
Lombardi et al, (1990), Acta Zool, Fennica 190:243–248.
American Chemical Society, (1990),Polymer Preprints, vol. 31, No. 1.

*Primary Examiner*—Robert A. Wax
*Assistant Examiner*—Kawai Lau
*Attorney, Agent, or Firm*—Birch, Stewart, Kolasch and Birch, LLP

[57] ABSTRACT

The present invention is directed to isolated cDNA which codes for spider silk protein or a fragment or variant thereof, a replicable vector containing cDNA which codes for spider silk protein and which is capable of expressing spider silk protein, a transformed cell or microorganism containing cDNA which codes for spider silk protein or a fragment thereof which is capable of expressing spider silk protein and products, such as fibers, which may be manufactured utilizing the recombinant protein of the present invention.

20 Claims, 20 Drawing Sheets

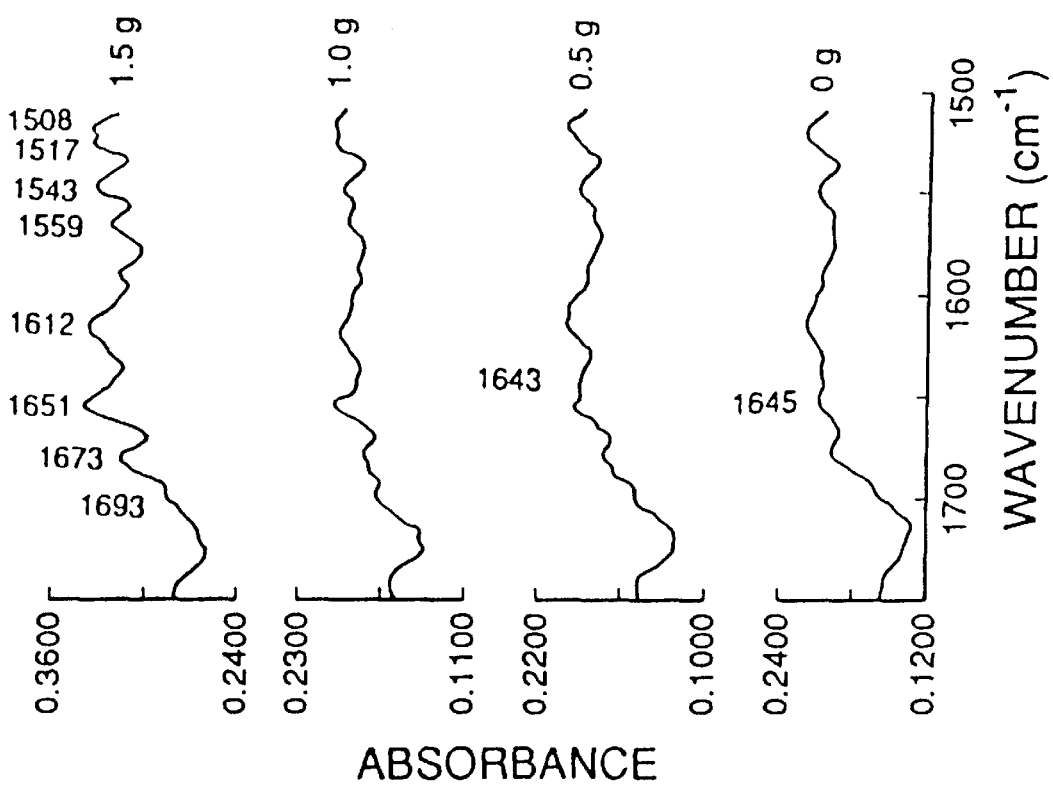
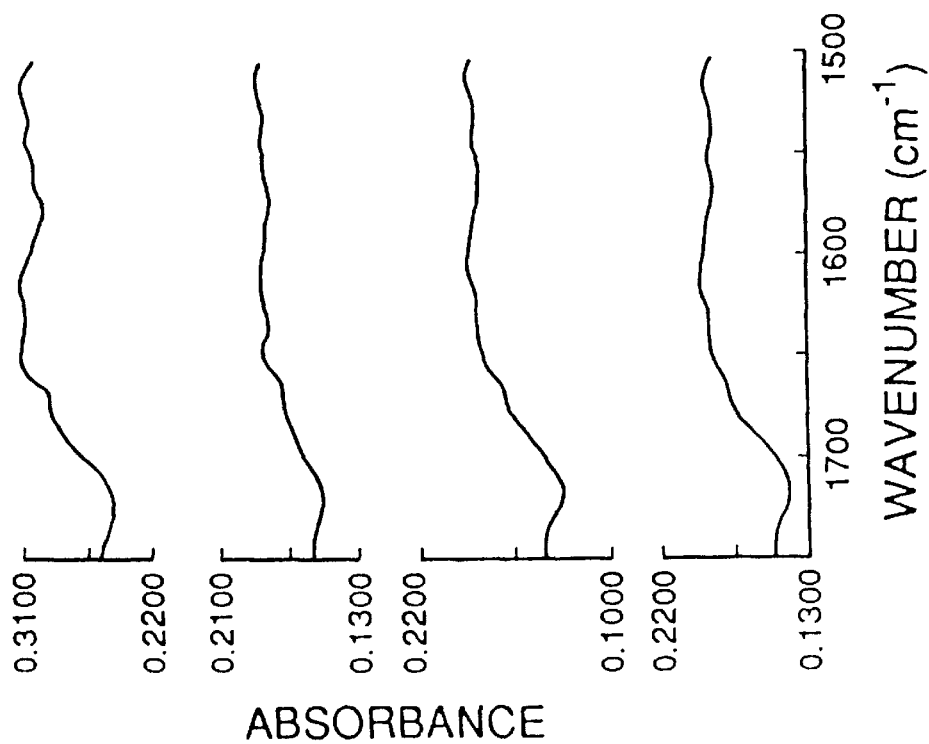

```
CAA GGG GCA GGT GCA GCA GCA GCA GCT GGA GGT GCC GGA CAA GGA          48
Gln Gly Ala Gly Ala Ala Ala Ala Ala Gly Gly Ala Gly Gln Gly
 1           5               10              15

GGA TAT GGA GGT CTT GGT GGA CAA GGA GCT GGT CAA GGT GGA TAT GGA      96
Gly Tyr Gly Gly Leu Gly Gly Gln Gly Ala Gly Gln Gly Gly Tyr Gly
             20              25              30

GGT CTT GGT GGA CAA GGT GCC GGA CAA GGA GCT GGT GCA GCC GCC GCA     144
Gly Leu Gly Gly Gln Gly Ala Gly Gln Gly Ala Gly Ala Ala Ala Ala
         35              40              45

GCA GCA GCT GGT GGT GCC GGA CAA GGA GGA TAT GGA GGT CTT GGA AGC     192
Ala Ala Ala Gly Gly Ala Gly Gln Gly Gly Tyr Gly Gly Leu Gly Ser
     50              55              60

CAA GGT GCT GGA CGA GGT GGA CAA GGA GCT GGA GCA GCC GCT GCA GCT     240
Gln Gly Ala Gly Arg Gly Gly Gln Gly Ala Gly Ala Ala Ala Ala Ala
65              70              75              80

GCG GGT GGT GCC GGA CAA GGA GGT TAT GGA GGT CTT GGA AGT CAA GGT     288
Ala Gly Gly Ala Gly Gln Gly Gly Tyr Gly Gly Leu Gly Ser Gln Gly
             85              90              95

GCA GGA CGA GGT GGA TTA GGT GGA CAA GGG GCA GGT GCA GCA GCC GCT     336
Ala Gly Arg Gly Gly Leu Gly Gly Gln Gly Ala Gly Ala Ala Ala Ala
         100             105             110

GCA GCA GCT GGA GGT GCC GGA CAA GGA GGA TAT GGA GGC CTT GGA AAC     384
Ala Ala Ala Gly Gly Ala Gly Gln Gly Gly Tyr Gly Gly Leu Gly Asn
     115             120             125

CAA GGT GCT GGA CGA GGT GGA CAA GGT GCA GCA GCA GCA GCA GCT GGA     432
Gln Gly Ala Gly Arg Gly Gly Gln Gly Ala Ala Ala Ala Ala Ala Gly
130             135             140

GGT GCT GGA CAA GGA GGA TAT GGA GGT CTT GGA AGC CAA GGT GCA GGA     480
Gly Ala Gly Gln Gly Gly Tyr Gly Gly Leu Gly Ser Gln Gly Ala Gly
145             150             155             160

CGA GGT GGA TTA GGT GGA CAA GGT GCA GGT GCA GCA GCA GCA GCA GCC     528
Arg Gly Gly Leu Gly Gly Gln Gly Ala Gly Ala Ala Ala Ala Ala Ala
             165             170             175

GGA GGT GCT GGA CAA GGC GGA TAC GGT GGT CTT GGT GGA CAA GGT GCC     576
Gly Gly Ala Gly Gln Gly Gly Tyr Gly Gly Leu Gly Gly Gln Gly Ala
         180             185             190

GGA CAA GGA GGC TAT GGA GGA CTT GGA AGC CAA GGT GCT GGA CGA GGA     624
Gly Gln Gly Gly Tyr Gly Gly Leu Gly Ser Gln Gly Ala Gly Arg Gly
     195             200             205
```

FIG. 6A

```
GGA TTA GGT GGA CAA GGT GCA GGT GCA GCA GCA GCA GCA GCA GCT GGA        672
Gly Leu Gly Gly Gln Gly Ala Gly Ala Ala Ala Ala Ala Ala Ala Gly
    210             215                 220

GGT GCC GGA CAA GGA GGA CTA GGT GGA CAA GGT GCT GGA CAA GGA GCT        720
Gly Ala Gly Gln Gly Gly Leu Gly Gly Gln Gly Ala Gly Gln Gly Ala
225             230                 235                 240

GGA GCA TCC GCT GCA GCA GCT GGT GGT GCC GGA CAA GGA GGA TAT GGA        768
Gly Ala Ser Ala Ala Ala Ala Gly Gly Ala Gly Gln Gly Gly Tyr Gly
                245                 250                 255

GGT CTT GGA AGC CAA GGT GCT GGA CGA GGT GGA GAA GGT GCA GGC GCA        816
Gly Leu Gly Ser Gln Gly Ala Gly Arg Gly Gly Glu Gly Ala Gly Ala
                260                 265                 270

GCC GCA GCA GCA GCC GGA GGT GCT GGA CAA GGA GGA TAC GGT GGT CTT        864
Ala Ala Ala Ala Ala Gly Gly Ala Gly Gln Gly Gly Tyr Gly Gly Leu
            275                 280                 285

GGT GGA CAA GGT GCC GGA CAA GGA GGC TAT GGA GGA CTT GGA AGC CAA        912
Gly Gly Gln Gly Ala Gly Gln Gly Gly Tyr Gly Gly Leu Gly Ser Gln
        290                 295                 300

GGT GCT GGA CGA GGA GGA TTA GGT GGA CAA GGT GCA GGT GCA GCA GCA        960
Gly Ala Gly Arg Gly Gly Leu Gly Gly Gln Gly Ala Gly Ala Ala Ala
305                 310                 315                 320

GCT GGA GGT GCC GGG CAA GGA GGA CTA GGT GGA CAA GGT GCT GGA CAA       1008
Ala Gly Gly Ala Gly Gln Gly Gly Leu Gly Gly Gln Gly Ala Gly Gln
                325                 330                 335

GGA GCT GGA GCA GCC GCT GCA GCA GCT GGT GGT GCC GGA CAA GGA GGA       1056
Gly Ala Gly Ala Ala Ala Ala Ala Ala Gly Gly Ala Gly Gln Gly Gly
                340                 345                 350

TAT GGA GGT CTT GGA AGC CAA GGT GCA GGA CGA GGT GGA TTA GGT GGA       1104
Tyr Gly Gly Leu Gly Ser Gln Gly Ala Gly Arg Gly Gly Leu Gly Gly
            355                 360                 365

CAA GGG GCA GGT GCA GTA GCC GCT GCA GCA GCT GGA GGT GCC GGA CAA       1152
Gln Gly Ala Gly Ala Val Ala Ala Ala Ala Gly Gly Ala Gly Gln
        370                 375                 380

GGA GGA TAT GGA GGT CTT GGA AGC CAA GGT GCT GGA CGA GGT GGA CAA       1200
Gly Gly Tyr Gly Gly Leu Gly Ser Gln Gly Ala Gly Arg Gly Gly Gln
385                 390                 395                 400

GGA GCT GGA GCA GCC GCT GCA GCA GCT GGT GGT GCC GGA CAA AGA GGT       1248
Gly Ala Gly Ala Ala Ala Ala Ala Ala Gly Gly Ala Gly Gln Arg Gly
                405                 410                 415
```

FIG. 6B

```
TAT GGA GGT CTT GGA AAT CAA GGT GCA GGA CGA GGT GGA TTA GGT GGA    1296
Tyr Gly Gly Leu Gly Asn Gln Gly Ala Gly Arg Gly Gly Leu Gly Gly
            420                 425                 430

CAA GGG GCA GGT GCA GCA GCC GCT GCA GCA GCT GGA GGT GCC GGA CAA    1344
Gln Gly Ala Gly Ala Ala Ala Ala Ala Ala Ala Gly Gly Ala Gly Gln
        435                 440                 445

GGA GGA TAT GGA GGC CTT GGA AAC CAA GGT GCT GGA CGA GGT GGA CAA    1392
Gly Gly Tyr Gly Gly Leu Gly Asn Gln Gly Ala Gly Arg Gly Gly Gln
        450                 455                 460

GGT GCA GCA GCA GCA GCT GGA GGT GCC GGA CAA GGA GGA TAT GGA GGT    1440
Gly Ala Ala Ala Ala Ala Gly Gly Ala Gly Gln Gly Gly Tyr Gly Gly
465                 470                 475                 480

CTT GGA AGC CAA GGT GCT GGA CGA GGT GGA CAA GGT GCA GGC GCA GCC    1488
Leu Gly Ser Gln Gly Ala Gly Arg Gly Gly Gln Gly Ala Gly Ala Ala
            485                 490                 495

GCA GCA GCA GCC GTA GGT GCT GGA CAA GAA GGA ATA CGT GGA CAA GGT    1536
Ala Ala Ala Ala Val Gly Ala Gly Gln Glu Gly Ile Arg Gly Gln Gly
            500                 505                 510

GCC GGA CAA GGA GGC TAT GGA GGA CTT GGA AGC CAA GGT TCT GGT CGA    1584
Ala Gly Gln Gly Gly Tyr Gly Gly Leu Gly Ser Gln Gly Ser Gly Arg
        515                 520                 525

GGA GGA TTA GGT GGA CAA GGT GCA GGT GCA GCA GCA GCA GCA GCT GGA    1632
Gly Gly Leu Gly Gly Gln Gly Ala Gly Ala Ala Ala Ala Ala Ala Gly
        530                 535                 540

GGT GCT GGA CAA GGA GGA TTA GGT GGA CAA GGT GCT GGA CAA GGA GCT    1680
Gly Ala Gly Gln Gly Gly Leu Gly Gly Gln Gly Ala Gly Gln Gly Ala
545                 550                 555                 560

GGA GCA GCC GCT GCA GCA GCT GGT GGT GTT AGA CAA GGA GGA TAT GGA    1728
Gly Ala Ala Ala Ala Ala Ala Gly Gly Val Arg Gln Gly Gly Tyr Gly
            565                 570                 575

GGT CTT GGA AGC CAA GGT GCT GGA CGA GGT GGA CAA GGT GCA GGC GCA    1776
Gly Leu Gly Ser Gln Gly Ala Gly Arg Gly Gly Gln Gly Ala Gly Ala
            580                 585                 590

GCC GCA GCA GCA GCC GGA GGT GCT GGA CAA GGA GGA TAT GGT GGT CTT    1824
Ala Ala Ala Ala Ala Gly Gly Ala Gly Gln Gly Gly Tyr Gly Gly Leu
        595                 600                 605

GGT GGA CAA GGT GTT GGC CGA GGT GGA TTA GGT GGA CAG GGT GCA GGC    1872
Gly Gly Gln Gly Val Gly Arg Gly Gly Leu Gly Gly Gln Gly Ala Gly
        610                 615                 620
```

FIG. 6C

```
GCA GCG GCA GCT GGT GGT GCT GGA CAA GGA GGA TAT GGT GGT GTT GGT    1920
Ala Ala Ala Ala Gly Gly Ala Gly Gln Gly Gly Tyr Gly Gly Val Gly
625             630                 635                 640

TCT GGG GCG TCT GCT GCC TCT GCA GCT GCA TCC CGG TTG TCT TCT CCT    1968
Ser Gly Ala Ser Ala Ala Ser Ala Ala Ala Ser Arg Leu Ser Ser Pro
                645             650                 655

CAA GCT AGT TCA AGA GTT TCA TCA GCT GTT TCC AAC TTG GTT GCA AGT    2016
Gln Ala Ser Ser Arg Val Ser Ser Ala Val Ser Asn Leu Val Ala Ser
            660             665                 670

GGT CCT ACT AAT TCT GCG GCC TTG TCA AGT ACA ATC AGT AAC GTG GTT    2064
Gly Pro Thr Asn Ser Ala Ala Leu Ser Ser Thr Ile Ser Asn Val Val
        675             680                 685

TCA CAA ATT GGC GCC AGC ATC CTG GTC TTT CTG GAT GTG ATG TCC TCA    2112
Ser Gln Ile Gly Ala Ser Ile Leu Val Phe Leu Asp Val Met Ser Ser
    690             695             700

TTC AAG CTC TTC TCG AGG TTG TTT CTG CTC TTA TCC AGA TCT TAG GTT    2160
Phe Lys Leu Phe Ser Arg Leu Phe Leu Leu Leu Ser Arg Ser End Val
705             710             715                 720

CTT CCA GCA TCG GCC AAG TTA ACT ATG GTT CCG CTG GAC AAG CCA CTC    2208
Leu Pro Ala Ser Ala Lys Leu Thr Met Val Pro Leu Asp Lys Pro Leu
                725             730                 735

AGA TCG TTG GTC AAT CAG TTT ATC AAG CCC TAG GTT AAA TGT AAA ATC    2256
Arg Ser Leu Val Asn Gln Phe Ile Lys Pro End Val Lys Cys Lys Ile
            740             745                 750

AAG AGT TGC TAA AAC TTA ATG AAC TCG GGC TGT TTA TTT GTG TTA GGT    2304
Lys Ser Cys End Asn Leu Met Asn Ser Gly Cys Leu Phe Val Leu Gly
        755             760                 765

TTT AAA ATA TTT TCA ATA AAT ATT ATG CAT ATA A                      2338
Phe Lys Ile Phe Ser Ile Asn Ile Met His Ile
    770             775
```

FIG. 6D

| | |
|---|---|
| CCT GGA GGA TAT GGA CCA GGA CAA CAA GGC CCA GGA GGA TAT GGC CCT<br>Pro Gly Gly Tyr Gly Pro Gly Gln Gln Gly Pro Gly Gly Tyr Gly Pro<br>1                          5                       10                   15 | 48 |
| GGA CAA CAA GGA CCA TCT GGA CCT GGC AGT GCC GCT GCA GCA GCA GCA<br>Gly Gln Gln Gly Pro Ser Gly Pro Gly Ser Ala Ala Ala Ala Ala Ala<br>                20                      25                       30 | 96 |
| GCC GCC GCA GCA GGA CCT GGA GGA TAT GGC CCT GGA CAA CAA GGA CCC<br>Ala Ala Ala Ala Gly Pro Gly Gly Tyr Gly Pro Gly Gln Gln Gly Pro<br>        35                      40                       45 | 144 |
| GGA GGA TAT GGA CCA GGA CAA CAA GGA CCC GGA AGA TAT GGA CCA GGA<br>Gly Gly Tyr Gly Pro Gly Gln Gln Gly Pro Gly Arg Tyr Gly Pro Gly<br>       50                     55                      60 | 192 |
| CAA CAA GGA CCA TCT GGA CCT GGC AGT GCC GCT GCA GCC GCA GCA GGA<br>Gln Gln Gly Pro Ser Gly Pro Gly Ser Ala Ala Ala Ala Ala Ala Gly<br>65                      70                      75                     80 | 240 |
| TCT GGA CAA CAA GGC CCA GGA GGA TAT GGA CCA CGT CAA CAA GGT CCA<br>Ser Gly Gln Gln Gly Pro Gly Gly Tyr Gly Pro Arg Gln Gln Gly Pro<br>                  85                      90                       95 | 288 |
| GGA GGT TAT GGA CAA GGA CAA CAA GGA CCA TCT GGA CCA GGC AGT GCA<br>Gly Gly Tyr Gly Gln Gly Gln Gln Gly Pro Ser Gly Pro Gly Ser Ala<br>        100                     105                     110 | 336 |
| GCC GCA GCC TCA GCC GCA GCC TCA GCA GAA TCT GGA CAA CAA GGC CCA<br>Ala Ala Ala Ser Ala Ala Ala Ser Ala Glu Ser Gly Gln Gln Gly Pro<br>        115                     120                     125 | 384 |
| GGA GGT TAT GGA CCA GGT CAA CAA GGC CCA GGA GGT TAT GGA CCA GGT<br>Gly Gly Tyr Gly Pro Gly Gln Gln Gly Pro Gly Gly Tyr Gly Pro Gly<br>        130                     135                     140 | 432 |
| CAA CAA GGT CCT GGA GGA TAT GGA CCA GGA CAA CAA GGA CCA TCT GGA<br>Gln Gln Gly Pro Gly Gly Tyr Gly Pro Gly Gln Gln Gly Pro Ser Gly<br>145                   150                     155                   160 | 480 |
| CCA GGT AGT GCC GCT GCA GCA GCC GCC GCC GCA TCA GGA CCT GGA CAA<br>Pro Gly Ser Ala Ala Ala Ala Ala Ala Ala Ala Ser Gly Pro Gly Gln<br>                165                     170                     175 | 528 |
| CAA GGA CCA GGA GGA TAT GGA CCA GGT CAA CAA GGT CCT GGA GGA TAT<br>Gln Gly Pro Gly Gly Tyr Gly Pro Gly Gln Gln Gly Pro Gly Gly Tyr<br>                  180                     185                     190 | 576 |

FIG. 7A

```
GGA CCA GGA CAA CAA GGA CCA TCT GGA CCA GGT AGT GCC GCT GCA GCC         624
Gly Pro Gly Gln Gln Gly Pro Ser Gly Pro Gly Ser Ala Ala Ala Ala
        195                 200                 205

GCC GCC GCC GCA TCA GGA CCT GGA CAA CAA GGA CCA GGA GGA TAT GGA         672
Ala Ala Ala Ala Ser Gly Pro Gly Gln Gln Gly Pro Gly Gly Tyr Gly
    210                 215                 220

CCA GGT CAA CAA GGT CCA GGA GGT TAT GGA CCA GGA CAA CAA GGA CTA         720
Pro Gly Gln Gln Gly Pro Gly Gly Tyr Gly Pro Gly Gln Gln Gly Leu
225                 230                 235                 240

TCT GGA CCA GGC AGT GCA GCT GCA GCA GCC GCA GCA GGA CCT GGA CAA         768
Ser Gly Pro Gly Ser Ala Ala Ala Ala Ala Ala Ala Gly Pro Gly Gln
                245                 250                 255

CAA GGA CCC GGA GGA TAT GGA CCA GGA CAA CAA GGA CCA TCT GGA CCC         816
Gln Gly Pro Gly Gly Tyr Gly Pro Gly Gln Gln Gly Pro Ser Gly Pro
            260                 265                 270

GGT AGT GCC GCT GCA GCA GCA GCC GCC GCA GCA GGA CCT GGA GGA TAT         864
Gly Ser Ala Ala Ala Ala Ala Ala Ala Ala Ala Gly Pro Gly Gly Tyr
        275                 280                 285

GGC CCT GGA CAA CAA GGA CCC GGA GGA TAT GGA CCA GGA CAA CAA GGA         912
Gly Pro Gly Gln Gln Gly Pro Gly Gly Tyr Gly Pro Gly Gln Gln Gly
    290                 295                 300

CCA TCT GGA GCA GGC AGT GCA GCA GCA GCA GCC GCA GCA GGA CCT GGA         960
Pro Ser Gly Ala Gly Ser Ala Ala Ala Ala Ala Ala Ala Gly Pro Gly
305                 310                 315                 320

CAA CAA GGA TTA GGA GGT TAT GGA CCA GGA CAA CAA GGT CCA GGA GGA        1008
Gln Gln Gly Leu Gly Gly Tyr Gly Pro Gly Gln Gln Gly Pro Gly Gly
                325                 330                 335

TAT GGA CCA GGA CAA CAA GGT CCA GGA GGA TAT GGA CCA GGT AGT GCA        1056
Tyr Gly Pro Gly Gln Gln Gly Pro Gly Gly Tyr Gly Pro Gly Ser Ala
            340                 345                 350

TCT GCA GCA GCA GCC GCA GCA GGA CCT GGA CAA CAA GGA CCA GGA GGA        1104
Ser Ala Ala Ala Ala Ala Ala Gly Pro Gly Gln Gln Gly Pro Gly Gly
        355                 360                 365

TAT GGA CCT GGA CAA CAA GGA CCA TCT GGA CCA GGC AGT GCA TCT GCA        1152
Tyr Gly Pro Gly Gln Gln Gly Pro Ser Gly Pro Gly Ser Ala Ser Ala
    370                 375                 380

GCA GCA GCC GCA GCC GCA GCA GGA CCA GGA GGA TAT GGA CCA GGA CAA        1200
Ala Ala Ala Ala Ala Ala Ala Gly Pro Gly Gly Tyr Gly Pro Gly Gln
385                 390                 395                 400
```

FIG. 7B

```
CAA GGT CCA GGA GGA TAT GCA CCA GGA CAA CAA GGA CCA TCT GGA CCA      1248
Gln Gly Pro Gly Gly Tyr Ala Pro Gly Gln Gln Gly Pro Ser Gly Pro
            405                 410                 415

GGC AGT GCA TCT GCA GCA GCA GCC GCA GCC GCA GCA GGA CCA GGA GGA      1296
Gly Ser Ala Ser Ala Ala Ala Ala Ala Ala Ala Ala Gly Pro Gly Gly
            420                 425                 430

TAT GGA CCA GGA CAA CAA GGT CCA GGA GGA TAT GCA CCA GGA CAA CAA      1344
Tyr Gly Pro Gly Gln Gln Gly Pro Gly Gly Tyr Ala Pro Gly Gln Gln
            435                 440                 445

GGA CCA TCT GGA CCA GGC AGT GCA GCA GCA GCA GCA GCT GCC AGT GCA      1392
Gly Pro Ser Gly Pro Gly Ser Ala Ala Ala Ala Ala Ala Ala Ser Ala
    450                 455                 460

GGA CCT GGT GGA TAT GGA CCA GCG CAA CAG GGA CCA TCT GGT CCT GGA      1440
Gly Pro Gly Gly Tyr Gly Pro Ala Gln Gln Gly Pro Ser Gly Pro Gly
465             470                 475                 480

ATC GCA GCT TCA GCT GCT TCA GCA GGA CCT GGA GGT TAT GGA CCA GCA      1488
Ile Ala Ala Ser Ala Ala Ser Ala Gly Pro Gly Gly Tyr Gly Pro Ala
            485                 490                 495

CAA CAA GGA CCA GCT GGA TAT GGG CCT GGA AGC GCA GTA GCA GCC TCT      1536
Gln Gln Gly Pro Ala Gly Tyr Gly Pro Gly Ser Ala Val Ala Ala Ser
            500                 505                 510

GCC GGT GCA GGA TCT GCA GGT TAT GGG CCA GGT TCT CAA GCT TCC GCT      1584
Ala Gly Ala Gly Ser Ala Gly Tyr Gly Pro Gly Ser Gln Ala Ser Ala
            515                 520                 525

GCA GCT TCT CGT CTG GCT TCT CCA GAT TCA GGC GCT AGA GTT GCA TCA      1632
Ala Ala Ser Arg Leu Ala Ser Pro Asp Ser Gly Ala Arg Val Ala Ser
    530                 535                 540

GCT GTT TCT AAC TTG GTA TCC AGT GGC CCA ACT AGC TCT GCT GCC TTA      1680
Ala Val Ser Asn Leu Val Ser Ser Gly Pro Thr Ser Ser Ala Ala Leu
545                 550                 555                 560

TCA AGT GTT ATC AGT AAC GCT GTG TCT CAA ATT GGC GCA AGT AAT CCT      1728
Ser Ser Val Ile Ser Asn Ala Val Ser Gln Ile Gly Ala Ser Asn Pro
            565                 570                 575

GGT CTC TCT GGT TGC GAT GTC CTC ATT CAA GCT CTC TGG AAA TCG TTT      1776
Gly Leu Ser Gly Cys Asp Val Leu Ile Gln Ala Leu Trp Lys Ser Phe
            580                 585                 590

CTG CTT GTG TAA CCA TCC TTT CTT CAT CCA GCA TTG GTC AAG TTA ATT       1824
Leu Leu Val
        595

ATG GAG CGG CTT CTC AGT TCG CCC AAG TTG TCG GCC AAT CTG TTT TGA      1872
```

FIG. 7C

```
GTG CAT TTT AAT TGA AAA ATT TAT TAA AAT ATG CAT GGA TTT TCT AGC    1920

CTG GGC AAC TAA TTG CTC GTA CTA TGT AAT TTT TTT TTA AAT AAA TTC    1968

TTT GCA ACT TCT AAA AAA AAA AAA AAA                                1995
```

FIG. 7D

SEQUENCE LISTING

```
(1) GENERAL INFORMATION:

(iii) NUMBER OF SEQUENCES: 62

(2) INFORMATION FOR SEQ ID NO:1:

(i) SEQUENCE CHARACTERISTICS:
        (A) LENGTH: 2338 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Nephilia clavipes (ix) FEATURE:
        (A) NAME/KEY: CDS
        (B) LOCATION: 1..2154
        (D) OTHER INFORMATION: /product= "Nephila clavipes
            dragline silk protein"

(x) PUBLICATION INFORMATION:
        (A) AUTHORS: Xu, Ming
                 Lewis, Randolph V.
        (B) TITLE: Structure of a protein superfiber:  Spider
            drafline silk
        (C) JOURNAL: Proc. Natl. Acad. Sci. U.S.A.
```

(D) VOLUME: 87
(F) PAGES: 7120-7124
(G) DATE: Sept.-1990
(K) RELEVANT RESIDUES IN SEQ ID NO:1: FROM 1 TO 2338

(xi) SEQUENCE DESCRIPTION: SEQ ID NO:1:

```
CAA GGG GCA GGT GCA GCA GCA GCA GCT GGA GGT GCC GGA CAA GGA        48
Gln Gly Ala Gly Ala Ala Ala Ala Ala Gly Gly Ala Gly Gln Gly
 1               5                  10                  15

GGA TAT GGA GGT CTT GGT GGA CAA GGA GCT GGT CAA GGT GGA TAT GGA    96
Gly Tyr Gly Gly Leu Gly Gly Gln Gly Ala Gly Gln Gly Gly Tyr Gly
                20                  25                  30

GGT CTT GGT GGA CAA GGT GCC GGA CAA GGA GCT GGT GCA GCC GCC GCA   144
Gly Leu Gly Gly Gln Gly Ala Gly Gln Gly Ala Gly Ala Ala Ala Ala
             35                  40                  45

GCA GCA GCT GGT GGT GCC GGA CAA GGA GGA TAT GGA GGT CTT GGA AGC   192
Ala Ala Ala Gly Gly Ala Gly Gln Gly Gly Tyr Gly Gly Leu Gly Ser
 50                  55                  60

CAA GGT GCT GGA CGA GGT GGA CAA GGA GCT GGA GCA GCC GCT GCA GCT   240
Gln Gly Ala Gly Arg Gly Gly Gln Gly Ala Gly Ala Ala Ala Ala Ala
 65                  70                  75                  80

GCG GGT GGT GCC GGA CAA GGA GGT TAT GGA GGT CTT GGA AGT CAA GGT   288
Ala Gly Gly Ala Gly Gln Gly Gly Tyr Gly Gly Leu Gly Ser Gln Gly
                 85                  90                  95

GCA GGA CGA GGT GGA TTA GGT GGA CAA GGG GCA GGT GCA GCA GCC GCT   336
Ala Gly Arg Gly Gly Leu Gly Gly Gln Gly Ala Gly Ala Ala Ala Ala
                100                 105                 110

GCA GCA GCT GGA GGT GCC GGA CAA GGA GGA TAT GGA GGC CTT GGA AAC   384
Ala Ala Ala Gly Gly Ala Gly Gln Gly Gly Tyr Gly Gly Leu Gly Asn
             115                 120                 125

CAA GGT GCT GGA CGA GGT GGA CAA GGT GCA GCA GCA GCA GCA GCT GGA   432
Gln Gly Ala Gly Arg Gly Gly Gln Gly Ala Ala Ala Ala Ala Ala Gly
130                 135                 140

GGT GCT GGA CAA GGA GGA TAT GGA GGT CTT GGA AGC CAA GGT GCA GGA   480
Gly Ala Gly Gln Gly Gly Tyr Gly Gly Leu Gly Ser Gln Gly Ala Gly
145                 150                 155                 160

CGA GGT GGA TTA GGT GGA CAA GGT GCA GGT GCA GCA GCA GCA GCA GCC   528
Arg Gly Gly Leu Gly Gly Gln Gly Ala Gly Ala Ala Ala Ala Ala Ala
                165                 170                 175

GGA GGT GCT GGA CAA GGC GGA TAC GGT GGT CTT GGT GGA CAA GGT GCC   576
Gly Gly Ala Gly Gln Gly Gly Tyr Gly Gly Leu Gly Gly Gln Gly Ala
                180                 185                 190

GGA CAA GGA GGC TAT GGA GGA CTT GGA AGC CAA GGT GCT GGA CGA GGA   624
Gly Gln Gly Gly Tyr Gly Gly Leu Gly Ser Gln Gly Ala Gly Arg Gly
            195                 200                 205

GGA TTA GGT GGA CAA GGT GCA GGT GCA GCA GCA GCA GCA GCT GGA       672
Gly Leu Gly Gly Gln Gly Ala Gly Ala Ala Ala Ala Ala Ala Gly
        210                 215                 220

GGT GCC GGA CAA GGA GGA CTA GGT GGA CAA GGT GCT GGA CAA GGA GCT   720
Gly Ala Gly Gln Gly Gly Leu Gly Gly Gln Gly Ala Gly Gln Gly Ala
225                 230                 235                 240

GGA GCA TCC GCT GCA GCA GCT GGT GGT GCC GGA CAA GGA GGA TAT GGA   768
Gly Ala Ser Ala Ala Ala Ala Gly Gly Ala Gly Gln Gly Gly Tyr Gly
                245                 250                 255

GGT CTT GGA AGC CAA GGT GCT GGA CGA GGT GGA GAA GGT GCA GGC GCA   816
Gly Leu Gly Ser Gln Gly Ala Gly Arg Gly Gly Glu Gly Ala Gly Ala
            260                 265                 270

GCC GCA GCA GCC GGA GGT GCT GGA CAA GGA GGA TAC GGT GGT CTT       864
Ala Ala Ala Ala Gly Gly Ala Gly Gln Gly Gly Tyr Gly Gly Leu
        275                 280                 285

GGT GGA CAA GGT GCC GGA CAA GGA GGC TAT GGA GGA CTT GGA AGC CAA   912
```

-continued

| | | | | | | | | | | | | | |
|---|---|---|---|---|---|---|---|---|---|---|---|---|---|
| Gly | Gly | Gln | Gly | Ala | Gly | Gln | Gly | Gly | Tyr | Gly | Gly | Leu | Gly | Ser | Gln |
| | 290 | | | | 295 | | | | 300 | | | | |

```
GGT GCT GGA CGA GGA GGA TTA GGT GGA CAA GGT GCA GGT GCA GCA GCA       960
Gly Ala Gly Arg Gly Gly Leu Gly Gly Gln Gly Ala Gly Ala Ala Ala
305             310                 315                 320

GCT GGA GGT GCC GGG CAA GGA GGA CTA GGT GGA CAA GGT GCT GGA CAA       1008
Ala Gly Gly Ala Gly Gln Gly Gly Leu Gly Gly Gln Gly Ala Gly Gln
                325                 330                 335

GGA GCT GGA GCA GCC GCT GCA GCA GCT GGT GGT GCC GGA CAA GGA GGA       1056
Gly Ala Gly Ala Ala Ala Ala Ala Gly Gly Ala Gly Gln Gly Gly
            340                 345                 350

TAT GGA GGT CTT GGA AGC CAA GGT GCA GGA CGA GGT GGA TTA GGT GGA       1104
Tyr Gly Gly Leu Gly Ser Gln Gly Ala Gly Arg Gly Gly Leu Gly Gly
                355                 360                 365

CAA GGG GCA GGT GCA GTA GCC GCT GCA GCA GCT GGA GGT GCC GGA CAA       1152
Gln Gly Ala Gly Ala Val Ala Ala Ala Ala Gly Gly Ala Gly Gln
370                 375                 380

GGA GGA TAT GGA GGT CTT GGA AGC CAA GGT GCT GGA CGA GGT GGA CAA       1200
Gly Gly Tyr Gly Gly Leu Gly Ser Gln Gly Ala Gly Arg Gly Gly Gln
385                 390                 395                 400

GGA GCT GGA GCA GCC GCT GCA GCA GCT GGT GGT GCC GGA CAA AGA GGT       1248
Gly Ala Gly Ala Ala Ala Ala Ala Ala Gly Gly Ala Gly Gln Arg Gly
                405                 410                 415

TAT GGA GGT CTT GGA AAT CAA GGT GCA GGA CGA GGT GGA TTA GGT GGA       1296
Tyr Gly Gly Leu Gly Asn Gln Gly Ala Gly Arg Gly Gly Leu Gly Gly
                420                 425                 430

CAA GGG GCA GGT GCA GCA GCC GCT GCA GCA GCT GGA GGT GCC GGA CAA       1344
Gln Gly Ala Gly Ala Ala Ala Ala Ala Ala Gly Gly Ala Gly Gln
                435                 440                 445

GGA GGA TAT GGA GGC CTT GGA AAC CAA GGT GCT GGA CGA GGT GGA CAA       1392
Gly Gly Tyr Gly Gly Leu Gly Asn Gln Gly Ala Gly Arg Gly Gly Gln
450                 455                 460

GGT GCA GCA GCA GCA GCT GGA GGT GCC GGA CAA GGA GGA TAT GGA GGT       1440
Gly Ala Ala Ala Ala Ala Gly Gly Ala Gly Gln Gly Gly Tyr Gly Gly
465                 470                 475                 480

CTT GGA AGC CAA GGT GCT GGA CGA GGT GGA CAA GGT GCA GGC GCA GCC       1488
Leu Gly Ser Gln Gly Ala Gly Arg Gly Gly Gln Gly Ala Gly Ala Ala
                485                 490                 495

GCA GCA GCA GCC GTA GGT GCT GGA CAA GAA GGA ATA CGT GGA CAA GGT       1536
Ala Ala Ala Ala Val Gly Ala Gly Gln Glu Gly Ile Arg Gly Gln Gly
                500                 505                 510

GCC GGA CAA GGA GGC TAT GGA GGA CTT GGA AGC CAA GGT TCT GGT CGA       1584
Ala Gly Gln Gly Gly Tyr Gly Gly Leu Gly Ser Gln Gly Ser Gly Arg
                515                 520                 525

GGA GGA TTA GGT GGA CAA GGT GCA GGT GCA GCA GCA GCA GCA GCT GGA       1632
Gly Gly Leu Gly Gly Gln Gly Ala Gly Ala Ala Ala Ala Ala Ala Gly
                530                 535                 540

GGT GCT GGA CAA GGA GGA TTA GGT GGA CAA GGT GCT GGA CAA GGA GCT       1680
Gly Ala Gly Gln Gly Gly Leu Gly Gly Gln Gly Ala Gly Gln Gly Ala
545                 550                 555                 560

GGA GCA GCC GCT GCA GCA GCT GGT GGT GTT AGA CAA GGA GGA TAT GGA       1728
Gly Ala Ala Ala Ala Ala Ala Gly Gly Val Arg Gln Gly Gly Tyr Gly
                565                 570                 575

GGT CTT GGA AGC CAA GGT GCT GGA CGA GGT GGA CAA GGT GCA GGC GCA       1776
Gly Leu Gly Ser Gln Gly Ala Gly Arg Gly Gly Gln Gly Ala Gly Ala
                580                 585                 590

GCC GCA GCA GCA GCC GGA GGT GCT GGA CAA GGA GGA TAT GGT GGT CTT       1824
Ala Ala Ala Ala Ala Gly Gly Ala Gly Gln Gly Gly Tyr Gly Gly Leu
                595                 600                 605

GGT GGA CAA GGT GTT GGC CGA GGT GGA TTA GGT GGA CAG GGT GCA GGC       1872
```

```
                                                                        29                                                             30
                                                                                          -continued Gly Gly Gln Gly Val Gly Arg Gly Gly Leu Gly Gln Gly Ala Gly
        610                 615                 620

GCA GCG GCA GCT GGT GGT GCT GGA CAA GGA GGA TAT GGT GGT GTT GGT             1920
Ala Ala Ala Ala Gly Gly Ala Gly Gln Gly Gly Tyr Gly Gly Val Gly
625                 630                 635                 640

TCT GGG GCG TCT GCT GCC TCT GCA GCT GCA TCC CGG TTG TCT TCT CCT             1968
Ser Gly Ala Ser Ala Ala Ser Ala Ala Ala Ser Arg Leu Ser Ser Pro
                645                 650                 655

CAA GCT AGT TCA AGA GTT TCA TCA GCT GTT TCC AAC TTG GTT GCA AGT             2016
Gln Ala Ser Ser Arg Val Ser Ser Ala Val Ser Asn Leu Val Ala Ser
                660                 665                 670

GGT CCT ACT AAT TCT GCG GCC TTG TCA AGT ACA ATC AGT AAC GTG GTT             2064
Gly Pro Thr Asn Ser Ala Ala Leu Ser Ser Thr Ile Ser Asn Val Val
            675                 680                 685

TCA CAA ATT GGC GCC AGC ATC CTG GTC TTT CTG GAT GTG ATG TCC TCA             2112
Ser Gln Ile Gly Ala Ser Ile Leu Val Phe Leu Asp Val Met Ser Ser
            690                 695                 700

TTC AAG CTC TTC TCG AGG TTG TTT CTG CTC TTA TCC AGA TCT                     2154
Phe Lys Leu Phe Ser Arg Leu Phe Leu Leu Leu Ser Arg Ser
705                 710                 715

TAGGTTCTTC CAGCATCGGC CAAGTTAACT ATGGTTCCGC TGGACAAGCC ACTCAGATCG           2214

TTGGTCAATC AGTTTATCAA GCCCTAGGTT AAATGTAAAA TCAAGAGTTG CTAAAACTTA           2274

ATGAACTCGG GCTGTTTATT TGTGTTAGGT TTTAAAATAT TTTCAATAAA TATTATGCAT           2334

ATAA                                                                        2338

(2) INFORMATION FOR SEQ ID NO:2:

(i) SEQUENCE CHARACTERISTICS:
        (A) LENGTH: 718 amino acids
        (B) TYPE: amino acid
        (D) TOPOLOGY: linear (ii) MOLECULE TYPE: protein (xi) SEQUENCE DESCRIPTION: SEQ ID NO:2:

Gln Gly Ala Gly Ala Ala Ala Ala Ala Gly Gly Ala Gly Gln Gly
 1               5                  10                  15

Gly Tyr Gly Gly Leu Gly Gly Gln Gly Ala Gly Gln Gly Gly Tyr Gly
                20                  25                  30

Gly Leu Gly Gly Gln Gly Ala Gly Gln Gly Ala Gly Ala Ala Ala Ala
            35                  40                  45

Ala Ala Ala Gly Gly Ala Gly Gln Gly Gly Tyr Gly Gly Leu Gly Ser
        50                  55                  60

Gln Gly Ala Gly Arg Gly Gly Leu Gly Ala Gly Ala Ala Ala Ala
65                  70                  75                  80

Ala Gly Gly Ala Gly Gln Gly Gly Tyr Gly Gly Leu Gly Ser Gln Gly
                85                  90                  95

Ala Gly Arg Gly Gly Leu Gly Gly Gln Gly Ala Gly Ala Ala Ala Ala
            100                 105                 110

Ala Ala Ala Gly Gly Ala Gly Gln Gly Gly Tyr Gly Gly Leu Gly Asn
        115                 120                 125

Gln Gly Ala Gly Arg Gly Gly Gln Gly Ala Ala Ala Ala Ala Gly
    130                 135                 140

Gly Ala Gly Gln Gly Gly Tyr Gly Gly Leu Gly Ser Gln Gly Ala Gly
145                 150                 155                 160

Arg Gly Gly Leu Gly Gly Gln Gly Ala Gly Ala Ala Ala Ala Ala
                165                 170                 175
```

-continued

```
Gly Gly Ala Gly Gln Gly Gly Tyr Gly Gly Leu Gly Gly Gln Gly Ala
                180                 185                 190

Gly Gln Gly Gly Tyr Gly Gly Leu Gly Ser Gln Gly Ala Gly Arg Gly
            195                 200                 205

Gly Leu Gly Gly Gln Gly Ala Gly Ala Ala Ala Ala Ala Ala Ala Gly
        210                 215                 220

Gly Ala Gly Gln Gly Gly Leu Gly Gly Gln Gly Ala Gly Gln Gly Ala
225                 230                 235                 240

Gly Ala Ser Ala Ala Ala Gly Gly Ala Gly Gln Gly Gly Tyr Gly
                245                 250                 255

Gly Leu Gly Ser Gln Gly Ala Gly Arg Gly Gly Glu Gly Ala Gly Ala
            260                 265                 270

Ala Ala Ala Ala Ala Gly Gly Ala Gly Gln Gly Gly Tyr Gly Gly Leu
        275                 280                 285

Gly Gly Gln Gly Ala Gly Gln Gly Gly Tyr Gly Gly Leu Gly Ser Gln
    290                 295                 300

Gly Ala Gly Arg Gly Gly Leu Gly Gly Gln Gly Ala Gly Ala Ala Ala
305                 310                 315                 320

Ala Gly Gly Ala Gly Gln Gly Gly Leu Gly Gly Gln Gly Ala Gly Gln
                325                 330                 335

Gly Ala Gly Ala Ala Ala Ala Ala Gly Gly Ala Gly Gln Gly Gly
            340                 345                 350

Tyr Gly Gly Leu Gly Ser Gln Gly Ala Gly Arg Gly Gly Leu Gly Gly
        355                 360                 365

Gln Gly Ala Gly Ala Val Ala Ala Ala Ala Gly Gly Ala Gly Gln
    370                 375                 380

Gly Gly Tyr Gly Gly Leu Gly Ser Gln Gly Ala Gly Arg Gly Gly Gln
385                 390                 395                 400

Gly Ala Gly Ala Ala Ala Ala Ala Gly Gly Ala Gly Gln Arg Gly
                405                 410                 415

Tyr Gly Gly Leu Gly Asn Gln Gly Ala Gly Arg Gly Gly Leu Gly Gly
            420                 425                 430

Gln Gly Ala Gly Ala Ala Ala Ala Ala Gly Gly Ala Gly Gln
        435                 440                 445

Gly Gly Tyr Gly Gly Leu Gly Asn Gln Gly Ala Gly Arg Gly Gly Gln
450                 455                 460

Gly Ala Ala Ala Ala Gly Gly Ala Gly Gln Gly Gly Tyr Gly Gly
465                 470                 475                 480

Leu Gly Ser Gln Gly Ala Gly Arg Gly Gly Gln Gly Ala Gly Ala Ala
                485                 490                 495

Ala Ala Ala Ala Val Gly Ala Gly Gln Glu Gly Ile Arg Gly Gln Gly
            500                 505                 510

Ala Gly Gln Gly Gly Tyr Gly Gly Leu Gly Ser Gln Gly Ser Gly Arg
        515                 520                 525

Gly Gly Leu Gly Gly Gln Gly Ala Gly Ala Ala Ala Ala Ala Gly
    530                 535                 540

Gly Ala Gly Gln Gly Gly Leu Gly Gly Gln Gly Ala Gly Gln Gly Ala
545                 550                 555                 560

Gly Ala Ala Ala Ala Ala Gly Gly Val Arg Gln Gly Gly Tyr Gly
                565                 570                 575

Gly Leu Gly Ser Gln Gly Ala Gly Arg Gly Gly Gln Gly Ala Gly Ala
            580                 585                 590

Ala Ala Ala Ala Ala Gly Gly Ala Gly Gln Gly Gly Tyr Gly Gly Leu
        595                 600                 605
```

```
Gly Gly Gln Gly Val Gly Arg Gly Gly Leu Gly Gln Gly Ala Gly
    610             615             620

Ala Ala Ala Ala Gly Gly Ala Gly Gln Gly Gly Tyr Gly Gly Val Gly
625             630             635             640

Ser Gly Ala Ser Ala Ala Ser Ala Ala Ala Ser Arg Leu Ser Ser Pro
            645             650             655

Gln Ala Ser Ser Arg Val Ser Ser Ala Val Ser Asn Leu Val Ala Ser
            660             665             670

Gly Pro Thr Asn Ser Ala Ala Leu Ser Ser Thr Ile Ser Asn Val Val
            675             680             685

Ser Gln Ile Gly Ala Ser Ile Leu Val Phe Leu Asp Val Met Ser Ser
    690             695             700

Phe Lys Leu Phe Ser Arg Leu Phe Leu Leu Leu Ser Arg Ser
705             710             715
```

(2) INFORMATION FOR SEQ ID NO:3:

(i) SEQUENCE CHARACTERISTICS:
        (A) LENGTH: 1995 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vii) IMMEDIATE SOURCE:
        (B) CLONE: p6B (ix) FEATURE:
        (A) NAME/KEY: CDS
        (B) LOCATION: 1..1785

(xi) SEQUENCE DESCRIPTION: SEQ ID NO:3:

```
CCT GGA GGA TAT GGA CCA GGA CAA CAA GGC CCA GGA GGA TAT GGC CCT        48
Pro Gly Gly Tyr Gly Pro Gly Gln Gln Gly Pro Gly Gly Tyr Gly Pro
  1               5                  10                  15

GGA CAA CAA GGA CCA TCT GGA CCT GGC AGT GCC GCT GCA GCA GCA GCA        96
Gly Gln Gln Gly Pro Ser Gly Pro Gly Ser Ala Ala Ala Ala Ala Ala
             20                  25                  30

GCC GCC GCA GCA GGA CCT GGA GGA TAT GGC CCT GGA CAA CAA GGA CCC       144
Ala Ala Ala Ala Gly Pro Gly Gly Tyr Gly Pro Gly Gln Gln Gly Pro
         35                  40                  45

GGA GGA TAT GGA CCA GGA CAA CAA GGA CCC GGA AGA TAT GGA CCA GGA       192
Gly Gly Tyr Gly Pro Gly Gln Gln Gly Pro Gly Arg Tyr Gly Pro Gly
     50                  55                  60

CAA CAA GGA CCA TCT GGA CCT GGC AGT GCC GCT GCA GCC GCA GCA GGA       240
Gln Gln Gly Pro Ser Gly Pro Gly Ser Ala Ala Ala Ala Ala Ala Gly
 65                  70                  75                  80

TCT GGA CAA CAA GGC CCA GGA GGA TAT GGA CCA CGT CAA CAA GGT CCA       288
Ser Gly Gln Gln Gly Pro Gly Gly Tyr Gly Pro Arg Gln Gln Gly Pro
                 85                  90                  95

GGA GGT TAT GGA CAA GGA CAA CAA GGA CCA TCT GGA CCA GGC AGT GCA       336
Gly Gly Tyr Gly Gln Gly Gln Gln Gly Pro Ser Gly Pro Gly Ser Ala
            100                 105                 110

GCC GCA GCC TCA GCC GCA GCC TCA GCA GAA TCT GGA CAA CAA GGC CCA       384
Ala Ala Ala Ser Ala Ala Ala Ser Ala Glu Ser Gly Gln Gln Gly Pro
        115                 120                 125

GGA GGT TAT GGA CCA GGT CAA CAA GGC CCA GGA GGT TAT GGA CCA GGT       432
Gly Gly Tyr Gly Pro Gly Gln Gln Gly Pro Gly Gly Tyr Gly Pro Gly
    130                 135                 140
```

-continued

| | | | | | | | | | | | | | | | |
|---|---|---|---|---|---|---|---|---|---|---|---|---|---|---|---|
| CAA | CAA | GGT | CCT | GGA | GGA | TAT | GGA | CCA | GGA | CAA | CAA | GGA | CCA | TCT | GGA | 480 |
| Gln | Gln | Gly | Pro | Gly | Gly | Tyr | Gly | Pro | Gly | Gln | Gln | Gly | Pro | Ser | Gly |
| 145 | | | | | 150 | | | | | 155 | | | | | 160 |

| CCA | GGT | AGT | GCC | GCT | GCA | GCA | GCC | GCC | GCC | GCA | TCA | GGA | CCT | GGA | CAA | 528 |
|---|---|---|---|---|---|---|---|---|---|---|---|---|---|---|---|---|
| Pro | Gly | Ser | Ala | Ala | Ala | Ala | Ala | Ala | Ala | Ala | Ser | Gly | Pro | Gly | Gln |
| | | | | 165 | | | | | 170 | | | | | 175 | |

| CAA | GGA | CCA | GGA | GGA | TAT | GGA | CCA | GGT | CAA | CAA | GGT | CCT | GGA | GGA | TAT | 576 |
|---|---|---|---|---|---|---|---|---|---|---|---|---|---|---|---|---|
| Gln | Gly | Pro | Gly | Gly | Tyr | Gly | Pro | Gly | Gln | Gln | Gly | Pro | Gly | Gly | Tyr |
| | | | 180 | | | | | 185 | | | | | 190 | | |

| GGA | CCA | GGA | CAA | CAA | GGA | CCA | TCT | GGA | CCA | GGT | AGT | GCC | GCT | GCA | GCC | 624 |
|---|---|---|---|---|---|---|---|---|---|---|---|---|---|---|---|---|
| Gly | Pro | Gly | Gln | Gln | Gly | Pro | Ser | Gly | Pro | Gly | Ser | Ala | Ala | Ala | Ala |
| | | 195 | | | | | 200 | | | | | 205 | | | |

| GCC | GCC | GCC | GCA | TCA | GGA | CCT | GGA | CAA | CAA | GGA | CCA | GGA | GGA | TAT | GGA | 672 |
|---|---|---|---|---|---|---|---|---|---|---|---|---|---|---|---|---|
| Ala | Ala | Ala | Ala | Ser | Gly | Pro | Gly | Gln | Gln | Gly | Pro | Gly | Gly | Tyr | Gly |
| | 210 | | | | | 215 | | | | | 220 | | | | |

| CCA | GGT | CAA | CAA | GGT | CCA | GGA | GGT | TAT | GGA | CCA | GGA | CAA | CAA | GGA | CTA | 720 |
|---|---|---|---|---|---|---|---|---|---|---|---|---|---|---|---|---|
| Pro | Gly | Gln | Gln | Gly | Pro | Gly | Gly | Tyr | Gly | Pro | Gly | Gln | Gln | Gly | Leu |
| 225 | | | | | 230 | | | | | 235 | | | | | 240 |

| TCT | GGA | CCA | GGC | AGT | GCA | GCT | GCA | GCA | GCC | GCA | GCA | GGA | CCT | GGA | CAA | 768 |
|---|---|---|---|---|---|---|---|---|---|---|---|---|---|---|---|---|
| Ser | Gly | Pro | Gly | Ser | Ala | Ala | Ala | Ala | Ala | Ala | Ala | Gly | Pro | Gly | Gln |
| | | | | 245 | | | | | 250 | | | | | 255 | |

| CAA | GGA | CCC | GGA | GGA | TAT | GGA | CCA | GGA | CAA | CAA | GGA | CCA | TCT | GGA | CCC | 816 |
|---|---|---|---|---|---|---|---|---|---|---|---|---|---|---|---|---|
| Gln | Gly | Pro | Gly | Gly | Tyr | Gly | Pro | Gly | Gln | Gln | Gly | Pro | Ser | Gly | Pro |
| | | | 260 | | | | | 265 | | | | | 270 | | |

| GGT | AGT | GCC | GCT | GCA | GCA | GCA | GCC | GCC | GCA | GCA | GGA | CCT | GGA | GGA | TAT | 864 |
|---|---|---|---|---|---|---|---|---|---|---|---|---|---|---|---|---|
| Gly | Ser | Ala | Ala | Ala | Ala | Ala | Ala | Ala | Ala | Ala | Gly | Pro | Gly | Gly | Tyr |
| | | 275 | | | | | 280 | | | | | 285 | | | |

| GGC | CCT | GGA | CAA | CAA | GGA | CCC | GGA | GGA | TAT | GGA | CCA | GGA | CAA | CAA | GGA | 912 |
|---|---|---|---|---|---|---|---|---|---|---|---|---|---|---|---|---|
| Gly | Pro | Gly | Gln | Gln | Gly | Pro | Gly | Gly | Tyr | Gly | Pro | Gly | Gln | Gln | Gly |
| | | 290 | | | | | 295 | | | | | 300 | | | |

| CCA | TCT | GGA | GCA | GGC | AGT | GCA | GCA | GCA | GCA | GCC | GCA | GCA | GGA | CCT | GGA | 960 |
|---|---|---|---|---|---|---|---|---|---|---|---|---|---|---|---|---|
| Pro | Ser | Gly | Ala | Gly | Ser | Ala | Ala | Ala | Ala | Ala | Ala | Ala | Gly | Pro | Gly |
| 305 | | | | | 310 | | | | | 315 | | | | | 320 |

| CAA | CAA | GGA | TTA | GGA | GGT | TAT | GGA | CCA | GGA | CAA | CAA | GGT | CCA | GGA | GGA | 1008 |
|---|---|---|---|---|---|---|---|---|---|---|---|---|---|---|---|---|
| Gln | Gln | Gly | Leu | Gly | Gly | Tyr | Gly | Pro | Gly | Gln | Gln | Gly | Pro | Gly | Gly |
| | | | | 325 | | | | | 330 | | | | | 335 | |

| TAT | GGA | CCA | GGA | CAA | CAA | GGT | CCA | GGA | GGA | TAT | GGA | CCA | GGT | AGT | GCA | 1056 |
|---|---|---|---|---|---|---|---|---|---|---|---|---|---|---|---|---|
| Tyr | Gly | Pro | Gly | Gln | Gln | Gly | Pro | Gly | Gly | Tyr | Gly | Pro | Gly | Ser | Ala |
| | | | 340 | | | | | 345 | | | | | 350 | | |

| TCT | GCA | GCA | GCA | GCC | GCA | GCA | GGA | CCT | GGA | CAA | CAA | GGA | CCA | GGA | GGA | 1104 |
|---|---|---|---|---|---|---|---|---|---|---|---|---|---|---|---|---|
| Ser | Ala | Ala | Ala | Ala | Ala | Ala | Gly | Pro | Gly | Gln | Gln | Gly | Pro | Gly | Gly |
| | | 355 | | | | | 360 | | | | | 365 | | | |

| TAT | GGA | CCT | GGA | CAA | CAA | GGA | CCA | TCT | GGA | CCA | GGC | AGT | GCA | TCT | GCA | 1152 |
|---|---|---|---|---|---|---|---|---|---|---|---|---|---|---|---|---|
| Tyr | Gly | Pro | Gly | Gln | Gln | Gly | Pro | Ser | Gly | Pro | Gly | Ser | Ala | Ser | Ala |
| | | 370 | | | | | 375 | | | | | 380 | | | |

| GCA | GCA | GCC | GCA | GCC | GCA | GCA | GGA | CCA | GGA | GGA | TAT | GGA | CCA | GGA | CAA | 1200 |
|---|---|---|---|---|---|---|---|---|---|---|---|---|---|---|---|---|
| Ala | Ala | Ala | Ala | Ala | Ala | Ala | Gly | Pro | Gly | Gly | Tyr | Gly | Pro | Gly | Gln |
| 385 | | | | | 390 | | | | | 395 | | | | | 400 |

| CAA | GGT | CCA | GGA | GGA | TAT | GCA | CCA | GGA | CAA | CAA | GGA | CCA | TCT | GGA | CCA | 1248 |
|---|---|---|---|---|---|---|---|---|---|---|---|---|---|---|---|---|
| Gln | Gly | Pro | Gly | Gly | Tyr | Ala | Pro | Gly | Gln | Gln | Gly | Pro | Ser | Gly | Pro |
| | | | | 405 | | | | | 410 | | | | | 415 | |

| GGC | AGT | GCA | TCT | GCA | GCA | GCA | GCC | GCA | GCC | GCA | GCA | GGA | CCA | GGA | GGA | 1296 |
|---|---|---|---|---|---|---|---|---|---|---|---|---|---|---|---|---|
| Gly | Ser | Ala | Ser | Ala | Ala | Ala | Ala | Ala | Ala | Ala | Ala | Gly | Pro | Gly | Gly |
| | | | 420 | | | | | 425 | | | | | 430 | | |

| TAT | GGA | CCA | GGA | CAA | CAA | GGT | CCA | GGA | GGA | TAT | GCA | CCA | GGA | CAA | CAA | 1344 |
|---|---|---|---|---|---|---|---|---|---|---|---|---|---|---|---|---|
| Tyr | Gly | Pro | Gly | Gln | Gln | Gly | Pro | Gly | Gly | Tyr | Ala | Pro | Gly | Gln | Gln |
| | | | 435 | | | | | 440 | | | | | 445 | | |

| GGA | CCA | TCT | GGA | CCA | GGC | AGT | GCA | GCA | GCA | GCA | GCA | GCT | GCC | AGT | GCA | 1392 |
|---|---|---|---|---|---|---|---|---|---|---|---|---|---|---|---|---|
| Gly | Pro | Ser | Gly | Pro | Gly | Ser | Ala | Ala | Ala | Ala | Ala | Ala | Ala | Ser | Ala |
| | | 450 | | | | | 455 | | | | | 460 | | | |

-continued

```
GGA CCT GGT GGA TAT GGA CCA GCG CAA CAG GGA CCA TCT GGT CCT GGA      1440
Gly Pro Gly Gly Tyr Gly Pro Ala Gln Gln Gly Pro Ser Gly Pro Gly
465                 470                 475                 480

ATC GCA GCT TCA GCT GCT TCA GCA GGA CCT GGA GGT TAT GGA CCA GCA      1488
Ile Ala Ala Ser Ala Ala Ser Ala Gly Pro Gly Gly Tyr Gly Pro Ala
                    485                 490                 495

CAA CAA GGA CCA GCT GGA TAT GGG CCT GGA AGC GCA GTA GCA GCC TCT      1536
Gln Gln Gly Pro Ala Gly Tyr Gly Pro Gly Ser Ala Val Ala Ala Ser
                500                 505                 510

GCC GGT GCA GGA TCT GCA GGT TAT GGG CCA GGT TCT CAA GCT TCC GCT      1584
Ala Gly Ala Gly Ser Ala Gly Tyr Gly Pro Gly Ser Gln Ala Ser Ala
            515                 520                 525

GCA GCT TCT CGT CTG GCT TCT CCA GAT TCA GGC GCT AGA GTT GCA TCA      1632
Ala Ala Ser Arg Leu Ala Ser Pro Asp Ser Gly Ala Arg Val Ala Ser
        530                 535                 540

GCT GTT TCT AAC TTG GTA TCC AGT GGC CCA ACT AGC TCT GCT GCC TTA      1680
Ala Val Ser Asn Leu Val Ser Ser Gly Pro Thr Ser Ser Ala Ala Leu
545                 550                 555                 560

TCA AGT GTT ATC AGT AAC GCT GTG TCT CAA ATT GGC GCA AGT AAT CCT      1728
Ser Ser Val Ile Ser Asn Ala Val Ser Gln Ile Gly Ala Ser Asn Pro
                    565                 570                 575

GGT CTC TCT GGT TGC GAT GTC CTC ATT CAA GCT CTC TGG AAA TCG TTT      1776
Gly Leu Ser Gly Cys Asp Val Leu Ile Gln Ala Leu Trp Lys Ser Phe
                580                 585                 590

CTG CTT GTG TAA CCA TCC TTT CTT CAT CCA GCA TTG GTC AAG TTA ATT      1824
Leu Leu Val
            595

ATG GAG CGG CTT CTC AGT TCG CCC AAG TTG TCG GCC AAT CTG TTT TGA      1872

GTG CAT TTT AAT TGA AAA ATT TAT TAA AAT ATG CAT GGA TTT TCT AGC      1920

CTG GGC AAC TAA TTG CTC GTA CTA TGT AAT TTT TTT TTA AAT AAA TTC      1968

TTT GCA ACT TCT AAA AAA AAA AAA AAA                                  1995
```

(2) INFORMATION FOR SEQ ID NO:4:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:4:

```
Pro Gly Gly Tyr Gly Pro Gly Gln Gln Gly Pro Gly Gly Tyr Gly Pro
1               5                   10                  15

Gly Gln Gln Gly Pro Ser Gly Pro Gly Ser Ala Ala Ala Ala Ala Ala
                20                  25                  30

Ala Ala Ala Ala Gly Pro Gly Gly Tyr Gly Pro Gly Gln Gln Gly Pro
            35                  40                  45

Gly Gly Tyr Gly Pro Gly Gln Gln Gly Pro Gly Arg Tyr Gly Pro Gly
        50                  55                  60

Gln Gln Gly Pro Ser Gly Pro Gly Ser Ala Ala Ala Ala Ala Ala Gly
65                  70                  75                  80

Ser Gly Gln Gln Gly Pro Gly Gly Tyr Gly Pro Arg Gln Gln Gly Pro
                85                  90                  95

Gly Gly Tyr Gly Gln Gly Gln Gln Gly Pro Ser Gly Pro Gly Ser Ala
                    100                 105                 110

Ala Ala Ala Ser Ala Ala Ala Ser Ala Glu Ser Gly Gln Gln Gly Pro
            115                 120                 125
```

-continued

```
Gly Gly Tyr Gly Pro Gln Gln Pro Gly Tyr Gly Pro Gly
    130                 135                 140

Gln Gln Gly Pro Gly Gly Tyr Gly Pro Gly Gln Gln Gly Pro Ser Gly
145                 150                 155                 160

Pro Gly Ser Ala Ala Ala Ala Ala Ala Ser Gly Pro Gly Gln
                165                 170                 175

Gln Gly Pro Gly Gly Tyr Gly Pro Gly Gln Gln Gly Pro Gly Gly Tyr
            180                 185                 190

Gly Pro Gly Gln Gln Gly Pro Ser Gly Pro Gly Ser Ala Ala Ala
        195                 200                 205

Ala Ala Ala Ala Ser Gly Pro Gly Gln Gln Gly Pro Gly Gly Tyr Gly
210                 215                 220

Pro Gly Gln Gln Gly Pro Gly Gly Tyr Gly Pro Gly Gln Gln Gly Leu
225                 230                 235                 240

Ser Gly Pro Gly Ser Ala Ala Ala Ala Ala Ala Gly Pro Gly Gln
                245                 250                 255

Gln Gly Pro Gly Gly Tyr Gly Pro Gly Gln Gln Gly Pro Ser Gly Pro
            260                 265                 270

Gly Ser Ala Ala Ala Ala Ala Ala Ala Ala Gly Pro Gly Gly Tyr
        275                 280                 285

Gly Pro Gly Gln Gln Gly Pro Gly Gly Tyr Gly Pro Gly Gln Gln Gly
    290                 295                 300

Pro Ser Gly Ala Gly Ser Ala Ala Ala Ala Ala Ala Gly Pro Gly
305                 310                 315                 320

Gln Gln Gly Leu Gly Gly Tyr Gly Pro Gly Gln Gln Gly Pro Gly Gly
            325                 330                 335

Tyr Gly Pro Gly Gln Gln Gly Pro Gly Tyr Gly Pro Gly Ser Ala
        340                 345                 350

Ser Ala Ala Ala Ala Ala Gly Pro Gly Gln Gln Gly Pro Gly Gly
        355                 360                 365

Tyr Gly Pro Gly Gln Gln Gly Pro Ser Gly Pro Gly Ser Ala Ser Ala
        370                 375                 380

Ala Ala Ala Ala Ala Ala Gly Pro Gly Gly Tyr Gly Pro Gly Gln
385                 390                 395                 400

Gln Gly Pro Gly Gly Tyr Ala Pro Gly Gln Gln Gly Pro Ser Gly Pro
            405                 410                 415

Gly Ser Ala Ser Ala Ala Ala Ala Ala Ala Gly Pro Gly Gly
        420                 425                 430

Tyr Gly Pro Gly Gln Gln Gly Pro Gly Gly Tyr Ala Pro Gly Gln Gln
        435                 440                 445

Gly Pro Ser Gly Pro Gly Ser Ala Ala Ala Ala Ala Ala Ser Ala
    450                 455                 460

Gly Pro Gly Gly Tyr Gly Pro Ala Gln Gln Gly Pro Ser Gly Pro Gly
465                 470                 475                 480

Ile Ala Ala Ser Ala Ala Ser Ala Gly Pro Gly Gly Tyr Gly Pro Ala
                485                 490                 495

Gln Gln Gly Pro Ala Gly Tyr Gly Pro Gly Ser Ala Val Ala Ala Ser
            500                 505                 510

Ala Gly Ala Gly Ser Ala Gly Tyr Gly Pro Gly Ser Gln Ala Ser Ala
        515                 520                 525

Ala Ala Ser Arg Leu Ala Ser Pro Asp Ser Gly Ala Arg Val Ala Ser
        530                 535                 540

Ala Val Ser Asn Leu Val Ser Ser Gly Pro Thr Ser Ser Ala Ala Leu
545                 550                 555                 560
```

```
Ser Ser Val Ile Ser Asn Ala Val Ser Gln Ile Gly Ala Ser Asn Pro
            565                 570                 575

Gly Leu Ser Gly Cys Asp Val Leu Ile Gln Ala Leu Trp Lys Ser Phe
            580                 585                 590

Leu Leu Val
        595

(2) INFORMATION FOR SEQ ID NO:5:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Nephila clavipes (ix) FEATURE:
        (A) NAME/KEY: Duplication
        (B) LOCATION: 1..21
        (D) OTHER INFORMATION: /label= repeat_unit
            /note= "spider silk protein repeat unit"

(ix) FEATURE:
        (A) NAME/KEY: Region
        (B) LOCATION: 1..6
        (D) OTHER INFORMATION: /label= alanine_stretch
            /note= "this segment of alanines in the repeat
            unit can also contain 7 alanine residues."

(xi) SEQUENCE DESCRIPTION: SEQ ID NO:5:

Ala Ala Ala Ala Ala Ala Gly Gly Ala Gly Gln Gly Gly Tyr Gly Gly
1               5                   10                  15

Leu Gly Gly Gln Gly
            20

(2) INFORMATION FOR SEQ ID NO:6:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Nephila clavipes (ix) FEATURE:
        (A) NAME/KEY: Peptide
        (B) LOCATION: 1..33
        (D) OTHER INFORMATION: /label= representative
            /note= "This peptide is a representative one that
            illustrates the ggxgyg hexamer repeat motif of the
            spider silk protein I."

(xi) SEQUENCE DESCRIPTION: SEQ ID NO:6:

Gly Gly Gln Gly Ala Gly Ala Ala Ala Ala Gly Gly Ala Gly Gln Gly
1               5                   10                  15

Gly Tyr Gly Gly Val Gly Ser Gly Ala Ser Ala Ala Ser Ala Ala Ala
            20                  25                  30

Ser
```

```
(2) INFORMATION FOR SEQ ID NO:7:

(i) SEQUENCE CHARACTERISTICS:
         (A) LENGTH: 33 amino acids
         (B) TYPE: amino acid
         (D) TOPOLOGY: linear (ii) MOLECULE TYPE: peptide (v) FRAGMENT TYPE: internal (vi) ORIGINAL SOURCE:
         (A) ORGANISM: Nephila clavipes (ix) FEATURE:
         (A) NAME/KEY: Peptide
         (B) LOCATION: 1..33
         (D) OTHER INFORMATION: /label= repeat_unit
             /note= "The protein of the present invention is
             constituted primarily of repeats of this
             sequence."

(ix) FEATURE:
         (A) NAME/KEY: Region
         (B) LOCATION: 13..18
         (D) OTHER INFORMATION: /label= alanine_stretch
             /note= "This run of alanine residues can also have
             7 residues."

(ix) FEATURE:
         (A) NAME/KEY: Variable amino acid
         (B) LOCATION: 6
         (D) OTHER INFORMATION: /label= modified_a.a.
             /note= "This residue can be leucine, tyrosine or
             Glutamine"

(ix) FEATURE:
         (A) NAME/KEY: Variable amino acid
         (B) LOCATION: 9
         (D) OTHER INFORMATION: /label= modified_a.a.
             /note= "This residue can be leucine, tyrosine or
             glutamine and must be (ix) FEATURE:
         (A) NAME/KEY: Variable amino acid
         (B) LOCATION: 26
         (D) OTHER INFORMATION: /label= modified_a.a.
             /note= "This residue can be leucine, tyrosine or
             glutamine"

(xi) SEQUENCE DESCRIPTION: SEQ ID NO:7:

Ala Gly Arg Gly Gly Xaa Gly Gly Xaa Gly Ala Gly Ala Ala Ala Ala
1               5                  10                  15

Ala Ala Gly Gly Ala Gly Gln Gly Gly Xaa Gly Gly Leu Gly Gly Gln
            20                  25                  30

Gly (2) INFORMATION FOR SEQ ID NO:8:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (v) FRAGMENT TYPE: internal (vi) ORIGINAL SOURCE:
         (A) ORGANISM: Nephila clavipes (ix) FEATURE:
         (A) NAME/KEY: Peptide
         (B) LOCATION: 1..22
         (D) OTHER INFORMATION: /label= B_turn_repeat
             /note= "Beta turn repeat unit in spider silk
``` protein 2."

(xi) SEQUENCE DESCRIPTION: SEQ ID NO:8:

Gly Pro Gly Gln Gln Gly Pro Gly Gly Tyr Gly Pro Gly Gln Gln Gly
1               5                   10                  15

Pro Ser Gly Pro Gly Ser
            20

(2) INFORMATION FOR SEQ ID NO:9:

(i) SEQUENCE CHARACTERISTICS:
       (A) LENGTH: 5 amino acids
       (B) TYPE: amino acid
       (D) TOPOLOGY: linear (ii) MOLECULE TYPE: peptide (v) FRAGMENT TYPE: internal (vi) ORIGINAL SOURCE:
       (A) ORGANISM: Nephila clavipes (ix) FEATURE:
       (A) NAME/KEY: Peptide
       (B) LOCATION: 1..5
       (D) OTHER INFORMATION: /label= repeat_unit
           /note= "first variable region repeat motif of
           spider silk protein 2."

(xi) SEQUENCE DESCRIPTION: SEQ ID NO:9:

Gly Pro Gly Gly Tyr
1           5

(2) INFORMATION FOR SEQ ID NO:10:

(i) SEQUENCE CHARACTERISTICS:
       (A) LENGTH: 5 amino acids
       (B) TYPE: amino acid
       (D) TOPOLOGY: linear (ii) MOLECULE TYPE: peptide (v) FRAGMENT TYPE: internal (vi) ORIGINAL SOURCE:
       (A) ORGANISM: Nephila clavipes (ix) FEATURE:
       (A) NAME/KEY: Peptide
       (B) LOCATION: 1..5
       (D) OTHER INFORMATION: /label= repeat_unit
           /note= "second variable region repeat motif in
           spider silk protein 2."

(xi) SEQUENCE DESCRIPTION: SEQ ID NO:10:

Gly Pro Gly Gln Gln
1           5

(2) INFORMATION FOR SEQ ID NO:11:

(i) SEQUENCE CHARACTERISTICS:
       (A) LENGTH: 9 amino acids
       (B) TYPE: amino acid
       (D) TOPOLOGY: linear (ii) MOLECULE TYPE: peptide (v) FRAGMENT TYPE: internal (vi) ORIGINAL SOURCE:
       (A) ORGANISM: Nephila clavipes (ix) FEATURE:

(A) NAME/KEY: Peptide
            (B) LOCATION: 1..9
            (D) OTHER INFORMATION: /label= 1st_segment
                /note= "first segment of spider silk protein
                repeats."

(xi) SEQUENCE DESCRIPTION: SEQ ID NO:11:

Ala Gly Arg Gly Gly Leu Gly Gly Gln
1               5

(2) INFORMATION FOR SEQ ID NO:12:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Nephila clavipes (ix) FEATURE:
        (A) NAME/KEY: Peptide
        (B) LOCATION: 1..9
        (D) OTHER INFORMATION: /label= 2nd_segment
            /note= "Second segment of spider silk protein
            repeat unit. This segment is present in all
            repeats."

(ix) FEATURE:
        (A) NAME/KEY: Region
        (B) LOCATION: 4..9
        (D) OTHER INFORMATION: /label= alanine_stretch
            /note= "This run of alanines can also contain 7
            alanines."

(xi) SEQUENCE DESCRIPTION: SEQ ID NO:12:

Gly Ala Gly Ala Ala Ala Ala Ala Ala
1               5

(2) INFORMATION FOR SEQ ID NO:13:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Nephila clavipes (ix) FEATURE:
        (A) NAME/KEY: Peptide
        (B) LOCATION: 1..15
        (D) OTHER INFORMATION: /label= 3rd_segment
            /note= "Third segment of repeat unit of spider
            silk protein."

(ix) FEATURE:
        (A) NAME/KEY: Modified-site
        (B) LOCATION: 13
        (D) OTHER INFORMATION: /label= variable
            /note= "This amino acid can also be serine,
            asparagine or alanine"

(xi) SEQUENCE DESCRIPTION: SEQ ID NO:13:

Gly Gly Ala Gly Gln Gly Gly Tyr Gly Gly Leu Gly Gly Gln Gly
1               5                  10                  15

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Nephila clavipes (ix) FEATURE:
        (A) NAME/KEY: Peptide
        (B) LOCATION: 1..5
        (D) OTHER INFORMATION: /label= fragment
            /note= "fragment of sequence from Nephila dragline
            silk protein."

(xi) SEQUENCE DESCRIPTION: SEQ ID NO:14:

Gly Tyr Gly Pro Gly
1            5

(2) INFORMATION FOR SEQ ID NO:15:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Nephila clavipes (ix) FEATURE:
        (A) NAME/KEY: Peptide
        (B) LOCATION: 1..5
        (D) OTHER INFORMATION: /label= fragment
            /note= "fragment of sequence from Nephila dragline
            silk protein."

(xi) SEQUENCE DESCRIPTION: SEQ ID NO:15:

Gly Gln Gly Ala Gly
1            5

(2) INFORMATION FOR SEQ ID NO:16:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Nephila clavipes (ix) FEATURE:
        (A) NAME/KEY: Peptide
        (B) LOCATION: 1..5
        (D) OTHER INFORMATION: /label= fragment
            /note= "fragment of sequence from Nephila dragline
            silk protein."

(xi) SEQUENCE DESCRIPTION: SEQ ID NO:16:

Gly Ala Gly Gln Gly
1            5

```
(2) INFORMATION FOR SEQ ID NO:17:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Nephila clavipes (ix) FEATURE:
        (A) NAME/KEY: Peptide
        (B) LOCATION: 1..6
        (D) OTHER INFORMATION: /label= fragment
            /note= "fragment of sequence from Nephila dragline
            silk protein."

(xi) SEQUENCE DESCRIPTION: SEQ ID NO:17:

Gly Tyr Gly Gly Leu Gly
1               5

(2) INFORMATION FOR SEQ ID NO:18:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Nephila clavipes (ix) FEATURE:
        (A) NAME/KEY: Peptide
        (B) LOCATION: 1..4
        (D) OTHER INFORMATION: /label= fragment
            /note= "fragment of sequence from Nephila coccoon
            silk protein."

(xi) SEQUENCE DESCRIPTION: SEQ ID NO:18:

Ser Ala Phe Gln
1

(2) INFORMATION FOR SEQ ID NO:19:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Araneus gemmoides (ix) FEATURE:
        (A) NAME/KEY: Peptide
        (B) LOCATION: 1..10
        (D) OTHER INFORMATION: /label= fragment
            /note= "fragment of sequence from Araneus dragline
            silk protein."

(xi) SEQUENCE DESCRIPTION: SEQ ID NO:19:

Gly Pro Tyr Gly Pro Gly Gln Gln Gly Pro
```

(2) INFORMATION FOR SEQ ID NO:20:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Araneus gemmoides (ix) FEATURE:
        (A) NAME/KEY: Peptide
        (B) LOCATION: 1..4
        (D) OTHER INFORMATION: /label= fragment
            /note= "fragment of sequence from Araneus coccoon
            silk protein."

(xi) SEQUENCE DESCRIPTION: SEQ ID NO:20:

Phe Leu Gly Gly
1

(2) INFORMATION FOR SEQ ID NO:21:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Araneus gemmoides (ix) FEATURE:
        (A) NAME/KEY: Peptide
        (B) LOCATION: 1..10
        (D) OTHER INFORMATION: /label= fragment
            /note= "fragment of sequence from Araneus coccoon
            silk protein."

(ix) FEATURE:
        (A) NAME/KEY: Modified-site
        (B) LOCATION: 6
        (D) OTHER INFORMATION: /label= leucine
            /note= "This amino acid can also be isoleucine."

(xi) SEQUENCE DESCRIPTION: SEQ ID NO:21:

Ser Val Gly Leu Val Leu Ala Tyr Ala Leu
1               5                   10

(2) INFORMATION FOR SEQ ID NO:22:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (ix) FEATURE:
        (A) NAME/KEY: -
        (B) LOCATION: 1..14
        (D) OTHER INFORMATION: /label= oligonucleotide
            /note= "Synthetic degenerate oligonucleotide for screening Nephila clavipes cDNA library."

(xi) SEQUENCE DESCRIPTION: SEQ ID NO:22:

CCNCGNCCNG TYCC                                                       14

(2) INFORMATION FOR SEQ ID NO:23:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: -
        (B) LOCATION: group(1..21, 41..57)
        (D) OTHER INFORMATION: /label= vector
            /note= "Bluescript SK+ vector sequence."

(ix) FEATURE:
        (A) NAME/KEY: -
        (B) LOCATION: 22..41
        (D) OTHER INFORMATION: /label= insert
            /note= "insert segment shown in box, page 16, line
            37 of Specification.  "nnnn" region is
            approximately 2.0 kilobases."

(xi) SEQUENCE DESCRIPTION: SEQ ID NO:23:

GATATCGAAT TCCTGCAGCC CCAGGNNNNN NNNNNNNNGG GATCCACTAG TTCTAGA         57

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: -
        (B) LOCATION: 1..24
        (D) OTHER INFORMATION: /label= vector
            /note= "portion of the sequence of the pGEM3Z
            cloning vector"

(xi) SEQUENCE DESCRIPTION: SEQ ID NO:24:

AGGTCGACTC TAGAGGATCC CCGG                                            24

(2) INFORMATION FOR SEQ ID NO:25:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (ix) FEATURE:
        (A) NAME/KEY: -
        (B) LOCATION: 1..14
        (D) OTHER INFORMATION: /label= oligonucleotide
            /note= "oligonucleotide derived from reverse
            translation of GYGPG pentapeptide from Nephila
            clavipes silk protein 2"

(xi) SEQUENCE DESCRIPTION: SEQ ID NO:25:

```
CCNGGNCCAT ANCC                                                          14
```

(2) INFORMATION FOR SEQ ID NO:26:

(i) SEQUENCE CHARACTERISTICS:
        (A) LENGTH: 47 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..47
        (D) OTHER INFORMATION: /label= silk2_repeat (xi) SEQUENCE DESCRIPTION: SEQ ID NO:26:

```
Gly Pro Gly Gln Gln Gly Pro Gly Gly Tyr Gly Pro Gly Gln Gln Gly
1               5                  10                  15

Pro Ser Gly Pro Gly Ser Ala Ala Ala Ala Ala Ala Ala Ala Ala Ala
            20                  25                  30

Gly Pro Gly Gly Tyr Gly Pro Gly Gln Gln Gly Pro Gly Gly Tyr
        35                  40                  45
```

(2) INFORMATION FOR SEQ ID NO:27:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..38
        (D) OTHER INFORMATION: /label= silk2_repeat (xi) SEQUENCE DESCRIPTION: SEQ ID NO:27:

```
Gly Pro Gly Gln Gln Gly Pro Gly Arg Tyr Gly Pro Gly Gln Gln Gly
1               5                  10                  15

Pro Ser Gly Pro Gly Ser Ala Ala Ala Ala Ala Ala Gly Ser Gly Gln
            20                  25                  30

Gln Gly Pro Gly Gly Tyr
        35
```

(2) INFORMATION FOR SEQ ID NO:28:

(i) SEQUENCE CHARACTERISTICS:
        (A) LENGTH: 52 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
             (A) ORGANISM: nephila clavipes (ix) FEATURE:
             (A) NAME/KEY: Peptide
             (B) LOCATION: 1..52
             (D) OTHER INFORMATION: /label= silk2_repeat (xi) SEQUENCE DESCRIPTION: SEQ ID NO:28:

Gly Pro Arg Gln Gln Gly Pro Gly Gly Tyr Gly Gln Gly Gln Gly
1               5                  10                  15

Pro Ser Gly Pro Gly Ser Ala Ala Ala Ala Ser Ala Ala Ala Ser Ala
            20                  25                  30

Glu Ser Gly Gln Gln Gly Pro Gly Gly Tyr Gly Pro Gly Gln Gln Gly
            35                  40                  45

Pro Gly Gly Tyr
        50

(2) INFORMATION FOR SEQ ID NO:29:

(i) SEQUENCE CHARACTERISTICS:
             (A) LENGTH: 41 amino acids
             (B) TYPE: amino acid
             (C) STRANDEDNESS: Not Relevant
             (D) TOPOLOGY: Not Relevant (ii) MOLECULE TYPE: peptide (iii) HYPOTHETICAL: NO (v) FRAGMENT TYPE: internal (vi) ORIGINAL SOURCE:
             (A) ORGANISM: nephila clavipes (ix) FEATURE:
             (A) NAME/KEY: Peptide
             (B) LOCATION: 1..41
             (D) OTHER INFORMATION: /label= silk2_repeat (xi) SEQUENCE DESCRIPTION: SEQ ID NO:29:

Gly Pro Gly Gln Gln Gly Pro Gly Gly Tyr Gly Pro Gly Gln Gln Gly
1               5                  10                  15

Pro Ser Gly Pro Gly Ser Ala Ala Ala Ala Ala Ala Ala Ser Gly
            20                  25                  30

Pro Gly Gln Gln Gly Pro Gly Gly Tyr
        35                  40

(2) INFORMATION FOR SEQ ID NO:30:

(i) SEQUENCE CHARACTERISTICS:
             (A) LENGTH: 40 amino acids
             (B) TYPE: amino acid
             (C) STRANDEDNESS: Not Relevant
             (D) TOPOLOGY: Not Relevant (ii) MOLECULE TYPE: peptide (iii) HYPOTHETICAL: NO (v) FRAGMENT TYPE: internal (vi) ORIGINAL SOURCE:
             (A) ORGANISM: nephila clavipes (ix) FEATURE:

(A) NAME/KEY: Peptide
          (B) LOCATION: 1..40
          (D) OTHER INFORMATION: /label= silk2_repeat (xi) SEQUENCE DESCRIPTION: SEQ ID NO:30:

Gly Pro Gly Gln Gln Gly Pro Gly Gly Tyr Gly Pro Gly Gln Gln Gly
1               5                  10                  15

Pro Ser Gly Pro Gly Ser Ala Ala Ala Ala Ala Ala Ala Ser Gly Pro
            20                  25                  30

Gly Gln Gln Gly Pro Gly Gly Tyr
            35                  40

(2) INFORMATION FOR SEQ ID NO:31:

(i) SEQUENCE CHARACTERISTICS:
          (A) LENGTH: 29 amino acids
          (B) TYPE: amino acid
          (C) STRANDEDNESS: Not Relevant
          (D) TOPOLOGY: Not Relevant (ii) MOLECULE TYPE: peptide (iii) HYPOTHETICAL: NO (v) FRAGMENT TYPE: internal (vi) ORIGINAL SOURCE:
          (A) ORGANISM: nephila clavipes (ix) FEATURE:
          (A) NAME/KEY: Peptide
          (B) LOCATION: 1..29
          (D) OTHER INFORMATION: /label= silk2_repeat (xi) SEQUENCE DESCRIPTION: SEQ ID NO:31:

Gly Pro Gly Gln Gln Gly Pro Gly Gly Tyr Gly Pro Gly Gln Gln Gly
1               5                  10                  15

Leu Ser Gly Pro Gly Ser Ala Ala Ala Ala Ala Ala Ala
            20                  25

(2) INFORMATION FOR SEQ ID NO:32:

(i) SEQUENCE CHARACTERISTICS:
          (A) LENGTH: 36 amino acids
          (B) TYPE: amino acid
          (C) STRANDEDNESS: Not Relevant
          (D) TOPOLOGY: Not Relevant (ii) MOLECULE TYPE: peptide (iii) HYPOTHETICAL: NO (v) FRAGMENT TYPE: internal (vi) ORIGINAL SOURCE:
          (A) ORGANISM: nephila clavipes (ix) FEATURE:
          (A) NAME/KEY: Peptide
          (B) LOCATION: 1..36
          (D) OTHER INFORMATION: /label= silk2_repeat (xi) SEQUENCE DESCRIPTION: SEQ ID NO:32:

Gly Pro Gly Gln Gln Gly Pro Gly Gly Tyr Gly Pro Gly Gln Gln Gly
1               5                  10                  15

Pro Ser Gly Pro Gly Ser Ala Ala Ala Ala Ala Ala Ala Ala Gly
            20                  25                  30

Pro Gly Gly Tyr
        35

(2) INFORMATION FOR SEQ ID NO:33:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..39
        (D) OTHER INFORMATION: /label= silk2_repeat (xi) SEQUENCE DESCRIPTION: SEQ ID NO:33:

```
Gly Pro Gly Gln Gln Gly Pro Gly Gly Tyr Gly Pro Gly Gln Gln Gly
 1               5                  10                  15

Pro Ser Gly Ala Gly Ser Ala Ala Ala Ala Ala Ala Gly Pro Gly
            20                  25                  30

Gln Gln Gly Leu Gly Gly Tyr
        35
```

(2) INFORMATION FOR SEQ ID NO:34:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..32
        (D) OTHER INFORMATION: /label= silk2_repeat (xi) SEQUENCE DESCRIPTION: SEQ ID NO:34:

```
Gly Pro Gly Gln Gln Gly Pro Gly Gly Tyr Gly Pro Gly Gln Gln Gly
 1               5                  10                  15

Pro Gly Gly Tyr Gly Pro Gly Ser Ala Ser Ala Ala Ala Ala Ala Ala
            20                  25                  30
```

(2) INFORMATION FOR SEQ ID NO:35:

(i) SEQUENCE CHARACTERISTICS:
        (A) LENGTH: 37 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
             (A) ORGANISM: nephila clavipes (ix) FEATURE:
             (A) NAME/KEY: Peptide
             (B) LOCATION: 1..37
             (D) OTHER INFORMATION: /label= silk2_repeat (xi) SEQUENCE DESCRIPTION: SEQ ID NO:35:

Gly Pro Gly Gln Gln Gly Pro Gly Gly Tyr Gly Pro Gly Gln Gln Gly
1               5                  10                  15

Pro Ser Gly Pro Gly Ser Ala Ser Ala Ala Ala Ala Ala Ala Ala Ala
            20                  25                  30

Gly Pro Gly Gly Tyr
        35

(2) INFORMATION FOR SEQ ID NO:36:

(i) SEQUENCE CHARACTERISTICS:
            (A) LENGTH: 37 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (v) FRAGMENT TYPE: internal (vi) ORIGINAL SOURCE:
            (A) ORGANISM: nephila clavipes (ix) FEATURE:
            (A) NAME/KEY: Peptide
            (B) LOCATION: 1..37
            (D) OTHER INFORMATION: /label= silk2_repeat (xi) SEQUENCE DESCRIPTION: SEQ ID NO:36:

Gly Pro Gly Gln Gln Gly Pro Gly Gly Tyr Ala Pro Gly Gln Gln Gly
1               5                  10                  15

Pro Ser Gly Pro Gly Ser Ala Ser Ala Ala Ala Ala Ala Ala Ala Ala
            20                  25                  30

Gly Pro Gly Gly Tyr
        35

(2) INFORMATION FOR SEQ ID NO:37:

(i) SEQUENCE CHARACTERISTICS:
            (A) LENGTH: 36 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (v) FRAGMENT TYPE: internal (vi) ORIGINAL SOURCE:
            (A) ORGANISM: nephila clavipes (ix) FEATURE:
            (A) NAME/KEY: Peptide
            (B) LOCATION: 1..36
            (D) OTHER INFORMATION: /label= silk2_repeat (xi) SEQUENCE DESCRIPTION: SEQ ID NO:37:

Gly Pro Gly Gln Gln Gly Pro Gly Gly Tyr Ala Pro Gly Gln Gln Gly
1               5                  10                  15

```
Pro Ser Gly Pro Gly Ser Ala Ala Ala Ala Ala Ala Ser Ala Gly
        20                  25                  30

Pro Gly Gly Tyr
        35
```

(2) INFORMATION FOR SEQ ID NO:38:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..25
        (D) OTHER INFORMATION: /label= silk1_repeat (xi) SEQUENCE DESCRIPTION: SEQ ID NO:38:

```
Gln Gly Ala Gly Ala Ala Ala Ala Ala Ala Gly Gly Ala Gly Gln Gly
1               5                   10                  15

Gly Tyr Gly Gly Leu Gly Gly Gln Gly
        20                  25
```

(2) INFORMATION FOR SEQ ID NO:39:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..13
        (D) OTHER INFORMATION: /label= silk1_repeat (xi) SEQUENCE DESCRIPTION: SEQ ID NO:39:

```
Ala Gly Gln Gly Gly Tyr Gly Gly Leu Gly Gly Gln Gly
1               5                   10
```

(2) INFORMATION FOR SEQ ID NO:40:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
            (A) ORGANISM: nephila clavipes (ix) FEATURE:
            (A) NAME/KEY: Peptide
            (B) LOCATION: 1..28
            (D) OTHER INFORMATION: /label= silk1_repeat (xi) SEQUENCE DESCRIPTION: SEQ ID NO:40:

Ala Gly Gln Gly Ala Gly Ala Ala Ala Ala Ala Ala Ala Gly Gly Ala
1               5                   10                  15

Gly Gln Gly Gly Tyr Gly Gly Leu Gly Ser Gln Gly
            20                  25

(2) INFORMATION FOR SEQ ID NO:41:

(i) SEQUENCE CHARACTERISTICS:
            (A) LENGTH: 30 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (v) FRAGMENT TYPE: internal (vi) ORIGINAL SOURCE:
            (A) ORGANISM: nephila clavipes (ix) FEATURE:
            (A) NAME/KEY: Peptide
            (B) LOCATION: 1..30
            (D) OTHER INFORMATION: /label= silk1_repeat (xi) SEQUENCE DESCRIPTION: SEQ ID NO:41:

Ala Gly Arg Gly Gly Gln Gly Ala Gly Ala Ala Ala Ala Ala Ala Gly
1               5                   10                  15

Gly Ala Gly Gln Gly Gly Tyr Gly Gly Leu Gly Ser Gln Gly
            20                  25                  30

(2) INFORMATION FOR SEQ ID NO:42:

(i) SEQUENCE CHARACTERISTICS:
            (A) LENGTH: 34 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (v) FRAGMENT TYPE: internal (vi) ORIGINAL SOURCE:
            (A) ORGANISM: nephila clavipes (ix) FEATURE:
            (A) NAME/KEY: Peptide
            (B) LOCATION: 1..34
            (D) OTHER INFORMATION: /label= silk1_repeat (xi) SEQUENCE DESCRIPTION: SEQ ID NO:42:

Ala Gly Arg Gly Gly Leu Gly Gly Gln Gly Ala Gly Ala Ala Ala Ala
1               5                   10                  15

Ala Ala Ala Gly Gly Ala Gly Gln Gly Gly Tyr Gly Gly Leu Gly Asn
            20                  25                  30

Gln Gly (2) INFORMATION FOR SEQ ID NO:43:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..28
        (D) OTHER INFORMATION: /label= silk1_repeat (xi) SEQUENCE DESCRIPTION: SEQ ID NO:43:

```
Ala Gly Arg Gly Gly Gln Gly Ala Ala Ala Ala Ala Ala Gly Gly Ala
 1               5                  10                  15
Gly Gln Gly Gly Tyr Gly Gly Leu Gly Ser Gln Gly
                20                  25
```

(2) INFORMATION FOR SEQ ID NO:44:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..32
        (D) OTHER INFORMATION: /label= silk1_repeat (xi) SEQUENCE DESCRIPTION: SEQ ID NO:44:

```
Ala Gly Arg Gly Gly Leu Gly Gly Gln Ala Gly Ala Ala Ala Ala Ala
 1               5                  10                  15
Ala Gly Gly Ala Gly Gln Gly Gly Tyr Gly Gly Leu Gly Gly Gln Gly
                20                  25                  30
```

(2) INFORMATION FOR SEQ ID NO:45:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes

```
        (ix) FEATURE:
              (A) NAME/KEY: Peptide
              (B) LOCATION: 1..13
              (D) OTHER INFORMATION: /label= silk1_repeat (xi) SEQUENCE DESCRIPTION: SEQ ID NO:45:

Ala Gly Gln Gly Gly Tyr Gly Gly Leu Gly Ser Gln Gly
1               5                  10

(2) INFORMATION FOR SEQ ID NO:46:

(i) SEQUENCE CHARACTERISTICS:
              (A) LENGTH: 31 amino acids
              (B) TYPE: amino acid
              (C) STRANDEDNESS: Not Relevant
              (D) TOPOLOGY: Not Relevant (ii) MOLECULE TYPE: peptide (iii) HYPOTHETICAL: NO (v) FRAGMENT TYPE: internal (vi) ORIGINAL SOURCE:
              (A) ORGANISM: nephila clavipes (ix) FEATURE:
              (A) NAME/KEY: Peptide
              (B) LOCATION: 1..31
              (D) OTHER INFORMATION: /label= silk1_repeat (xi) SEQUENCE DESCRIPTION: SEQ ID NO:46:

Ala Gly Arg Gly Gly Leu Gly Gly Gln Gly Ala Gly Ala Ala Ala Ala
1               5                  10                  15
Ala Ala Ala Gly Gly Ala Gly Gln Gly Gly Leu Gly Gly Gln Gly
                20                  25                  30

(2) INFORMATION FOR SEQ ID NO:47:

(i) SEQUENCE CHARACTERISTICS:
              (A) LENGTH: 27 amino acids
              (B) TYPE: amino acid
              (C) STRANDEDNESS: Not Relevant
              (D) TOPOLOGY: Not Relevant (ii) MOLECULE TYPE: peptide (iii) HYPOTHETICAL: NO (v) FRAGMENT TYPE: internal (vi) ORIGINAL SOURCE:
              (A) ORGANISM: nephila clavipes (ix) FEATURE:
              (A) NAME/KEY: Peptide
              (B) LOCATION: 1..27
              (D) OTHER INFORMATION: /label= silk1_repeat (xi) SEQUENCE DESCRIPTION: SEQ ID NO:47:

Ala Gly Gln Gly Ala Gly Ala Ser Ala Ala Ala Ala Gly Gly Ala Gly
1               5                  10                  15
Gln Gly Gly Tyr Gly Gly Leu Gly Ser Gln Gly
                20                  25

(2) INFORMATION FOR SEQ ID NO:48:

(i) SEQUENCE CHARACTERISTICS:
              (A) LENGTH: 30 amino acids
              (B) TYPE: amino acid
              (C) STRANDEDNESS: Not Relevant
```

(D) TOPOLOGY: Not Relevant (ii) MOLECULE TYPE: peptide (iii) HYPOTHETICAL: NO (v) FRAGMENT TYPE: internal (vi) ORIGINAL SOURCE:
           (A) ORGANISM: nephila clavipes (ix) FEATURE:
           (A) NAME/KEY: Peptide
           (B) LOCATION: 1..30
           (D) OTHER INFORMATION: /label= silk1_repeat (xi) SEQUENCE DESCRIPTION: SEQ ID NO:48:

Ala Gly Arg Gly Gly Glu Gly Ala Gly Ala Ala Ala Ala Ala Gly
1               5                  10                  15

Gly Ala Gly Gln Gly Gly Tyr Gly Gly Leu Gly Gly Gln Gly
            20                  25                  30

(2) INFORMATION FOR SEQ ID NO:49:

(i) SEQUENCE CHARACTERISTICS:
           (A) LENGTH: 13 amino acids
           (B) TYPE: amino acid
           (C) STRANDEDNESS: Not Relevant
           (D) TOPOLOGY: Not Relevant (ii) MOLECULE TYPE: peptide (iii) HYPOTHETICAL: NO (v) FRAGMENT TYPE: internal (vi) ORIGINAL SOURCE:
           (A) ORGANISM: nephila clavipes (ix) FEATURE:
           (A) NAME/KEY: Peptide
           (B) LOCATION: 1..13
           (D) OTHER INFORMATION: /label= silk1_repeat (xi) SEQUENCE DESCRIPTION: SEQ ID NO:49:

Ala Gly Gln Gly Gly Tyr Gly Gly Leu Gly Ser Gln Gly
1               5                  10

(2) INFORMATION FOR SEQ ID NO:50:

(i) SEQUENCE CHARACTERISTICS:
           (A) LENGTH: 28 amino acids
           (B) TYPE: amino acid
           (C) STRANDEDNESS: Not Relevant
           (D) TOPOLOGY: Not Relevant (ii) MOLECULE TYPE: peptide (iii) HYPOTHETICAL: NO (v) FRAGMENT TYPE: internal (vi) ORIGINAL SOURCE:
           (A) ORGANISM: nephila clavipes (ix) FEATURE:
           (A) NAME/KEY: Peptide
           (B) LOCATION: 1..28
           (D) OTHER INFORMATION: /label= silk1_repeat (xi) SEQUENCE DESCRIPTION: SEQ ID NO:50:

Ala Gly Arg Gly Gly Leu Gly Gly Gln Gly Ala Gly Ala Ala Ala Ala
1               5                  10                  15

```
Gly Gly Ala Gly Gln Gly Gly Leu Gly Gly Gln Gly
            20                  25
```

(2) INFORMATION FOR SEQ ID NO:51:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..27
        (D) OTHER INFORMATION: /label= silk1_repeat (xi) SEQUENCE DESCRIPTION: SEQ ID NO:51:

```
Ala Gly Gln Gly Ala Gly Ala Ala Ala Ala Ala Gly Gly Ala Gly
1               5                   10                  15
Gln Gly Gly Tyr Gly Gly Leu Gly Ser Gln Gly
            20                  25
```

(2) INFORMATION FOR SEQ ID NO:52:

(i) SEQUENCE CHARACTERISTICS:
        (A) LENGTH: 34 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..34
        (D) OTHER INFORMATION: /label= silk1_repeat (xi) SEQUENCE DESCRIPTION: SEQ ID NO:52:

```
Ala Gly Arg Gly Gly Leu Gly Gly Gln Gly Ala Gly Ala Val Ala Ala
1               5                   10                  15
Ala Ala Ala Gly Gly Ala Gly Gln Gly Gly Tyr Gly Gly Leu Gly Ser
            20                  25                  30
Gln Gly
```

(2) INFORMATION FOR SEQ ID NO:53:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
           (A) ORGANISM: nephila clavipes (ix) FEATURE:
           (A) NAME/KEY: Peptide
           (B) LOCATION: 1..30
           (D) OTHER INFORMATION: /label= silk1_repeat (xi) SEQUENCE DESCRIPTION: SEQ ID NO:53:

Ala Gly Arg Gly Gly Gln Gly Ala Gly Ala Ala Ala Ala Ala Gly
1               5                  10                  15

Gly Ala Gly Gln Arg Gly Tyr Gly Gly Leu Gly Asn Gln Gly
                20                  25                  30

(2) INFORMATION FOR SEQ ID NO:54:

(i) SEQUENCE CHARACTERISTICS:
           (A) LENGTH: 34 amino acids
           (B) TYPE: amino acid
           (C) STRANDEDNESS: Not Relevant
           (D) TOPOLOGY: Not Relevant (ii) MOLECULE TYPE: peptide (iii) HYPOTHETICAL: NO (v) FRAGMENT TYPE: internal (vi) ORIGINAL SOURCE:
           (A) ORGANISM: nephila clavipes (ix) FEATURE:
           (A) NAME/KEY: Peptide
           (B) LOCATION: 1..34
           (D) OTHER INFORMATION: /label= silk1_repeat (xi) SEQUENCE DESCRIPTION: SEQ ID NO:54:

Ala Gly Arg Gly Gly Leu Gly Gly Gln Gly Ala Gly Ala Ala Ala
1               5                  10                  15

Ala Ala Ala Gly Gly Ala Gly Gln Gly Gly Tyr Gly Gly Leu Gly Asn
                20                  25                  30

Gln Gly (2) INFORMATION FOR SEQ ID NO:55:

(i) SEQUENCE CHARACTERISTICS:
           (A) LENGTH: 27 amino acids
           (B) TYPE: amino acid
           (C) STRANDEDNESS: Not Relevant
           (D) TOPOLOGY: Not Relevant (ii) MOLECULE TYPE: peptide (iii) HYPOTHETICAL: NO (v) FRAGMENT TYPE: internal (vi) ORIGINAL SOURCE:
           (A) ORGANISM: nephila clavipes (ix) FEATURE:
           (A) NAME/KEY: Peptide
           (B) LOCATION: 1..27
           (D) OTHER INFORMATION: /label= silk1_repeat (xi) SEQUENCE DESCRIPTION: SEQ ID NO:55:

Ala Gly Arg Gly Gly Gln Gly Ala Ala Ala Ala Ala Gly Gly Ala Gly
1               5                  10                  15

```
Gln Gly Gly Tyr Gly Gly Leu Gly Ser Gln Gly
         20                  25

(2) INFORMATION FOR SEQ ID NO:56:

(i) SEQUENCE CHARACTERISTICS:
          (A) LENGTH: 27 amino acids
          (B) TYPE: amino acid
          (C) STRANDEDNESS: Not Relevant
          (D) TOPOLOGY: Not Relevant (ii) MOLECULE TYPE: peptide (iii) HYPOTHETICAL: NO (v) FRAGMENT TYPE: internal (vi) ORIGINAL SOURCE:
          (A) ORGANISM: nephila clavipes (ix) FEATURE:
          (A) NAME/KEY: Peptide
          (B) LOCATION: 1..27
          (D) OTHER INFORMATION: /label= silk1_repeat (xi) SEQUENCE DESCRIPTION: SEQ ID NO:56:

Ala Gly Arg Gly Gly Gln Gly Ala Gly Ala Ala Ala Ala Ala Val
1               5                  10                  15

Gly Ala Gly Gln Glu Gly Ile Arg Gly Gln Gly
         20                  25

(2) INFORMATION FOR SEQ ID NO:57:

(i) SEQUENCE CHARACTERISTICS:
          (A) LENGTH: 13 amino acids
          (B) TYPE: amino acid
          (C) STRANDEDNESS: Not Relevant
          (D) TOPOLOGY: Not Relevant (ii) MOLECULE TYPE: peptide (iii) HYPOTHETICAL: NO (v) FRAGMENT TYPE: internal (vi) ORIGINAL SOURCE:
          (A) ORGANISM: nephila clavipes (ix) FEATURE:
          (A) NAME/KEY: Peptide
          (B) LOCATION: 1..13
          (D) OTHER INFORMATION: /label= silk1_repeat (xi) SEQUENCE DESCRIPTION: SEQ ID NO:57:

Ala Gly Gln Gly Gly Tyr Gly Gly Leu Gly Ser Gln Gly
1               5                  10

(2) INFORMATION FOR SEQ ID NO:58:

(i) SEQUENCE CHARACTERISTICS:
          (A) LENGTH: 30 amino acids
          (B) TYPE: amino acid
          (C) STRANDEDNESS: Not Relevant
          (D) TOPOLOGY: Not Relevant (ii) MOLECULE TYPE: peptide (iii) HYPOTHETICAL: NO (v) FRAGMENT TYPE: internal (vi) ORIGINAL SOURCE:
          (A) ORGANISM: nephila clavipes
```

(ix) FEATURE:
        (A) NAME/KEY: Peptide
        (B) LOCATION: 1..30
        (D) OTHER INFORMATION: /label= silk1_repeat (xi) SEQUENCE DESCRIPTION: SEQ ID NO:58:

Ser Gly Arg Gly Gly Leu Gly Gly Gln Gly Ala Gly Ala Ala Ala
1               5                   10                  15

Ala Ala Gly Gly Ala Gly Gln Gly Gly Leu Gly Gly Gln Gly
            20                  25                  30

(2) INFORMATION FOR SEQ ID NO:59:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..27
        (D) OTHER INFORMATION: /label= silk1_repeat (xi) SEQUENCE DESCRIPTION: SEQ ID NO:59:

Ala Gly Gln Gly Ala Gly Ala Ala Ala Ala Ala Gly Gly Val Arg
1               5                   10                  15

Gln Gly Gly Tyr Gly Gly Leu Gly Ser Gln Gly
            20                  25

(2) INFORMATION FOR SEQ ID NO:60:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: nephila clavipes (ix) FEATURE:
        (A) NAME/KEY: Peptide
        (B) LOCATION: 1..30
        (D) OTHER INFORMATION: /label= silk1_repeat (xi) SEQUENCE DESCRIPTION: SEQ ID NO:60:

Ala Gly Arg Gly Gly Gln Gly Ala Gly Ala Ala Ala Ala Ala Gly
1               5                   10                  15

Gly Ala Gly Gln Gly Gly Tyr Gly Gly Leu Gly Gly Gln Gly
            20                  25                  30

(2) INFORMATION FOR SEQ ID NO:61:

(i) SEQUENCE CHARACTERISTICS:
        (A) LENGTH: 30 amino acids (B) TYPE: amino acid
            (C) STRANDEDNESS: Not Relevant
            (D) TOPOLOGY: Not Relevant (ii) MOLECULE TYPE: peptide (iii) HYPOTHETICAL: NO (v) FRAGMENT TYPE: internal (vi) ORIGINAL SOURCE:
            (A) ORGANISM: nephila clavipes (ix) FEATURE:
            (A) NAME/KEY: Peptide
            (B) LOCATION: 1..30
            (D) OTHER INFORMATION: /label= silk1_repeat (xi) SEQUENCE DESCRIPTION: SEQ ID NO:61:

Val Gly Arg Gly Gly Leu Gly Gly Gln Gly Ala Gly Ala Ala Ala
1               5                  10                 15

Gly Gly Ala Gly Gln Gly Gly Tyr Gly Gly Val Gly Ser Gly
                20                  25                 30

(2) INFORMATION FOR SEQ ID NO:62:

(i) SEQUENCE CHARACTERISTICS:
            (A) LENGTH: 13 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (v) FRAGMENT TYPE: internal (vi) ORIGINAL SOURCE:
            (A) ORGANISM: nephila clavipes (ix) FEATURE:
            (A) NAME/KEY: Peptide
            (B) LOCATION: 1..13
            (D) OTHER INFORMATION: /label= silk1_repeat (xi) SEQUENCE DESCRIPTION: SEQ ID NO:62:

Ala Ser Ala Ala Ser Ala Ala Ala Ser Arg Leu Ser Ser
1               5                  10

ISOLATED DNA CODING FOR SPIDER SILK PROTEIN, A REPLICABLE VECTOR AND A TRANSFORMED CELL CONTAINING THE DNA

This application is a continuation of application Ser. No. 07/684,819 filed on Apr. 15, 1991, now abandoned, which is a continuation-in-part, of application Ser. No. 07/511,792 filed on Apr. 20, 1990 now abandoned.

The invention described in this application was made in part with U.S. Government support by contracts with the Office of Naval Research (Contract No. N00014-89-J-1564) and the U.S. Army Research Office (Contract No. DAAL03-91-G-0044) and the Government has certain rights in this invention.

FIELD OF THE INVENTION

The present invention relates to the preparation of spider silk protein by recombinant DNA techniques.

BACKGROUND OF THE INVENTION

Major ampullate (dragline) silk of orb web spiders possesses unique physical properties, combining high tensile strength and substantial elasticity, Denny, M. W. *J. Exp. Biol.*, 65, 483–506 (1976); Lucas, F. *Discovery*, 25, 20–26 (1964). Previous investigations suggest that spider silk is composed of a single large protein, primarily containing pseudo-crystalline regions of stack β-pleated sheet alternating with amorphous domains, Warwicker, J. O., *J. Mol. Biol.*, 2, 350–362 (1960); Lucase, F. et al, *J. Text Inst.*, 46, T440–T452 (1985); Hepburn, H. R. et al., *Insect Biochem.*, 9, 69–71 (1979). The molecular basis for spider silk elasticity is presently unknown, although it has been suggested that an entropy driven process like that found in rubber is involved, Gosline, J. M., et al., *Nature*, 309, 551–552 (1984). It has also been speculated that the amorphous regions contribute substantially to the elastic properties of the fiber, Hepburn, H. R., et al., *Insect Biochem.*, 9, 69–77 (1979).

SUMMARY OF THE INVENTION

It is an object of the present invention to produce spider silk protein by recombinant DNA techniques.

It is also an object of the present invention to provide, for the first time, a spider silk protein in purified form. Specifically, the inventors have discovered that spider silk protein from *Nephila clavipes* naturally occurs as a mixture of at least two spider silk proteins. The inventors have cloned portions of the genes for both of these proteins and have named these proteins Silk Protein 1 and Silk Protein 2. Because these two genes have been independently cloned, these two proteins can be independently prepared by recombinant techniques. The silk proteins can then be purified, i.e., separated from contaminating materials in the expression system, to produce purified or homogeneous Silk Protein 1 or purified or homogeneous Silk Protein 2. The spider Silk Protein 1 is therefore free from spider Silk Protein 2 and the spider Silk Protein 2 is free from spider Silk Protein 1. These proteins can be used in a pure form or they can be mixed with each other in order to approximate the properties of natural spider silk. The Silk Protein 1 and Silk Protein 2 can be mixed in an amount of 100:1 to 1:100, preferably 10:1 to 1:2, more preferably 5:1 to 1:1.

The isolated cDNA of the invention preferably codes for spider silk protein containing the sequence shown in FIG. 6 or FIG. 7 or a fragment or variant thereof.

The amino acid composition of the fragment or variant thereof may match that of the native spider silk protein. The structure, via Fourier transform infrared spectroscopy (FTIR), may show predominantly a β-sheet structure. The fragment of variant, like the native protein, should be soluble only in highly chaotropic solvents such LiSCN, Li perchlorate or formic acid.

The spider silk protein can be characterized by repeating α and β regions and optional variable regions. The full cDNA spider Silk Protein 1 and spider Silk Protein 2 have not been cloned or sequenced. However, it can be expected that spider Silk Protein 1 and spider Silk Protein 2 each may have a molecular weight less than 300,000 daltons, probably greater than 100,000 but less than 300,000 daltons, preferably 120,000 to 300,000 daltons. Spider Silk Protein 1 and spider Silk Protein 2 may each have 900 to 2700 amino acids with 25 to 100, preferably 30 to 90 repeats. For example, the spider silk protein may be represented by the formula $$[(\alpha)(\beta)]_p$$

wherein α is an amorphous region which can form an α-helix when stretched, β is a region which can form β-sheets (when in a folded conformation) and p is an integer of 1 to 100, preferably 15 to 50, more preferably 18 to 22 for fragments or p is an integer of 25 to 100, preferably 30 to 90 for the full length spider silk protein. The sequence may also contain optional variable regions interspersed between the α and/or β regions.

A useful protein or fragment should be (1) insoluble inside the cell in which it is expressed or (2) capable of being formed into an insoluble fiber under normal conditions by which fibers are made. Preferably, the protein is insoluble under conditions (1) and (2). Specifically, the protein or fragment should be insoluble in a solvent such as water, alcohol (methanol, ethanol, etc.), acetone and/or organic acids, etc. The protein or fragment should be capable of being formed into a fiber having high tensile strength, e.g., a tensile strength of 0.5x to 2x wherein x is the tensile strength of a fiber formed from the corresponding natural silk or the whole protein. The protein or fragment should also be capable of being formed into a fiber possessing an elasticity of at least 15%, more preferably about 25%.

Variants of the spider silk protein may be formed into a fiber having a tensile strength and/or elasticity which is greater than that of the natural spider silk or natural protein. The elasticity could possible be increased up to 100%. The variants may also possess the properties of the above described fragments.

The fragment or variant may have substantially the same characteristics as the natural spider silk. The natural protein is particularly insoluble when in the fiber form and is resistant to degradation by most enzymes.

In the present invention, the isolated cDNA may code for spider silk proteins such as *Nephila clavipes* major ampullate (dragline) silk protein, *Nephila clavipes* minor ampullate silk protein, *Nephila clavipes* cocoon silk protein, *Areneus gemmoides* major ampullate silk protein, and *Areneus gemmoides* cocoon silk protein.

The invention is further directed to a replicable vector containing cDNA which codes for spider silk protein and which is capable of expressing spider silk protein.

The invention further relates to a transformed cell or microorganism containing cDNA or a vector which codes for spider silk protein or a fragment or variant thereof and which is capable of expressing spider silk protein.

The present invention is also directed to a new spider silk protein and a method for producing the protein which comprises culturing the transformed cell or microorganism described above under conditions which allow expression of the spider silk protein, optionally recovering the thus expressed spider silk protein and optionally purifying the recovered spider silk protein. The spider silk protein produced in this manner may be different from natural spider silk protein in that it may be free of other proteins or materials which occur in natural spider silk. The spider silk protein produced by recombinant techniques may also contain some small amounts of contaminating materials from the microorganism, cells and/or fermentation system in which it was produced. Thus, the present invention is also directed to these new or isolated proteins which are produced by recombinant DNA techniques.

The invention also relates to products such as fibers containing the recombinant protein of the invention either alone or in combination with other materials.

BRIEF DESCRIPTION OF THE DRAWINGS

The present invention will become more fully understood from the detailed description given hereinbelow, and the accompanying drawings which are given by way of illustration only, and thus are not limitative of the present invention, and wherein;

FIGS. 1A–1D show the FTIR Spectra of dragline silk fiber from the major ampullate gland of *Nephila clavipes* as a function of applied force with fiber axis perpendicular (1C and 1D) and parallel (1A and 1B) to the polarized radiation; 1A) and 1C): original spectra; 1B) and 1D): partially deconvoluted spectra of 1A) and 1C), respectively;

FIGS. 6A–D show the entire cDNA sequence and the corresponding amino acid sequence for spider Silk Protein 1 from the major ampullate gland of *Nephila clavipes*. The spider silk protein is encoded by the DNA through position 2154. Thus, the last amino acid is the Ser (amino acid 718) at positions 2152–2154. The cDNA sequence and the corresponding amino sequence are shown in SEQ. ID. NO. 1. The END codon TAG at positions 2155–2157 is not translated nor are the remaining codons; and FIGS. 7A–7D show the entire cDNA sequence and the corresponding amino acid sequence for spider Silk Protein 2 from the major ampullate gland of *Nephila clavipes*. The spider silk protein is encoded by the DNA through position 1785. The cDNA sequence and the corresponding amino acid sequence are shown in SEQ. ID. NO. 3.

DETAILED DESCRIPTION OF THE INVENTION

Figure 1C:
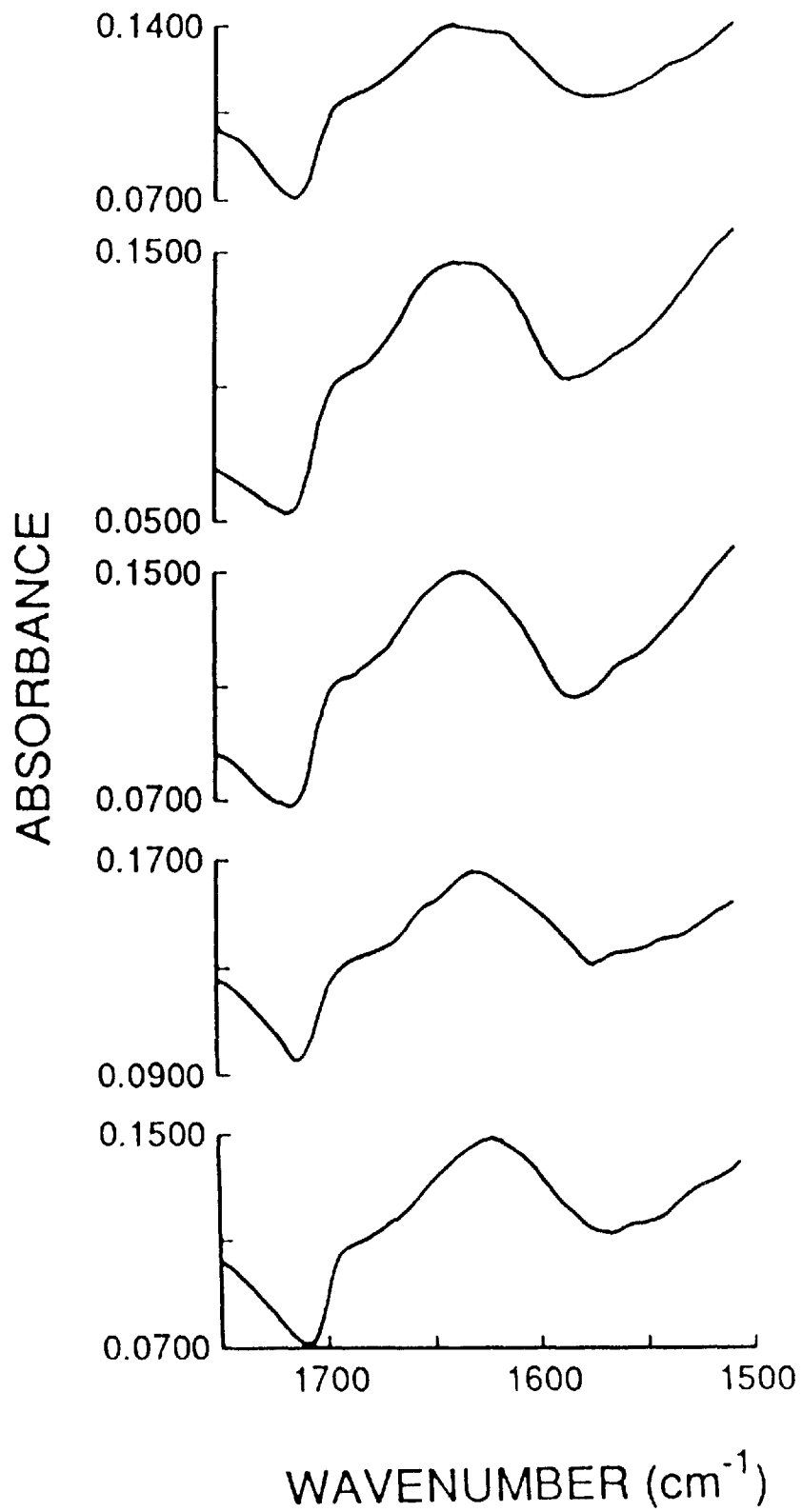

The genes for two different spider silk proteins, e.g., spider Silk Protein 1 and spider Silk Protein 2, have been cloned.

SILK PROTEIN 1

The cDNA codes for a spider silk protein comprising repeating units which contain a sequence which can be represented by the following general formula $$[(\alpha)(\beta)]_p \qquad (I)$$

wherein α is an amorphous region which can form an α-helix when stretched, β is a β-crystalline region and p is an integer of 1 to 100, preferably 15 to 50, more preferably 18 to 22 for fragments and 25 to 100, preferably 30 to 90 for the full length protein.

The α region is preferably an alanine rich region which contains 4 to 10 A's, preferably 5 to 8 A's and more preferably 6 or 7 A's. The α region contains at least 50% alanine, preferably at least 60% alanine, more preferably about 70–80% alanine and comprises about 35 to 50%, preferably 30 to 40% of the total protein based on the total number of amino acids. The α region may contain other amino acids such as glycine and/or serine.

The β region is any sequence which forms a β-crystalline structure or which forms β-pleated sheets. The β-region preferably comprises 40–70% of the total protein, more preferably 50–60% of the total protein. The above percentages (%) refer to % of amino acids. For each repeat "p" in the above formula, the α and β regions may be the same or different.

The cDNA codes for spider silk protein which comprises repeating units which can also be represented by the following general formula $$[(v)(\alpha)(\beta)]_p \qquad (II)$$

wherein α, β and p are as defined above, v is a variable region and wherein the variable region (v), if present, is a region containing 0 to about 12 amino acids which usually begins with the sequence AGR. A majority of the repeating units in the spider silk protein may contain these units as defined in this paragraph. Representative sequences falling within this formula are shown in Table 1 below (SEQ. ID. NO.:2, amino acids 1–644).

TABLE 1

```
|---v-----|---α-----|------β-------|

--------QGAGAAAAAA-GGAGQGGYGGLGGQG

--------------------AGQGGYGGLGGQG

------AGQGAGAAAAAAGGAGQGGYGGLGSQG

AGR---GGQGAGAAAAAA-GGAGQGGYGGLGSQG

AGRGGLGGQGAGAAAAAAGGAGQGGYGGLGNQG

AGR---GGQ--GAAAAAA-GGAGQGGYGGLGSQG

AGRGGLGGQGAGAAAAAA-GGAGQGGYGGLGGQG

--------------------AGQGGYGGLGSQG

AGRGGLGGQGAGAAAAAAGGAGQ---GGLGGQG
```

TABLE 1-continued

```
------AGQGAGASAAAA-GGAGQGGYGGLGSQG

AGR---GGEGAGAAAAAA-GGAGQGGYGGLGGQG

--------------------AGQGGYGGLGSQG

AGRGGLGGQGAGAAAA---GGAGQ---GGLGGQG

------AGQGAGAAAAAA-GGAGQGGYGGLGSQG

AGRGGLGGQGAGAVAAAAAGGAGQGGYGGLGSQG

AGR---GGQGAGAAAAAA-GGAGQRGYGGLGNQG

AGRGGLGGQGAGAAAAAAAGGAGQGGYGGLGNQG

AGR---GGQ--GAAAAA--GGAGQGGYGGLGSQG

AGR---GGQGAGAAAAAA-VGAGQEGIR---GQG

--------------------AGQGGYGGLGSQG

SGRGGLGGQGAGAAAAAA-GGAGQ---GGLGGQG

------AGQGAGAAAAAA-GGVRQGGYGGLGSQG

AGR---GGQGAGAAAAAA-GGAGQGGYGGLGGQG

VGRGGLGGQGAGAAAA---GGAGQGGYGGV-GSG

----------ASAASAAASRLSS
```

The isolated cDNA of the invention may code for a protein comprising repeating units which contain a sequence which can be represented by the following general formula $$--[(A)_m(X)_n]_p-- \quad (III)$$

wherein m is 4 to 10, preferably 5 to 8 and more preferably 6 or 7, n is 10 to 20, preferably 12 to 18 and more preferably 14 to 16, p is as defined above and each X, which may be the same or different, is selected from the group consisting of G, A, Q, Y and L, wherein at least 50% of the X's are G, more preferably at least 60% of the X's are G. For each repeat "p" in the above formula, each m and n may be the same or different.

At least 50% of the repeating units of the spider silk protein can be represented by the formula (I), (II) or (III), respectively, preferably at least 70% of the repeating units can be represented by the formula (I), (II) or (III).

The isolated cDNA of the invention contains repeating units which code for the sequence $$--[(A)_m GGAGQGGYGGLGGQG]--(SEQ.\ ID\ NO.\ 5) \quad (IV)$$

wherein m is 6 or 7.

The spider silk or fragment or variant thereof usually has a molecular weight of at least about 16,000 daltons, preferably 16,000 to 100,000 daltons, more preferably 50,000 to 80,000 daltons for fragments and greater than 100,000 but less than 300,000 daltons, preferably 120,000 to 300,000 daltons for the full length protein. The molecular weight of the spider silk protein shown in FIG. 6 and listed in SEQ. ID. NO. 2 is 64,492 daltons.

In the above formulas (I)–(IV), the protein may have additional amino acids or amino acid sequences inserted into the protein in the middle thereof or at the ends thereof so long as the protein possesses the desired physical characteristics. Likewise, some of the amino acids or amino acid sequences may be deleted from the protein so long as the protein possesses the desired physical characteristics. Amino acid substitutions may also be made in the sequences so long as the protein possesses the desired physical characteristics.

The major protein from *Nephila clavipes* dragline silk has been cloned. The sequence comprises a repeating hexamer of Gly-Gly-X-Gly-Y-Gly (SEQ. ID NO. 6), where X and Y are predominantly Gln and Ala but can be other amino acids. These repeats are separated by varying length amino acid inserts composed of Ala and Ser with small amounts of other amino acids possible. A representative sequence is as follows:

- [G-G-Q-G-A-G]-A-A-A-A-[G-G-A-G-Q-G]- G-Y-[G-G-V-G-S-G]-A-S-A-A-S-A-A-A-S- (SEQ ID NO. 6)

The protein of the invention is constituted primarily by repeats of the sequence

AGRGGXGGZGAG(A)$_{6-7}$GGAGQGGYGGLGGQG (SEQ ID NO. 7)

with X and Y being L, Y or Q but with X not the same amino acid as Z.

SILK PROTEIN 2

The cDNA codes for a spider silk protein comprising repeating units which contain a sequence which can be represented by the following general formula $$[(\beta)\ (\alpha)]_p \quad (I)$$

wherein α is an amorphous region which can form an α-helix when stretched, β is a linked β-turn region which forms a β-sheet like structure and p is an integer of 1 to 100, preferably 15 to 50, more preferably 18 to 22 for fragments and 25 to 100, preferably 30 to 90 for the full length protein.

The α region is preferably an alanine rich region which contains 4 to 10 A's, preferably 6 to 10 A's. The α region contains at least 50% alanine, preferably at least 60% alanine, more preferably about 70–100% alanine and comprises about 35 to 50%, preferably 30 to 40% of the total protein based on the total number of amino acids. The α region may contain other amino acids such as serine and/or glycine. Such substitutions may have no significant effect on function.

The β region is any sequence which forms a linked β-turn. The β-turn region is composed of repeats of GPGQQGPG-GYGPGQQGPSGPGS (SEQ. ID NO. 8) with occasional substitutions and one insert of GGY. The β-turn region has a much higher amount of proline than the β-crystalline region of silk protein 1. It is believed that the proline is responsible for causing the turns or "kinks" in the protein. Each β-turn will usually contain 1 proline, usually from 0 to 2 prolines. Each β-region will usually contain more than 1 β-turn, usually 4 or 5 β-turns. The β-region preferably comprises 40–70% of the total protein, more preferably 50–60% of the total protein. The above percentages (%) refer to % of amino acids. For each repeat "p" in the above formula, the α and β regions may be the same or different.

The cDNA codes for spider silk protein which comprises repeating units which can also be represented by the following general formula $$[(\beta)(\alpha)(v)]_p \quad (II)$$

wherein α, β and p are as defined above, v is a variable region and wherein the variable region (v), if present, is a region containing 0 to about 20 amino acids, usually 0 to about 18 amino acids, which usually contains the sequence GPGGY (SEQ. ID NO. 9) and/or GPGQQ (SEQ. ID NO. 10). A majority of the repeating units in the spider silk protein may contain these units as defined in this paragraph. Representative sequences falling within this formula are shown in Table 2 below, (SEQ. ID. NO.:4, amino acids 5–469).

protein possesses the desired physical characteristics. Amino acid substitutions may also be made in the sequences so long as the protein possesses the desired physical characteristics.

Abbreviations for amino acids used herein are conventionally defined as described hereinbelow unless otherwise indicated.

TABLE 2

```
|-----------β------------|------α---|--------v---------|

GPGQQGPGGYGPGQQGP--SGPGSAAAAAAAAAA----GPGGYGPGQQGPGGY

GPGQQGPGRYGPGQQGP---SGPGSAAAAAAA-------------GSGQQGPGGY

GPRQQGPGGYGQGQQGP--SGPGSAAAASAAASAESGQQGPGGYGPGQQGPGGY

GPGQQGPGGYGPGQQGP--SGPGSAAAAAAAS-----------GPGQQGPGGY

GPGQQGPGGYGPGQQGP--SGPGSAAAAAAAAS----------GPGQQGPGGY

GPGQQGPGGYGPGQQGL--SGPGSAAAAAAAA---------------------

GPGQQGPGGYGPGQQGP--SGPGSAAAAAAAAA-------------GPGGY

GPGQQGPGGYGPGQQGP--SGAGSAAAAAAA------------GPGQQGLGGY

GPGQQGPGGYGPGQQGPGGYGPGSASAAAAAA---------------------

GPGQQGPGGYGPGQQGP--SGPGSASAAAAAAAA-------------GPGGY

GPGQQGPGGYAPGQQGP--SGPGSASAAAAAAAA-------------GPGGY

GPGQQGPGGYAPGQQGP--SGPGSAAAAAAASA--------------GPGGY
```

The isolated cDNA of the invention may code for a protein comprising repeating units which contain a sequence which can be represented by the following general formula $$-[(A)_m(X)_n]_p-- \tag{III}$$

wherein m is 4 to 10, preferably 6 to 10, n is 10 to 20, preferably 12 to 18 and more preferably 14 to 16, p is as defined above and each X, which may be the same or different, is selected from the group consisting of P, G, A, Q, Y and L, wherein at least 50% of the X's are G, more preferably at least 60% of the X's are G. For each repeat "p" in the above formula, each m and n may be the same or different.

At least 50% of the repeating units of the spider silk protein can be represented by the formula (I), (II) or (III), respectively, preferably at least 70% of the repeating units can be represented by the formula (I), (II) or (III).

The isolated cDNA of the invention may contain repeating units which code for the sequence $$--[\beta(A)_m]-- \tag{IV}$$

wherein β is as defined above and m is 6 to 10.

The spider silk or fragment or variant thereof usually has a molecular weight of at least about 16,000 daltons, preferably 16,000 to 100,000 daltons, more preferably 50,000 to 80,000 daltons for fragments and greater than 100,000 but less than 300,000 daltons, preferably 120,000 to 300,000 daltons for the full length protein. The molecular weight of the spider Silk Protein 2 shown in FIG. 7 and listed in SEQ. ID. NO. 4 is 51,157 daltons.

In the above formulas (I)–(IV), the protein may have additional amino acids or amino acid sequences inserted into the protein in the middle thereof or at the ends thereof so long as the protein possesses the desired physical characteristics. Likewise, some of the amino acids or amino acid sequences may be deleted from the protein so long as the

| Amino Acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Recombinant spider silk protein can be recovered from cultures by lysing the cells to release spider silk protein which is present inside the cells. Initially, cell debris can be separated by centrifugation. The remaining debris and the supernatant are then repeatedly treated with solvents in which the cell debris are soluble but in which the spider silk protein is not soluble to thereby precipitate spider silk protein. These procedures can be repeated and combined with other procedures including filtration, dialysis and/or chromatography to obtain a pure product.

In accordance with degeneracy of genetic code, it is possible to substitute at least one base of the base sequence of a gene by another kind of base without causing the amino acid sequence of the polypeptide produced from the gene to be changed. Hence, the DNA of the present invention may also have any base sequence that has been changed by substitution in accordance with degeneracy of genetic code. For example, the amino acid sequence coded by a modified DNA corresponding to FIG. 6 obtained by the above-mentioned substitution is identical with the amino acid sequence of FIG. 6.

The DNA is readily modified by substitution, deletion or insertion of nucleotides, thereby resulting in novel DNA sequences encoding spider silk protein or its derivatives. These modified sequences are used to produce mutant spider silk protein and to directly express spider silk protein.

DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading phase.

Suitable host cells are prokaryotes, yeast or higher eukaryotic cells. Prokaryotes include gram negative or gram positive bacteria, for example *E. coli* or Bacilli. Higher eukaryotic cells include established cell lines of insect, spider or mammalian origin as described below.

Prokaryotic host-vector systems are preferred for the expression of spider silk protein. A plethora of suitable microbial vectors are available. Generally, a microbial vector will contain an origin of replication recognized by the intended host, a promoter which will function in the host and a phenotypic selection gene, for example, a gene encoding proteins conferring antibiotic resistance or supplying an auxotrophic requirement.

Vectors must contain a promoter which is recognized by the host organism. This is generally a promoter homologous to the intended host. Promoters most commonly used in recombinant DNA construction include the β-lactamase (penicillinase) and lactose promoter systems, a tryptophan (trp) promoter system and the tac promoter. While these are the most commonly used, other known microbial promoters are suitable. Details concerning their nucleotide sequences have been published, enabling a skilled worker operably to ligate them to DNA encoding spider silk protein in plasmid vectors and the DNA encoding spider silk protein. At the present time a preferred vector is pGEM3Z. Other possible expression vectors are λ GT11 and pGEM5Zft.

In addition to prokaryotes, eukaryotic microbes such as yeast cultures may be transformed with spider silk protein encoding vectors. *Saccharomyces cerevisiae*, or common baker's yeast, is the most commonly used among lower eukaryotic host microorganisms, although a number of other strains are commonly available. Yeast vectors generally will contain an origin of replication from the 2 micron yeast plasmid or an autonomously replicating sequence (ARS), a promoter, a DNA sequence coding for spider silk protein, sequences for polyadenylation and transcription termination and a selection gene.

Suitable promoting sequences in yeast vectors include the promoters for metallothionein, 3-phosphoglycerate kinase or other glycolytic enzymes.

Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes are also ligated into the expression vector 3' of the spider silk protein coding sequences to provide polyadenylation of the mRNA and termination.

In addition to microorganisms, cultures of cells derived from multicellular organisms may also be used as hosts. In principal, any higher eukaryotic cell culture is workable, whether from vertebrate or invertebrate culture. For example, an insect virus such as Baculovirus can be used to express silk protein in insect cells. However, interest has been greatest in vertebrate cells, and propagation of vertebrate cells in culture (tissue culture) has become a routine procedure in recent years. Examples of useful host cell lines are VERO and HeLa cells, Chinese hamster ovary (CHO) cell lines, and WI38, BHK, COS-7 and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and most preferably Simian Virus 40 (SV40). The early and late promoters are particularly useful because both are obtained easily from the virus as a fragment which also contains the SV40 viral origin of replication. Smaller or larger SV40 fragments may also be used, provided the approximately 250 bp sequence extending from the Hind III site toward the BglI site located in the viral origin of replication is included.

An origin of replication may be provided either by construction of the vector to include an exogenous origin, such as may be derived from SV40 or other viral (e.g., Polyoma, Adenovirus, VSV, or BPV) source, or may be provided by the host cell chromosomal replication mechanism. If the vector is integrated into the host cell chromosome, the latter is often sufficient.

The protein and DNA sequence of the major protein in dragline silk is described hereinbelow. The protein sequence comprises a repeating pattern which is divided into three segments. The first segment contains up to 9 amino acids. This sequence is AGRGGLGGQ (SEQ. ID NO. 11) but the segment can contain no amino acids or a combination of the first three with either of the second set of three. The second segment is composed of 9 or 10 amino acids with a sequence of GAGAAAAAA(A) (SEQ. ID NO. 12). This sequence is present in all repeats. The final segment is composed of 15 amino acids with a sequence of GGAGQGGYGGLG<u>G</u>QG (SEQ. ID NO. 13). The variability in this segment is at the underlined position which can also be S,N or A. This third segment is found in all repeats. In all of these segments there are rare substitutions of other amino acids but no pattern is seen nor are they present in more than 5% of the repeats sequenced.

The DNA sequence for this protein shows a very high preference for A or T in the third position of the codon. This is such that only about 10% of the codons end in G or C compared to an expected 50% if it is random. This is likely a stability factor for the DNA to prevent recombination and deletion events from occurring.

Spider dragline silk has a number of unusual properties. These include a tensile strength greater than steel or carbon fibers (200 ksi), elasticity as great as some nylon (35%), a stiffness as low as silk (0.6 msi), and the ability to super-contract in water (up to 60% decrease in length). These properties are unmatched by any other material. The new material of the invention would provide these features in a very low weight material. The cloned protein of the invention is the major component for this silk.

Spider silk, especially dragline silk, has a tensile strength of over 200 ksi and yet has an elasticity of nearly 35%. This combination results in it having the greatest energy input necessary to break any known fiber including Kelvar™ and steel. This combination is also unique in both biological and man-made materials. When spun into fibers, which can be done by dissolving spider silk in an appropriate solvent and forcing it through a small orifice, spider silk can have numerous uses. For example, one large volume use is for clothing. Silk with elasticity would have a unique place in the market even at high prices. It may also be applicable for certain kinds of high strength uses such as rope, surgical sutures, flexible tie downs for certain electrical components and even as a biomaterial for implantation (e.g., artificial ligaments or aortic banding). Thus, there are numerous applications for the invention including high-tech clothing, rope, sutures, medical coverings and others where various combinations of strength and elasticity are required. It is also possible to modify the properties of the silk fibers by altering the protein sequence.

The fibers may be used for the same uses as natural spider silk fibers. The fibers may also be mixed with various plastics and/or resins to prepare a fiber-reinforced plastic and/or resin product. Because spider silk is stable up to 100° C., the fibers may be used to reinforce thermal injected plastics.

The present invention is also directed to a method for preparing variants of natural spider silk protein which comprises determining the DNA sequence of a gene which codes for natural spider silk protein, preparing a variant of said DNA sequence, and expressing said variant of said DNA sequence in a cell or microorganism to produce a variant spider silk protein having properties different form the properties of natural spider silk. The variants of natural spider silk DNA may be prepared by identifying regions of said DNA of said gene which correspond to amorphous regions in said natural spider silk protein and modifying said DNA sequence corresponding to said amorphous region or regions to change the elasticity characteristics of the protein expressed by said variant DNA or identifying regions of said DNA of said gene which correspond to β-crystalline regions in said natural spider silk protein and modifying said DNA sequence corresponding to said β-crystalline region or regions to change the strength characteristics of said protein.

Based on the amino acid sequence of peptides derived from Nephila dragline silk, DNA probes are used to identify several clones from a silk gland cDNA library. More specifically, over 2kb of two separate clones have been sequenced in the manner described in Example 3 for the Nephila dragline silk protein. The largest of these clones (2.5kb) has been fully sequenced. The sequence contains the poly A site, 340 bases of the 3' untranslated region and the remainder a protein coding region. The protein region contains a basic 34 amino acid repeat. The repeat itself contains three regions. The first comprises 0–9 amino acids with a sequence of AGR(GGX)$_2$(SEQ. ID NO. 11). Clearly this region is not highly conserved. The second region has a sequence of GAG(A)$_x$ (SEQ. ID NO. 12) which is highly conserved in all repeats and is 8–10 amino acids long. The third segment is (GGX)$_5$ (SEQ. ID NO. 13) and is 15 amino acids long and is very highly conserved. In most cases, X is A, Q, Y or L. Clones for other silk proteins have been isolated and sequenced. In addition, the amino acid sequence from several spider silk proteins have been determined and these include: Nephila dragline (GYGPG (SEQ. ID NO. 14), GQGAG (SEQ. ID NO. 15), GAGQG (SEQ. ID NO. 16), GYGGLG (SEQ. ID NO. 17)) and cocoon (SAFQ) (SEQ. ID NO. 18) and Araneus dragline (GPYGPGQQGP) (SEQ. ID NO. 19) and cocoon (FLGG (SEQ. ID NO. 20), SVGLV-L/I -A-Y-A-L (SEQ. ID NO. 21)). Over 18 positive clones have been identified from a Nephila silk gland library using an 18 mer probe based on the dragline protein sequence.

In accordance with the invention, the recombinant protein can be made in bacteria, purified, if necessary, and spun into fibers. The optimum protein size for production may be determined so that the protein still retains the important physical properties.

The sequences of the spider silk protein repeats may vary in many ways and yet still be within the scope of the invention. For instance, Gln, Leu, and Tyr may be substituted for each other in the sequence. Moreover, the removal of poly-Ala segments results in a silk having a lower elasticity. Furthermore, additional variety in the protein sequence may result in replacing one Gly in each pair of Glys in the GGX with a Ser.

Accordingly, the silk protein of the invention can be varied depending upon its intended use. For example, when lower elasticity is desirable, the poly-Ala stretch of the protein sequence should be removed. In contrast, when a high degree of elasticity is desired, the length of the poly-Ala stretch should be increased. Also, if a less stiff silk is desired, glycine should be substituted with serine.

In accordance with the present invention, large quantities of protein having the desired properties can be obtained. This protein can be made into fibers for any intended use. Clones may also be sequenced for making minor ampullate, cocoon and swathing silks.

Mixed composites of fibers are also of interest due to their unique properties. Such mixed composites confer flexible behavior into otherwise stiff materials and would provide strength at the same time.

The following Examples are intended to illustrate the claimed invention and will enable others skilled in the art to understand the invention more completely. However, the invention should not be interpreted as being limited to only these representative Examples.

EXAMPLE 1

The major and minor silks from the spiders *Nephila clavipes* are harvested as described in Work, R. W., et al. *J. Arachnol.*, 10, 1–10 (1982), and then allowed to completely dry at room temperature. A length of 3–5 cm of silk is used for each FTIR experiment. Spectra are obtained with an Analect FX 6260 FTIR spectrometer through an Analect Micro-XA FTIR microscope at 2 cm$^{-1}$ resolution. Interferograms of 128 scans are routinely obtained and spectra are partially deconvoluted by the method of Kauppinen, J. K., et al., *Appl. Sectrosc.* 35, 271–276, (1986), employing Gaussian components with a half width at half height of 12 cm$^{-1}$ and a resolution enhancement factor (K) of 2. Axial extension experiments are carried out by fixing one end of the silk and attaching the other end to small suspended weights of the indicated size.

Before carrying out the actual experiments, the uniformity of the silk fiber is examined by taking FTIR spectra of several randomly selected sites along the fiber, both parallel and perpendicular to the polarized light. The spectra differed from each other by less than 2 cm$^{-1}$ in terms of peak positions (results not shown). Thus, the silk fiber is shown to be spectrally homogeneous.

Figure 1D:
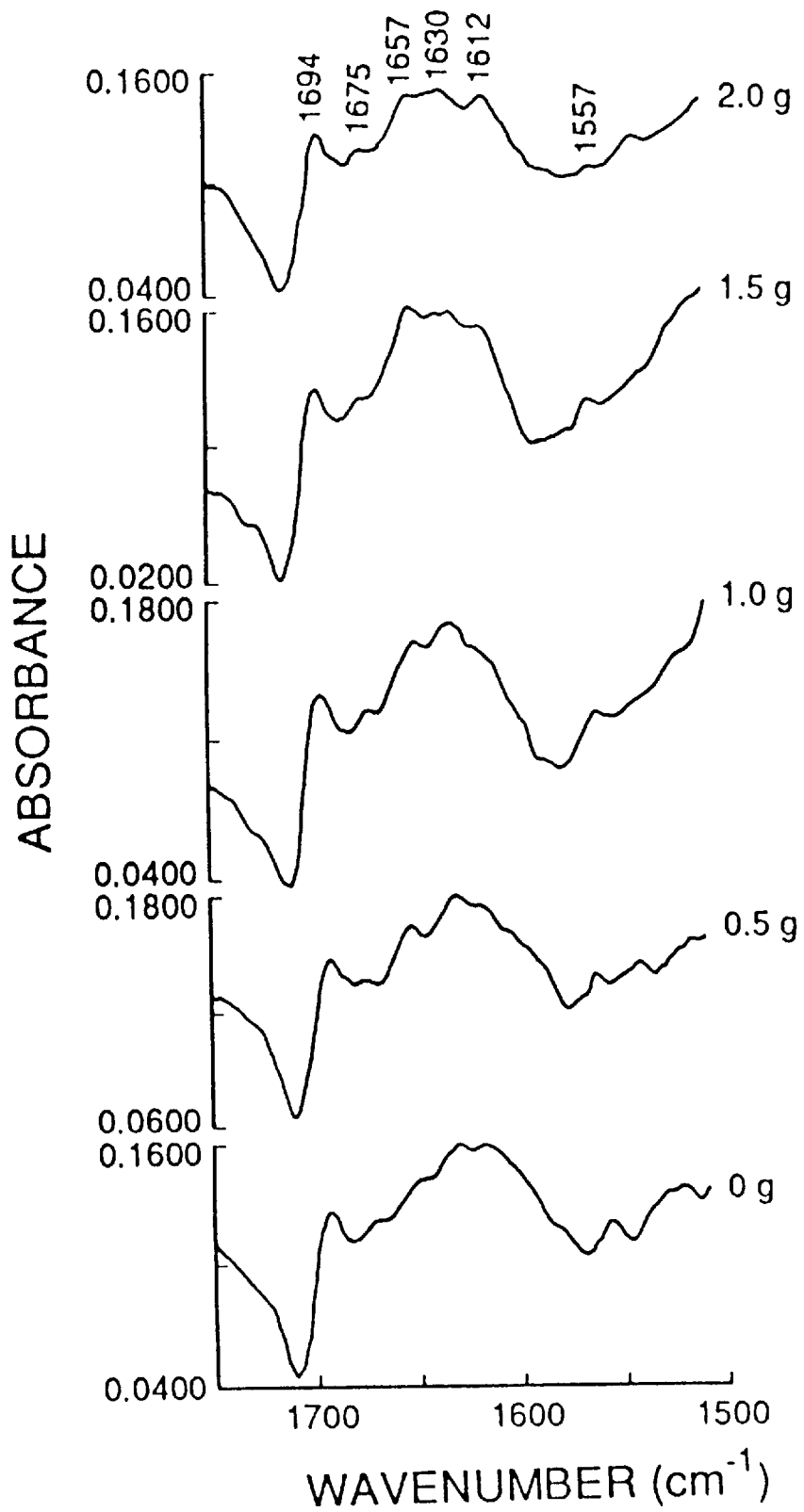

To examine the possibility of structural changes in major ampullate silk of the spider *Nephila clavipes* when the protein responds to axial strain, FTIR spectra of individual silk fibers are obtained through an infrared microscope. Original and partially deconvoluted infrared spectra of silk fibers, with the IR radiation polarized perpendicular to the fiber axis, are shown in FIG. 1C and FIG. 1D, respectively, as a function of axial tension on the fiber. Strong perpendicular dichroism in the amide 1 band is found for peaks at 1694, 1630 and 1620 cm$^{-1}$, consistent with the high content of β-structure previously detected in other forms of silk by IR spectroscopy, Suzuki, E. , *Spectrochim. Acta.,* 23A, 2303–2308 (1987); Fraser, R. D., et al., *Conformation in Fibrous Protein*, Academic Press, New York and London (1973). Weak bands at 1657 and 1675 cm$^{-1}$ are also evident and can be assigned to disordered regions and anti-parallel β-sheet respectively, Fraser, R. D. B., et al., *Conformation in Fibrous Protein*, Academic Press, New York and London (1973); Byler, D. M., *Biopolymers,* 25, 469–487 (1986). Amide II bands are seen at 1520 and 1550 cm$^{-1}$ indicating β-sheet and a very small amount of helical region respectively, Fraser, R. D. B. *Conformation in Fibrous Protein*, Academic Press, New York and London (1973); Cantor, C. R. et al, *Biophysical Chemistry*, Part II, 466–472, Freemnan, San Francisco (1980). When tension is applied to the silk fiber the radiation perpendicular to the fiber axis shows only minor changes in the Amide I region. In contrast, the peak near 1550 cm$^{-1}$ in the Amide II region decreases in intensity upon applied tension and shifts to 1557 cm$^{-1}$.

Figure 2A:
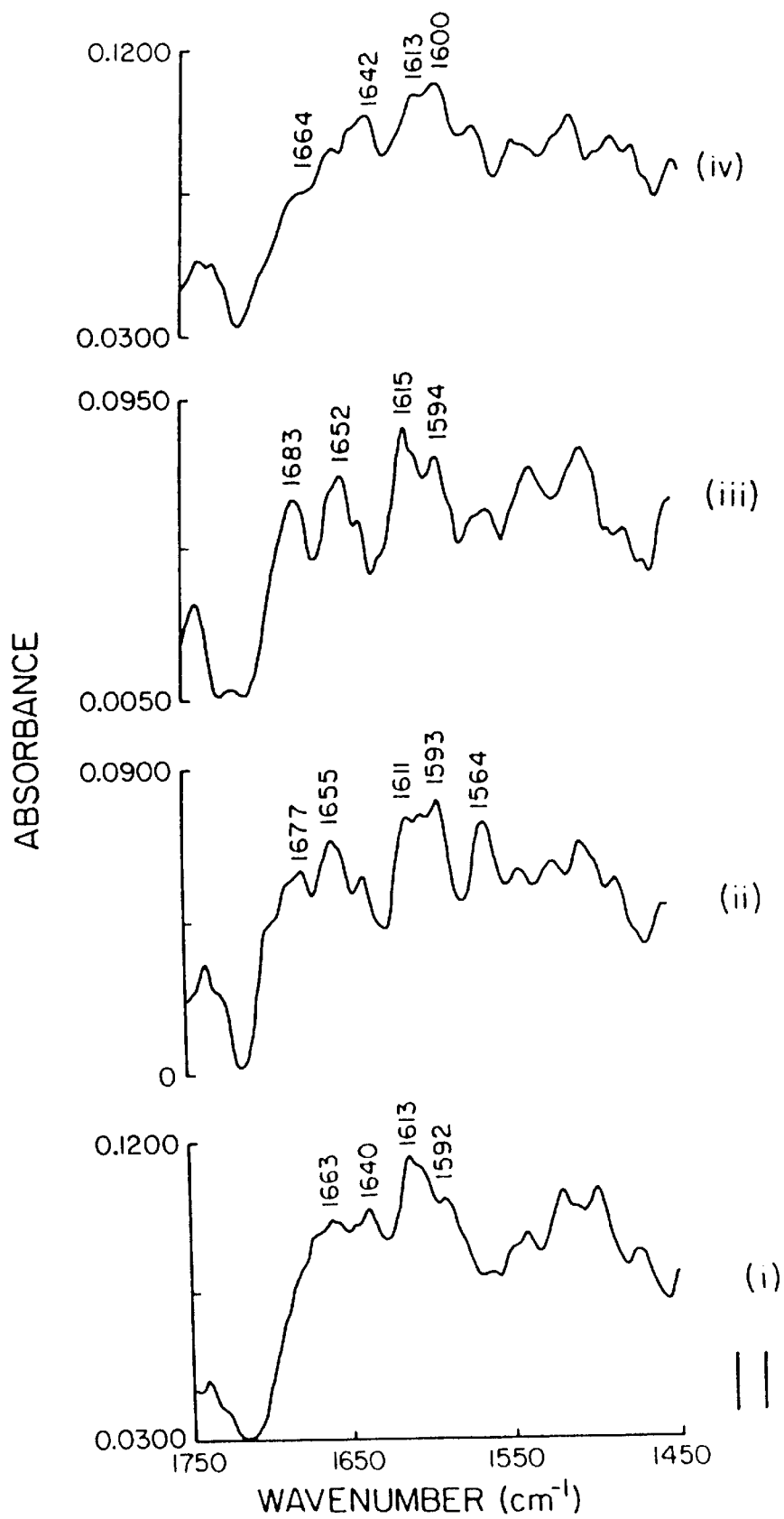
FIGS. 2A and 2B show the FTIR Spectra of dragline silk fiber from the major ampullate gland of *Nephila clavipes* with fiber axis parallel (2A) and perpendicular (2B) to the polarized radiation; (i): 0 gram axial tension; (ii): 2.0 gram axial tension; (iii): 29 min after release of the axial tension; (iv): 12 hrs after release of the axial tension.
Figure 2B:
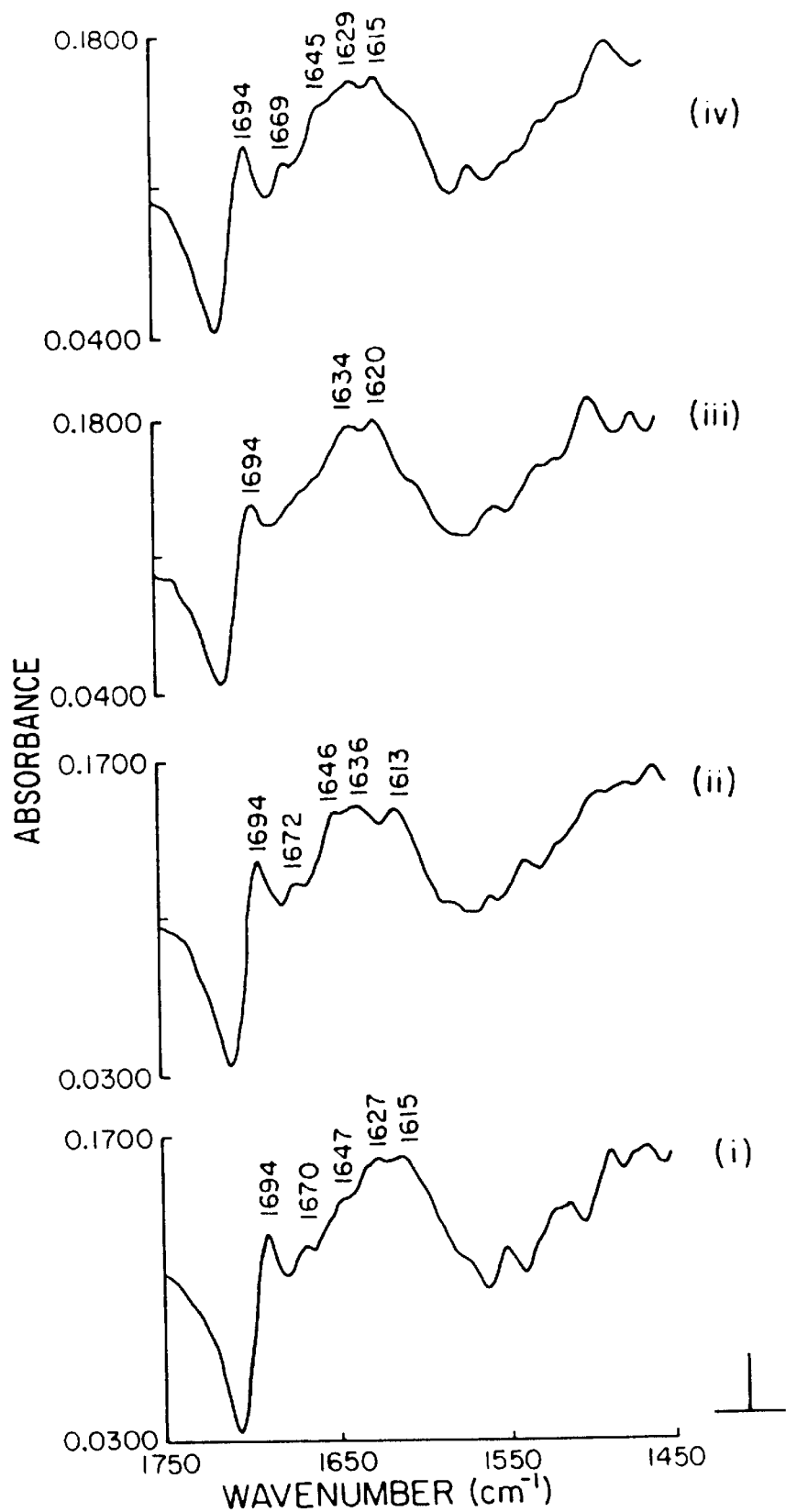
Figure 3A:
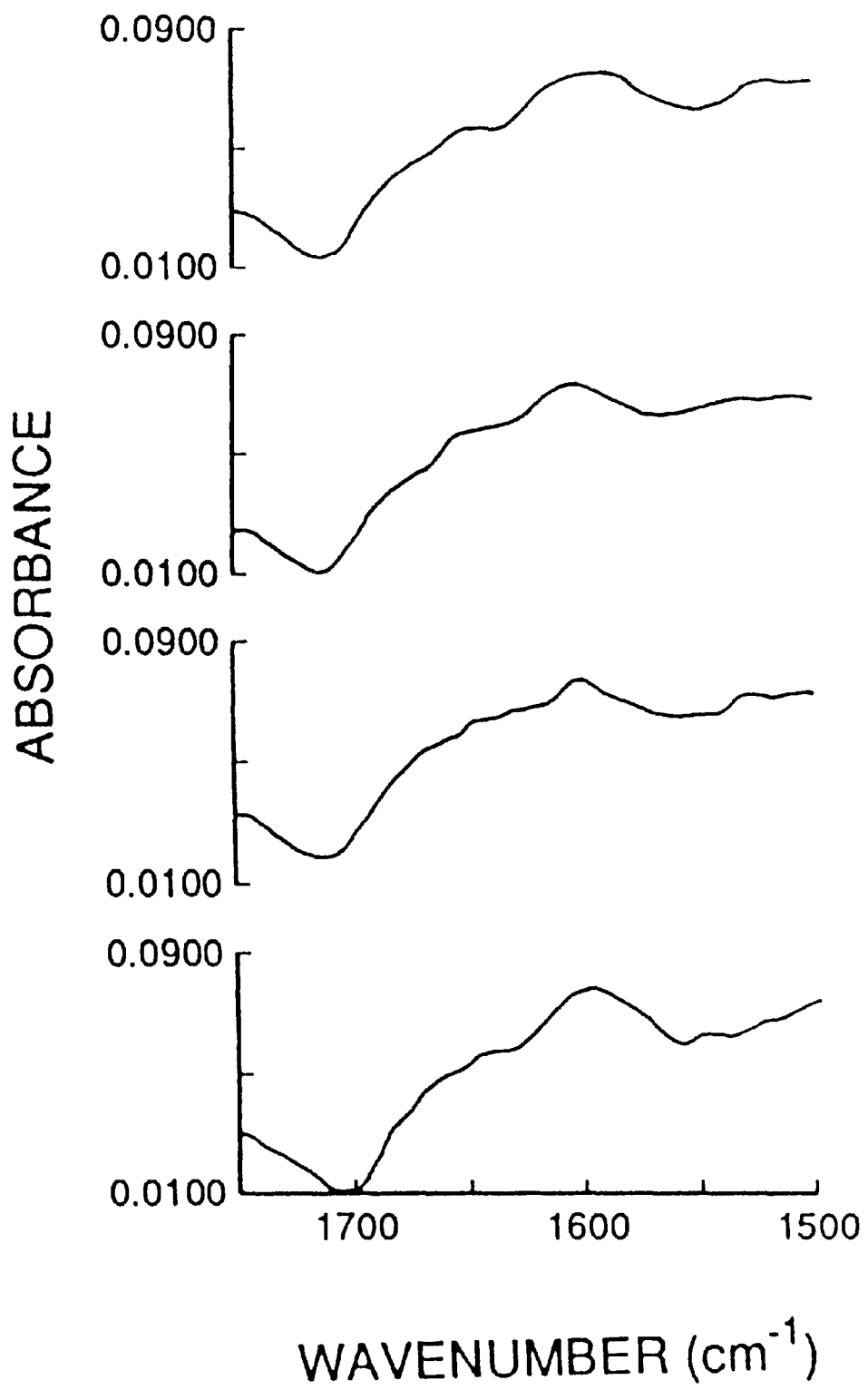
FIGS. 3A to 3D show the FTIR Spectra of dragline silk from the major ampullate gland of *Araneus gemmoides* as a function of applied force with fiber axis perpendicular (3C and 3D) and parallel (3A and 3B) to the polarized radiation; 3A) and 3C): original spectra; 3B) and 3D): partially deconvoluted spectra of 3A) and 3C), respectively.
Figure 3B:
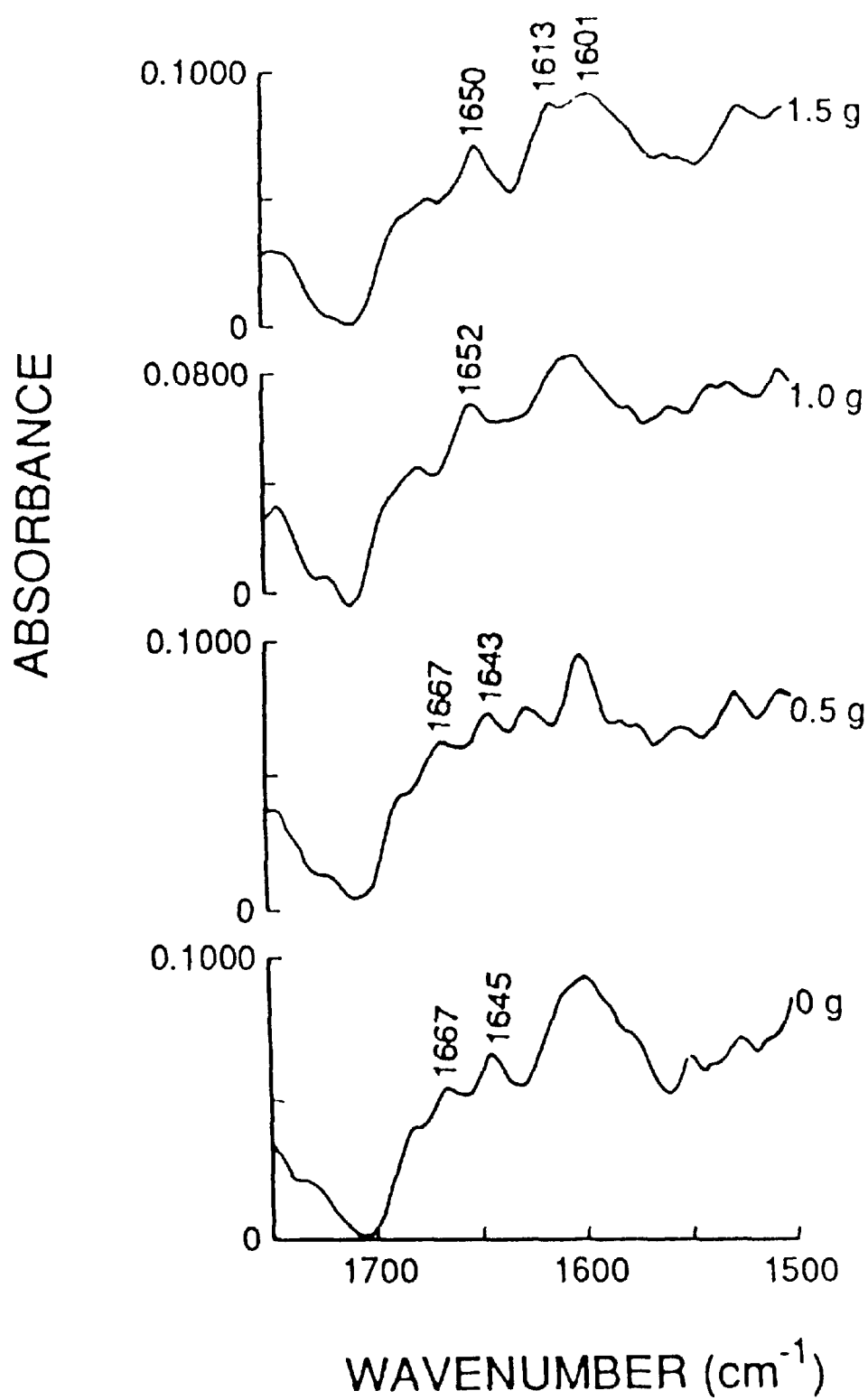
Figure 3C:
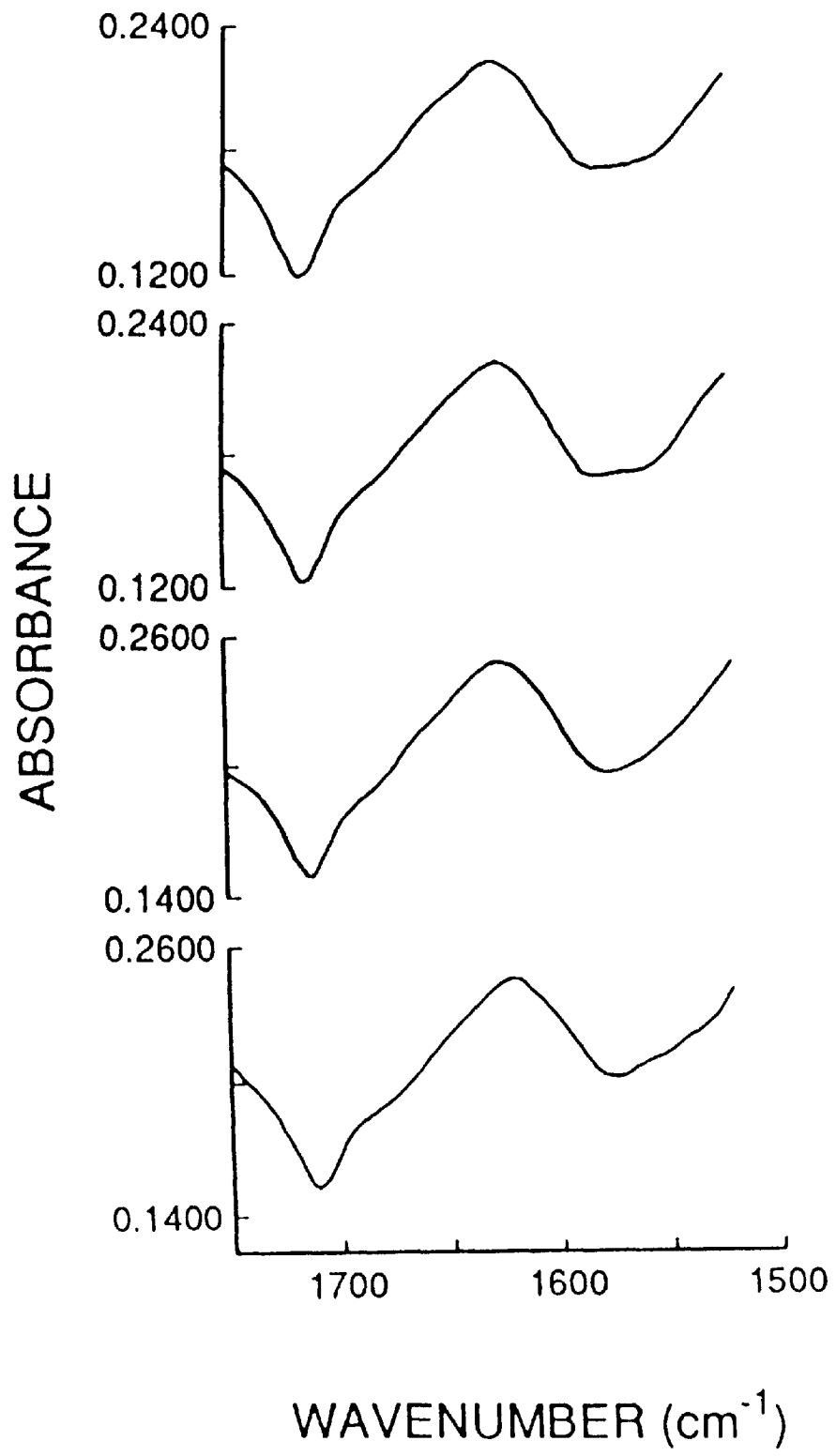
Figure 3D:
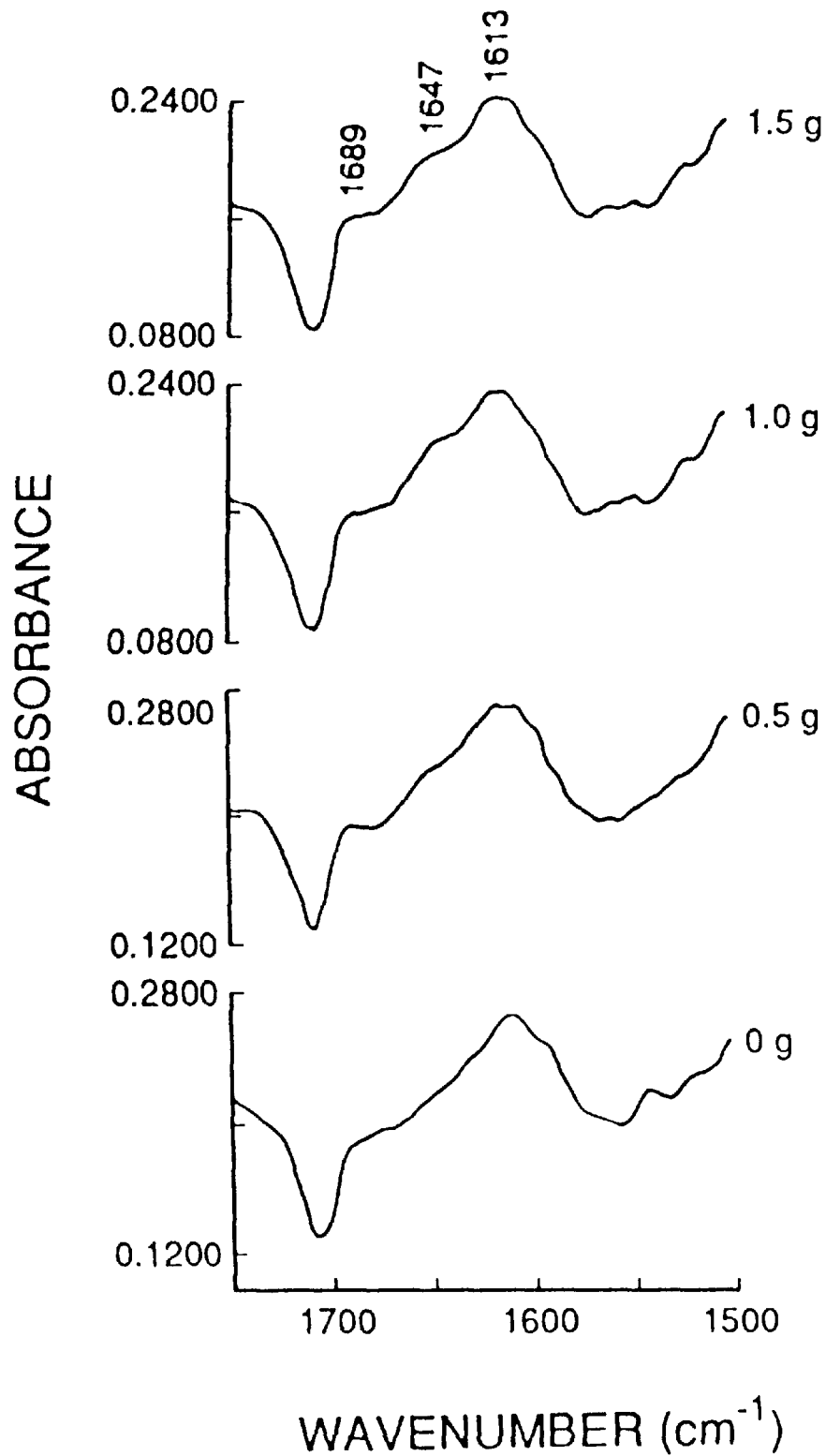

Strikingly different results are observed when the radiation is oriented parallel to the fiber axis (FIG. 1A and FIG. 1B). While all of the β-structure peaks are still clearly evident and their position unchanged, application of tension produces a dramatic increase in the absorbance at 1651 cm$^{-1}$. A peak in this region which displays parallel dichroism is strongly indicative of an α-helical structure, Fraser, R. D. B., et al., *Conformation in Fibrous Protein,* Academic Press, New York and London (1973); Byler, D. M., et al., *Biopolymers,* 25, 469–487 (1986). A similar increase is seen in the Amide II band at 1559 cm$^{-1}$ which also indicates the formation of helix. A band at 1512 cm$^{-1}$ is formed as well and splits into two components at 1508 and 1517 cm$^{-1}$ under tension. An absorbance in this region in proteins is usually assigned to either nonhydrogen-bonded peptide groups, Cantor, C. R., et al., *Biophysical Chemistry*, Part II, 466–472 (1980), Freemnan, San Francisco, or tyrosine residues, Fraser, R. D. B., et al. *Conformation in the Fibrous Protein*, Academic Press, New York and London (1973). The tyrosine content of this fiber is only 3–4%, so the latter assignment seems less likely, which also suggests a conformational change is induced by the tension. Additional confirmation that the observed changes are involved in the elastic behavior of drag-like silk comes from the complete return of the original spectra when tension is released. Two phases can be distinguished in the relaxation process (FIG. 2). During the first phase (0–1 hr after tension release) the spectra show the silk structure quickly but not completely returning toward its original form. In the second phase (1–12 hrs. after tension release) the relaxed silk gradually assumes the complete initial conformation.

EXAMPLE 2

Example 1 is repeated on silk from the major ampullate gland of another spider species *Araneus gemmoides* which is extracted in the same manner as described in Example 1. The spectra of a silk fiber with fiber axis perpendicular and parallel to the polarized light are shown in FIG. 3. As seen previously there is a peak around 1650 cm$^{-1}$ which appears as tension is applied and the silk fiber is parallel to the polarized incident radiation. Furthermore, in the parallel spectra of the major ampullate silks the peak around 1645 cm$^{-1}$ from unordered structure is replaced by an α-helical signal as axial tension is applied.

Figure 4:
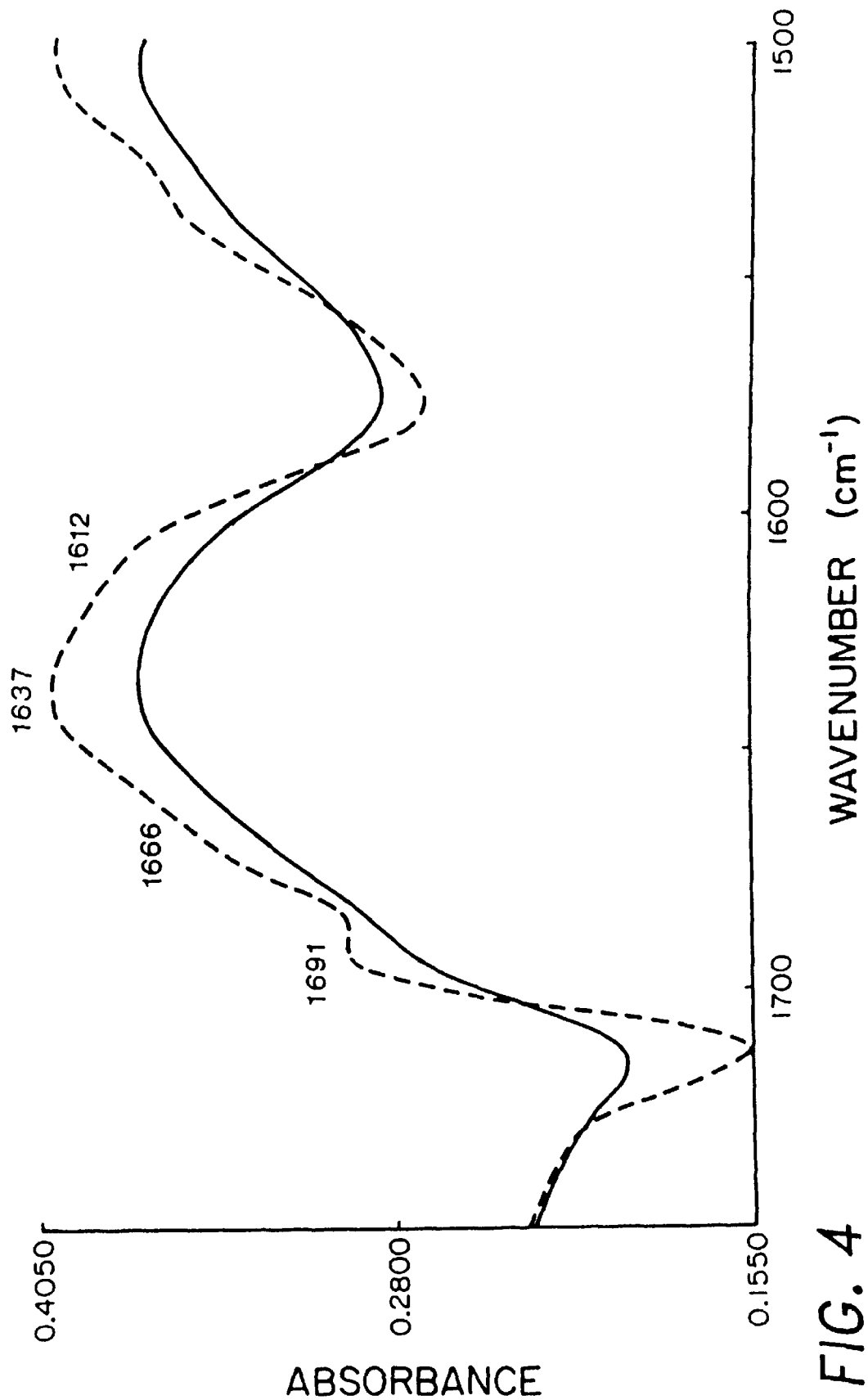
FIG. 4 shows the FTIR Spectra of 3 strands of dragline silk from the major ampullate gland of *Nephila clavipes* being oriented randomly on the sample plate and detected without polarizer; Solid line: original spectrum; Dashed line: partially deconvoluted spectrum.

To investigate the possibility that the α-helical structure formed by stretching originates from randomly oriented α-helices preexisting prior to applied tension and that the applied force merely reorients the helices into a parallel array, FTIR spectra of silk fiber are measured with unpolarized light. Several strands of silk are randomly oriented on the sample plate without applied tension and spectra are obtained. The result is shown in FIG. 4. No evidence for α-helix is found in these spectra as should be seen if preexisting α-helices are present in the relaxed state.

Figure 5A:
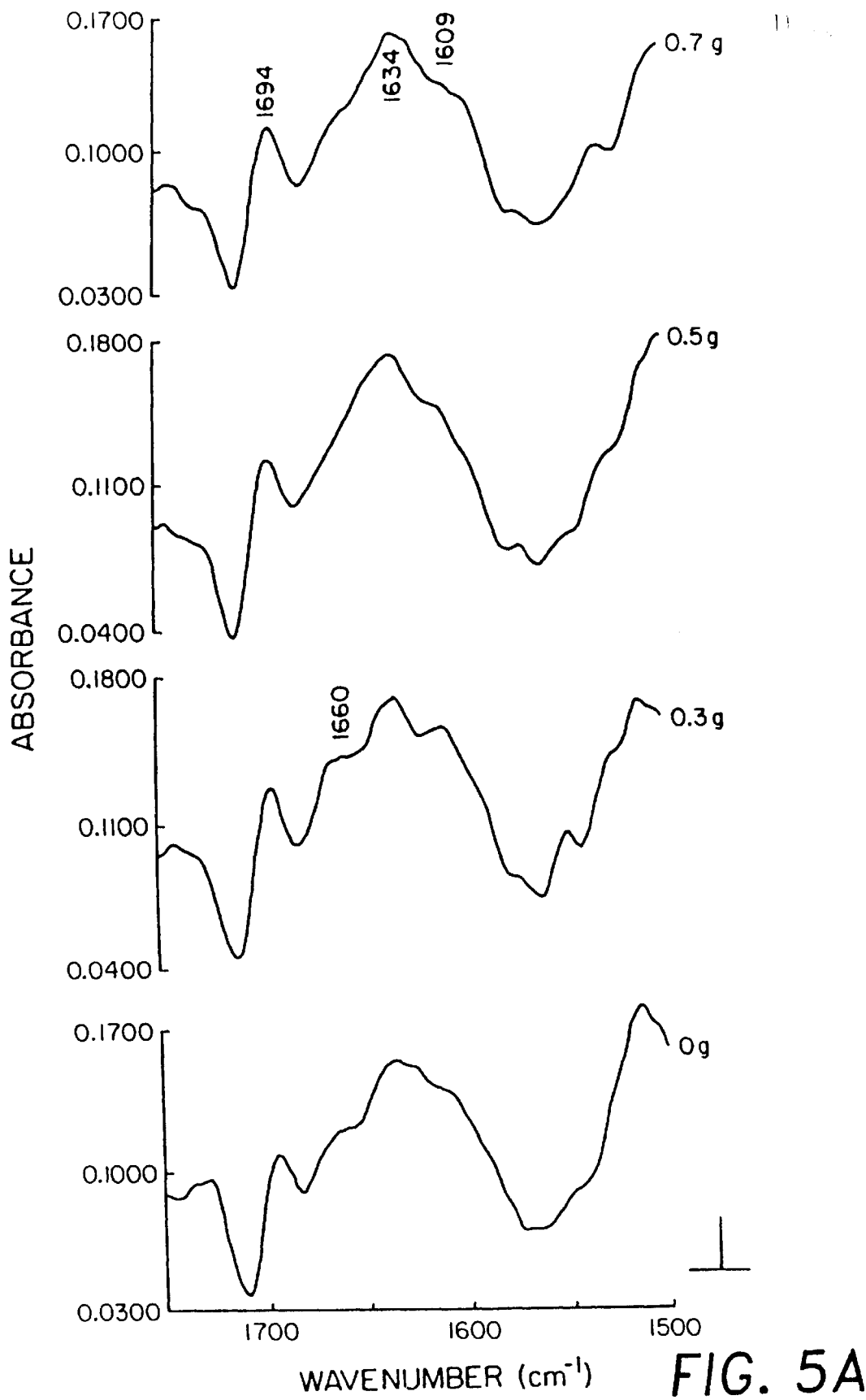
FIGS. 5A and 5B show the deconvoluted FTIR spectra of silk fiber from the minor ampullate gland of *Nephila clavipes*; 5A): fiber axis perpendicular to the polarized incident radiation; 5B): fiber axis parallel to the polarized incident radiation.
Figure 5B:
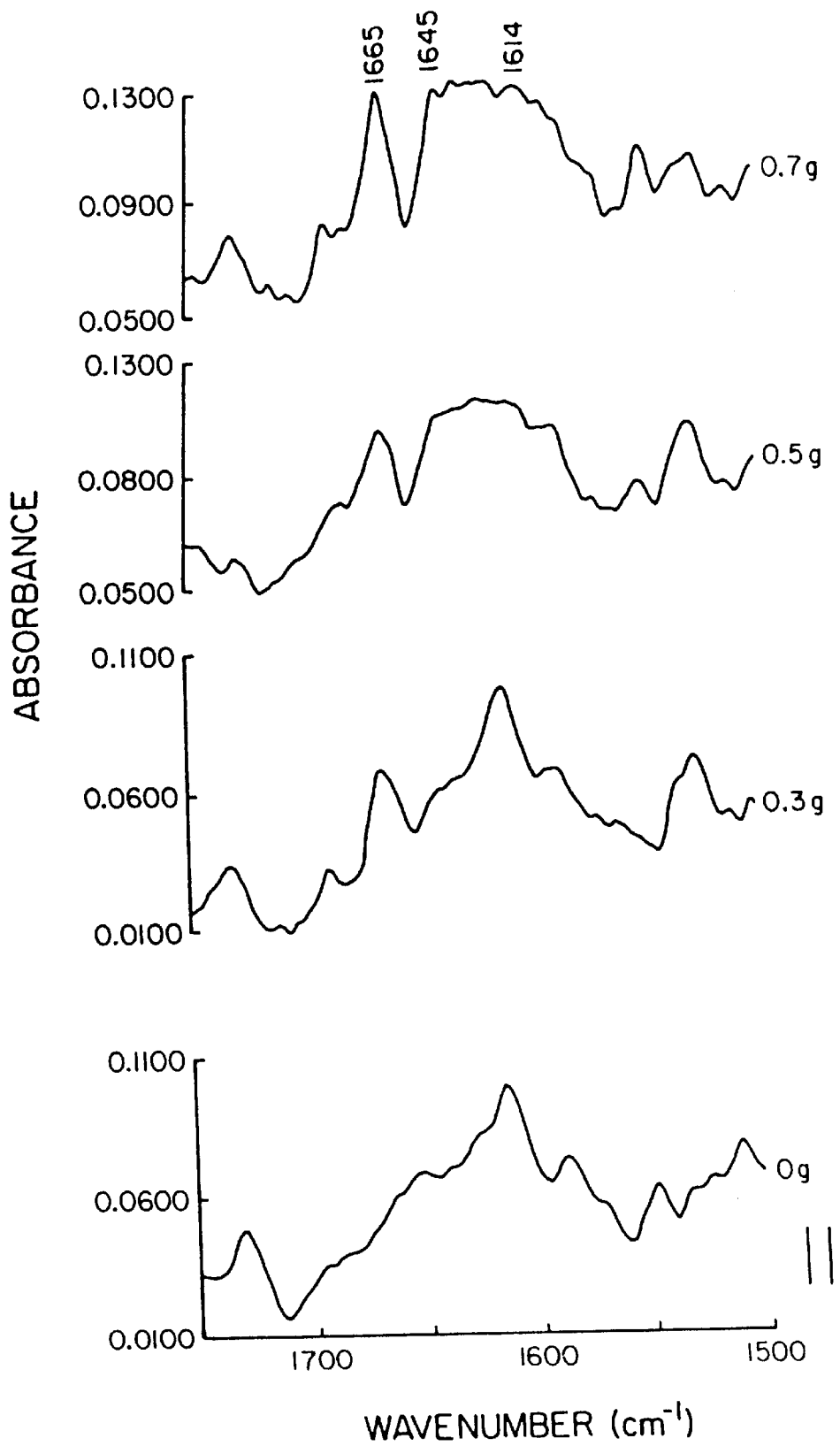

An additional test of this hypothesis is performed by examining the spectra of silk fibers from the minor ampullate gland. The silk produced form the minor ampullate is distinct from that of the major gland in terms of amino acid composition, function and mechanical properties, Anderson, S. O. *Comp. Biochem. Physiol.,* 35, 705–711 (1970); Work, R. W., et al., *J. Arachnol.,* 15, 65–80 (1987); Work, R. W., *Text. Res. J.,* 47: 650–662 (1977); Tillinghast, E. K., et al., *Ecophsiol. of Spiders,* 203–210 (1987), Springer, Heideberg). In particular, this silk is significantly less elastic and has a lower tensile strength than that of major ampullate gland silk, Work, R. W., *J. Text Res.* 47: 650–662 (1977); Lucase, F., et al., *J. Text Res.,* 46: T440–T452 (1955). Therefore, the two different types of silk fibers are compared in terms of conformational features and molecular responses to tension employing FTIR. The spectra of silk from the minor ampullate gland with its fiber axis perpendicular and parallel to incident polarized infrared radiation are shown in FIG. 5. The spectra of major and minor ampullate silks with the fiber axis parallel to the polarized light are very different. Of particular interest is the observation that no evidence of α-helical formation can be detected in the spectra of the less elastic silk when tension is applied. Instead, a peak at 1665 cm$^{-1}$ appears which suggests an increase in turns in minor ampullate silk upon the very limited stretching which occurs.

The structural basis of spider silk elasticity is also examined by obtaining partial primary structure information. The dragline silk proteins from both *Nephila clavipes* and *Araneus gemmoides* are partially digested by limited acid hydrolysis, the resulting peptides are isolated by reversed-phase HPLC and sequenced by gas phase Edman-degradation, Hewick, R. M., et al., *J. Biol. Chem.,* 256, 7990–7997 (1981). Peptides with a sequence of GQGAG and GAGQG are found to be the most common with a peptide of sequence GYGGLG nearly as common in *Nephila clavipes*. Based on analogy with *Bombyx mori* fibroin, the peptides containing alternating glycine residues presumably form the β-sheet regions, Lucas, F., et al., *Comprehensive Biochem.,* 26B, 475–558 (1968). Partial sequencing of *Araneus gemmoides* reveal the Gly-rich repetitive peptides which have high propensity to form β-sheet as well. Most intriguingly, tri- and tetra- peptides containing primarily alanine residues are also observed in both species, suggesting that they are most likely present in more irregular conformations in the amorphous regions.

The combination of FTIR and peptide sequencing suggests a molecular mechanism for the elasticity of spider silk. The simplest interpretation of the FTIR results is that tension along the fiber leads to the formation of helices (probably of the alpha type). Sequencing of spider silk peptides demonstrates the similarity to other forms of silk with alternating glycine residues in β-sheet regions. There are also other structurally less well defined regions, which in the particular case of spider silk appear to be alanine rich. Short polypeptides rich in alanine have a strong tendency to form α-helices, Yang, D. S. C., et al., *Nature*, 333, 232–237 (1988). It has also been shown that stretching fibers of polyalanine leads to the formation of a regular α-helical structure, Bamford, C. H., et al., *Nature*, 173, 27–31 (1954). Recently, short alanine-based peptides are found to have the propensity to form unusually stable α-helical structure and individual alanine residues are thought to possess high helical potential, Marqusees, et al., *Proc. Natl. Acad. Sci. USA*, 86, 5286–5290 (1989). Thus, the alanine rich segments in the amorphous regions of major ampullate dragline silk are very likely to be the source of the observed tension induced formation of α-helix.

Major ampullate spider silk can be most simply pictured as semicrystalline regions of interlocking β-sheets which give the fiber its remarkable strength. These regions appear to change little when force is applied along the fiber axis. The β-sheet portions of individual polypeptide chains are interspersed with short, alanine-rich domains which are disordered when the fiber is in a relaxed state. Application of tension induces these regions to become helical with the energy for helix formation arising at least partially from the applied mechanical forces. This force-induced formation of ordered structure is a unique finding and may be of general relevance to other biochemical systems. This clearly contrasts with the α to β transformation seen upon stretching in some other silks, (Lucase, F., et al., *Comprehensive Biochem.*, 26B, 475–558 (1968). When tension is relaxed the ordered regions are then entropically driven back to a more disordered state producing the observed elasticity.

EXAMPLE 3

1. Purification and identification of silk proteins

The spiders in this research are *Nephila clavipes* purchased from Marine Specimens Ltd., Florida. The first step to be taken is to obtain pure silk from a single type of silk gland. Using the method described by Work et al., *J. Arachrol.*, 10, 1–10, (1982), an apparatus was designed to draw a single silk fiber from one spinnerette of the spider. The single silk fiber is stuck on a spool. A variable speed electrical drill is then used to forcibly remove 0.5–1 mg of pure silk from the spinnerette. The pure silk is dissolved in 5M LiSCN, TFA (trifluoroacetic acid) 100% at room temperature and then is run on reverse phase HPLC (high performance liquid chromatography), using a C-18 column with buffer A containing 0.4M acetic acid/pyridine, pH 4.0 and buffer B which consists of buffer A containing 40% propanol. Two peaks of peptide are observed by fluorescence.

2. Amino acid composition of the protein(s)

The pure silk is hydrolyzed in 6N HCl for 35 min at 155° C. under vacuum to prevent oxidation. After drying and removal of HCl, the sample is analyzed by the OPA (O-phthalaldehyde) (Jones, et al., *J. Lig. Chromat.*, 4, 565–586 (1985) and the PITC (phenyl isothiocyanate) (Heinrickson, R. L., et al. *Anal. Biochem.*, 136, 65–74 (1984) methods with HPLC on a C-18 reverse-phase column.

3. Protein cleavage and fragment purification

The preliminary results show a "ragged" amino terminus of the whole silk protein. Thus, either the proteins in the silk do not have the same sequences or their N-terminal sequences do not start at the same place. Protein cleavage and fragment purification are conducted to provide the fragments of silk protein for partial sequencing. The fragments are cleaved by 6M HCl hydrolyzing under a temperature of 155° C. for 3 min. The fragments are purified by running on HPLC using a C-18 reverse-phase column.

| Time speed | Volume of B-buffer % | Record |
|---|---|---|
| 0 min | 0 | 10 cm/60 |
| 20 min | 6.6 | |
| 40 min volume | 13.2 | flow |
| 60 min ml/min | 19.8 | 0.75 |
| 80 min | 33.3 | |
| 100 min | 50 | |
| 120 min | 66.6 | |
| 140 min | 100 | |

4. Partial amino acid sequencing of protein

The pure fragments are sequenced by an Applied Biosystem gas phase protein sequencer (470A) based on an amino acid analysis of the fragments, which provides the information to determine if the fragments could represent a suitable sequence for a DNA probe such as GQGAG (SEQ. ID NO. 15), GAGQG (SEQ. ID NO. 16) or GYGGLG (SEQ. ID NO. 17).

5. Construction of synthetic DNA probe

Synthesis of synthetic DNA probes is conducted using an automated Applied Biosystems DNA synthesizer (430A). The product DNA can be utilized as the hybridization probes. Since glycine and alanine are the major components of the protein, using four different codons for these amino acids at the third position increases the possibility of matching the most frequent codon on these fragments.

5' CCnCGnCCnGT(C or T)CC3' (SEQ. ID NO. 22)

n=ACGT, four different bases.

6. Cloning cDNA from silk gland mRNA

In order to obtain mRNA from silk glands, the spiders are forcibly silked to stimulate mRNA synthesis, Canceles, G. C., et al.,*J. Exp. Zoo.*, 216, 1–6 (1981). The major ampullate silk glands are dissected from the abdomen of the spiders (picture of anatomical location of the silk glands is from the book, Foelix, F. R., *Biology of Spider*) and immersed in liquid nitrogen immediately. After adding a small amount of liquid nitrogen and silk glands into a pestle and mortar, the glands are ground to powder. RNA is extracted by the SDS hot phenol method, Taylor, D. W., et al., *Mol. Biochem. Parasitol*, 10, 305–318 (1984). An oligo dT column is used to isolate the mRNA from the total RNA, Haim Aviv et al., *PNAS*, 69; 1408–1412 (1972).

The reverse transcription of the mRNA to cDNA is done using the RiboClone™ cDNA Synthesis System from Promega (Technical Manual). The RiboClone™ system is a kit for efficient, complete synthesis of double-stranded cDNA from poly(A) + mRNA starting material. After making cDNA, the radioactively labeled cDNA is run through a Sepharose™ 4B (Pharmacia) gel filtration column to separate large fragments from small fragments. cDNA's larger than 500 bp are ligated into the vectors and transformed into XL1-blue™ E. coli (Stratagene) to construct a cDNA library (Maniatis, T., et al., Molecular Cloning, A Lab Manual (1982)).

The pBluescriptSK plasmids which have the function of producing single strand DNA under the trigger of helper phages (Manual from Stratagene) are used as the vectors to clone the cDNA. The Bluescript™ SK and XL1-Blue™ system provides a convenient host-vector system for cloning cDNA. The vector contains T7 and T3 promoters flanking a polylinker for convenient in vitro synthesis of RNA from cloned cDNA. Also, the polylinker is positioned so that insertion of a cloned DNA interrupts a lacI gene, providing a method for color selection of clones containing inserts. Furthermore, the plasmids can be rescued as bacteriophage containing a single-stranded DNA. The XL1-Blue™ strain is an appropriate E. coli host cell. The Bluescript™ SK (Stratagene) plasmids from Stratagene have been large scale produced (Large prep using the Triton lysis method, Frederick M. Ausubel, et al., Current Protocols in Molecular Biology, Volume 1, 1987), lysozyme incubation time was 20 min at 37° C. and purified by CsCl gradient in an ultracentrifuge (L7–55, Beckman) (Frederick M. Ausubel, et al., Current Protocols in Molecular Biology, Volume 1, 1987, published by Greene Publishing Associates and Wiley-Interscience) using vti80 rotor at 24° C., 54,000 rpm overnight. Further plasmids clean-up is done by SDS sucrose gradient, Maniatis, T., et al., Molecular Cloning, A Lab Manual (1982)., published by Cold Spring Harbor.

The Bluescript™ SK plasmids are cut by restriction enzyme Sma1 to create a blunt end. In order to reduce the self-ligation rate of the plasmids, alkaline phosphatase from calf intestine (CIP) (Mannheim Boehringer) is used to remove the phosphate at the 5-end of the plasmids (Maniatis, T., et al., Molecular Cloning, A Lab Manual (1982) published by Cold Spring Harbor). Deactivation of CIP was conducted at 75° C. instead of 68° C. for 30 min. and Elutip-d™ column (Schleicher and Schuell, Manufacturer, Manual for purification of DNA) was used to purify and clear the vectors. Elutip-d™ columns are pre-poured ion exchange columns containing a matrix similar to RPC-5.

Ligation of cDNA with Bluescript™SK is carried out at 4° C. overnight by T4 DNA ligase (Maniatis, T., et al., Molecular Cloning, A Lab Manual (1982), published by Cold Spring Harbor) then transformed into competent XL-1 blue E. coli. The bacteria are inoculated overnight in 1X YT and grown up to $OD_{600}$ 0.3–0.6. The bacteria are spun down in a JA 20 rotor at 5000 rpm for 5 min, then resuspended in ½ the original volume of 50 mM $CaCl_2$+10mM Tris, pH 8. The solution is iced for 20 min. and the cells are spun down the same as before and resuspended in 1/20–1/50 of the original volume of 50 mM $CaCl_2$. Aliquot in 0.3 ml. Add DNA to the appropriate tubes. Ice for 60 min. and heat shock for 3 min. at 45° C. Spread the plates and incubate for overnight at 37° C. The colonies of bacterial cells with the plasmid which has ampicillin resistance markers survive in the YT agar plates with ampicillin.

7. Synthetic oligodeoxynucleotide to screen the cDNA library

The synthetic oligodeoxynucleotide probes are labeled with $p^{32}$ by T4 polynucleotide kinase (Maniatis, T., et al., Molecular Cloning, A Lab Manual (1982), published by Cold Spring Harbor). The white colonies from the plates were transferred to 96 well assay plates with YT medium with ampicillin and grown again at 37° C. overnight. Then the bacteria with plasmid are transferred to Hybond-N™ hybridization transfer membranes (Amersham) using a 32 pin stamp and allowed to grow overnight in ampicillin plates. The 32 pin stamp is a homemade stamp consisting of pins inserted into a styrofoam block to match to wells of the 96 well plate. Then plasmid numbers are amplified on chloramphenicol plates. NaOH was used to lyse the bacteria and the DNA on the membranes was fixed by baking in an oven with a vacuum at 80° C. for 2 Hr (Maniatis, T., et al., Molecular Cloning, a lab manual (1982), published by Cold Spring Harbor).

The libraries were screened by a radioactively labeled oligodeoxynucleotide probe using the method of Wood and Lawn because of the highly complex DNA structure, Wood, W. I., et al., PNAS, 82, 1585–1588 (1985).

8. Applying Southern transfer and hybridization of the DNA to confirm positive colonies from the first screening.

Positive colonies are picked and the grown in YT medium and the plasmid DNA with inserts are extracted by mini preparation. (Promega Catalog and Frederick M. Ausubel, et al., Current Protocols in Molecular Biology, Volume 1, 1987). After running the DNA in the agarose gel, the samples are blotted onto Hybond-N™ membranes (Maniatis, T., et al., Molecular Cloning, A Lab Manual (1982), published by Cold Spring Harbor) and hybridized again by the same probes as above, Wood, W. I., et al., PNAS, 82, 1585–1588, (1985).

9. Restriction enzyme digestion DNA of the positive colonies.

Since there was more than one colony showing positive by the probe hybridization, restriction enzymes including BamHl, Ecor1, Pst1, Hae3, Apal, Clal, Hinc2, Hind3, Kpn1, Sal1, Sal2, Xho1, Ssp1 and Sph1 are applied (Digestion conditions for each enzyme according to the manufacturer instruction) to detect the differences between these positive colonies as well as to obtain information for further DNA sequencing analysis.

10. Subcloning the restriction enzyme digested fragments and screening by the probe.

In order to avoid wasting time on sequencing of suspicious colonies, the fragments digested by Hae III and Pst1 were filled by four different dNTP ACGT using a Klenow fragment of E. coli DNA polymerase (Maniatis, T., et al., Molecular Cloning, A Lab Manual (1982)) to create blunt-end fragments. Then the fragments were randomly subcloned into an M13 phage by the same procedure as cloning. The plaques were screened again by the probes (as above). The positive plaques were probed again by southern hybridization, Wood, W. I., et al., PNAS, 82, 1585–1588, (1985).

11. Sequencing the positive subclone fragments.

Positive plaques of M13 phages with inserts were cultured at 37° C. with BSJ 72 E. coli overnight to produce single strand DNA for DNA sequencing. For purification of single strand DNA, 1 ml phage containing the supernatant mix with 0.25 ml RNAase/PEG(PEG 10%, NaCl 2.5M, EDTA 0.015M) standing for 2–3 hr. at room temperature. Spin 5 min. in microfuge to pellet phage. Remove solution as much as possible. Dissolve the pellet in 0.07 ml proteinase solution (0.01M Tris pH8, 0.001M EDTA pH8, 0.2% Sarkosyl, 0.07 mg/ml Proteinase K), incubation 20 min. at 55° C., add 0.05 ml 0.25M NaCl. Extract with 0.15 ml water saturated Phenol, extract with 0.130 ml Phenol/CHCl/Isoamyl Alcohol (50/45/5%), then extract with 0.120 ml CHCl. Precipitate with 0.2 ml EtOH at −80° C. more than 20 min. or −20° C. more than 1 hr. Spin 15 min. then wash the pellet with 70% EtOH, dry pellet and resuspend in 40 ml H$_2$O. After purification of single strand DNA, the universal primer for an M13 phage was used to hybridize the template and the DNA was sequenced based on the method of, Sanger, F., et al., *PNAS*, 74: 5463–5467 (1977). S$^{35}$-dATP was used as labelling for an exposure picture of the sequencing. The apparatus of Sequencing Gel Electrophoresis System (Model S2) (obtained from BRL, Bethesda Research Laboratories Life Technologies, Inc.) is operated in accordance with the manufacturer's instructions. Running condition: 70 Watts Time: 3–7 hours.

The larger gel plate is siliconized. The glass is then baked 4 hours at 90° C., only when the glass is new or washed by NaOH. Each time the larger plate was siliconized without baking before using.

The smaller plate is treated with 2 ml of a 2% solution in ethanol of 3-Methacryloxypropyl-trimethoxysilan(Sigma) each time before using. Both larger and smaller plates were thoroughly cleaned with detergent and distilled water. 90% ethanol was used to do final cleaning before being siliconized, treatment of 3-methacryloxypropyl-trimethoxysilan and filling gel.

| For 500 ml stock Acrylamide solution | |
|---|---|
| Acrylamide | 33.2 g |
| Bis-acrylamide | 1.75 g |
| Urea | 240 g |

Solution should be deionized by Amberlite MB-3 Monobed Resin(Sigma), 25 g for 500 ml solution.

| For 1 liter 10× sequencing buffer TBE | |
|---|---|
| Tris base | 160 g |
| Boric Acid | 38 g |
| Disodium EDTA | 9 g |

1x TBE buffer is the working condition mixing with 7% acrylamide/bis/urea solution.

15% Ammonium persulphate (0.20 ml) and TEMED (0.05 ml) were used to catalyze 60 ml. total volume of gel for polymerization.

12. Sequencing the colonies which have a sequence which hybridizes with the probes.

Three colonies are sequenced using the method of Sanger, F., et al., *PNAS*, 74, 5463–5467 (1977). S$^{35}$-dATP was used as labelling for exposure picture of the sequencing. Because the sizes of these colonies are different, ranging from 800 bp to 2.4 k BP, each reaction of sequencing only provided clear reading of 300 to 350 BP. In order to read the whole sequence of the DNA, a kit for the partial deletion DNA from Promega, the "Erase-a-Base™ System", was used to create different sizes of DNA for sequencing (Technical Manual, "Erase-a-Base™ System" Promega).

13. Sequencing 2.4 kb DNA of spider silk protein.

The partial sequencing results from the 2.4 kb DNA showed a repetitive sequence and high GC complex structure which can cause the fragments to delete and religate. In order to obtain correct sequence information, restriction enzyme Hae III was used to cut the 2.4 kb into small fragments varying from 150 to 900 bp and these Hae III fragments were separated by 1% low melting point agarose (Bethesda Research Laboratories) then purified by hot phenol, Maniatis, T., et al., *Molecular Cloning, A Lab Manual* (1982), and Elutip-d™. The pure fragments in different sizes were subcloned (same method as cloning) into pBluescript™ KS(+/−) plasmids and M13 phages mp 18 as well as mp 19 (from Strategene) respectively for sequencing.

14. Northern blotting and hybridization to determine the size of mRNA for silk proteins.

mRNA is purified by running whole RNA through the oligo-dT affinity column (same as above) and through a denaturing formaldehyde agarose gel, Frederick M. Ausubel, et al., *Current Protocols in Molecular Biology*, Volume 1, 4.9.5–4.9.8 (1987). The mRNA were blotted onto Zeta-probe membranes, Maniatis, T., et al., *Molecular Cloning, A Lab Manual* (1982). Hae III digested fragments were separated by agarose gel electrophoresis (same procedure as above). Nick translation kit (Nick Translation reagent Kit, Bethesda Research Laboratories) was used to make radioactive labeled probes using the 900 bp fragment as a template. Membrane with mRNA was hybridized at 75° C. by the probes to determine the size of mRNA of the silk proteins, Bio-Rad, Instruction Manual 4.3, Zeta-probe™ Blotting Membranes.

The DNA sequence and the corresponding amino acid sequence of the silk proteins are shown in FIG. 6.

EXAMPLE 4

A clone of spider silk DNA (2.0kb) (See FIG. 6) in pBluescript™SK+/−plasmids is selected. An insert is placed in the SmaI site. The pBluescript™SK+ vector is digested by SmaI restriction enzymes in the same manner as #6 in Example 3.

The insert is cut out from pBluescriptSK+ at the BamHI and EcoRI sites, ("NEB", New England Biolabs). The EcoRI site is filled in with a Klenow Fragment (Promega, Inc. supplied the fragment and protocol) to provide a blunt end at the EcoRI site. The BamHI overhang is left to insure proper orientation of the insert into the new vector pGEM™-3Z (Promega). The pGEM™ plasmid provides a multiple cloning site polylinker placed between a T7 promoter and a SP6 promoter to provide for convenient in vitro RNA synthesis from cloned DNA templates. This pGEM™-3Z vector is prepared by digesting with BamHI (BamHI digestion is carried out at 37° C. for 30 min. using the BRL reaction buffer (Bethesda Research Labs)) leaving an overhang and HincII (NEB) blunt end. The two plasmids are ligated using T-4 DNA ligase. T-4 DNA ligation is carried out at 4° C. overnight using 10x ligation buffer (Maniatis, T., et al., *Molecular Cloning, A Lab Manual* (1982)).

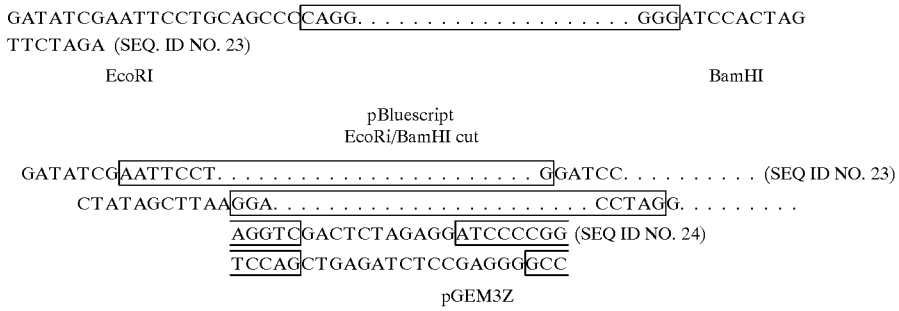

Transformation of the ligated DNA is performed by adding the DNA to previously made competent cells. After incubation of cells and DNA for 2 hours at 0° C., the cells and DNA are combined with 0.85% saline soft agar (3 ml of soft agar) and poured onto LB agar plates supplemented with 40 μg/ml X-gal, 50 μg/ml ampicillin and 40 μg/ml IPTG (isopropyl β-D-trisgalactopyranoside). X-gal (5-bromo-4-chloro-3-indolyl-β-D-galactopyranoside), ampicillin and IPTG are growth additives which are determined to be necessary for adequate growth of the transformants (Stratagene, BRL). The three host cell lines used are JM109 (Stratagene), DH5αF (Bethesda Research Laboratories), and SURE (Stratagene).

Expression of spider silk protein is induced by the addition of IPTG (Bethesda Research Laboratories (BRL)) in the growth media while culturing at 37° C. The extracted protein (50 μl) is examined by PAGE/SDS phastgel (Pharmacia). Since only a small amount of protein is produced, a reading frame shift in the plasmid is induced.

The reading frame shift is accomplished by digesting the plasmid with 1 Unit SphI (SphI digestion is carried out at 37° C. for 30 min. using the Promega SphI 10x buffer (Promega, Inc.)), then cutting off the 3' overhang of 4 bases with 1 Unit T-4DNA polymerase (Promega). 3' overhang is removed by adding 1 Unit T-4 DNA polymerase at room temperature for 10 mins. The bases removed are CGTA. Self-ligation occurs in a volume of 50 μl at 4° C. overnight. This plasmid is then self ligated with 1 Unit T-4 DNA ligase (New England Biolabs) to form plasmid pLM-4; and transformed as described above for the previous plasmids (Stratagene, BRL) into SURE™ E. coli host cells (Stratagene). SURE™ E. coli contain mutations which suppress homologous recombination, providing for stabilization of cloned DNA containing repeated sequences. The SURE™ E. coli transformed with plasmid pLM-4 was deposited at the American Type Culture Collection, 12301 Parklawn Drive, Rockville, Md., U.S.A. on Mar. 27, 1991 under the conditions of the Budapest Treaty and was assigned Deposit No. 68567.

Expression of 20–30 mg/l spider silk protein is induced by the addition of 40 μg/ml isopropylthiogalactoside (IPTG) (BRL) in the growth media. The protein is detected by PAGE/SDS (Pharmacia). This protein has the sequence as shown in FIG. 6.

The protein could be purified by centrifugation of the bacteria at 600×g for 15 min. and disruption of the bacteria by suspension in 1M acetic acid followed by centrifugation at 3000×g for 20 min. The pellet could be dissolved in 5% SDS(1:10 vol:vol) and the centrifugation repeated. The pellet is then treated with RNase and DNAase(0.01 mg/g) and the centrifugation repeated. The pellet is dissolved in 5M Li perchlorate and dialyzed against water(1:100 vol:vol) with 4 changes of water. The dialyzed suspension is centrifuged at 15,000×g for 30 min. The dissolving in Li perchlorate, dialysis and centrifugation is repeated 3 times.

EXAMPLE 5

10–20 mg of the protein silk from any of Examples 1, 2 or 4 (Predictive) are collected. The silk is dissolved to saturation in 5M Li SCN or Li perchlorate. The solution containing the dissolved silk is forced through a small gauge long needle (size 24 or smaller) and then into a 1M acetic acid solution. The fiber begins to form as it emerges from the needle.

EXAMPLE 6

Spider Silk Protein 2 was cloned as follows. From an existing Nephila clavipes major ampullate gland cDNA library, replicate nitrocellulose filters were produced. The colonies on the filters were fixed (Maniatis et al, Molecular Cloning, Cold Spring Harbor Laboratory (1982)) and hybridized with a kinased (Maniatis et al, Molecular Cloning, A Lab Manual, Cold Spring Harbor Laboratory (1982)) degenerate probe of 14 nucleotides named Ming 1 whose sequence, based on the pentapeptide G-Y-G-P-G (SEQ. ID NO. 14), is

CCNGGNCCATANCC. (SEQ. ID NO. 25).

Hybridization followed the procedures of Wood et al (PNAS USA, 82, 1585 (1985)) utilizing tetramethylammonium chloride. The filters were autoradiographed and the twelve darkest colonies were used to generate alkaline quick preparations that were digested with EcoRI and Bam HI. The gel was photographed after ethidium bromide staining and vacublotted to Zeta Probe™ Membrane (Biorad). Kinased Ming 1 was used as a probe to hybridize to the Southern blot. The clone containing the largest apparent insert, clone number six with approximately two kilobases, was used for all subsequent studies. An expression vector is constructed in the same manner as in Example 4 to form plasmid pMB-2.

The original Spider Silk 2 clone (p6B) was cut with BamH1 and Sac1 restriction endonucleases and subjected to Exonuclease III digestion for 30 sec. at 35° C. This DNA was treated with S1 nuclease and Klenow to produce a blunt ended DNA which was self-ligated (T4 DNA ligase) to form a pBluescript™SK+ plasmid with a Spider Silk 2 insert 173 bp shorter than the original clone (p6B). This plasmid, pMB-2, has a DNA sequence which starts at the Sac1 site of pBluescript and continues with nucleotide number 172 (the CCC) of sequence ID. NO. 3.

The E. coli SURE™ cells containing the plasmid (pMB-2) were deposited at the American Type Culture Collection 12301 Parklawn Drive, Rockville, Md., USA on Mar. 27, 1991 and was assigned Deposit No. 68568. Expression of a fusion protein (lac gene+spider silk protein) could be induced by addition of IPTG in the same manner as in Example 4. The protein could be purified in the same manner as in Example 4 and formed into a fiber in the same manner as in Example 5.

EXAMPLE 7 (PREDICTIVE EXAMPLE)

To facilitate high rate expression of spider major ampullate silk in bacteria, three expression vectors are used. All these are available from New England BioLabs with the precise instruction manual. The vectors have beta-lactamase gene for screening with ampicillin, and polylinker site for cloning constructed with a part of maltose binding protein (mal E) upstream of poly-liker site as well as an alpha subunit donor of beta-galactosidase downstream of poly-liker site. Transcription is conducted by tac promoter which is regulated by IPTG. The repressor gene of latose operon is also attached in all vectors, therefore high copy number of plasmid DNA may not dilute the repressors in cytosol of *E. coli* cells by providing competitive tac promoter region proportional to the number of plasmid DNA in a cell. The plasmid pLM4 which codes spider Silk Protein 1 is digested with EcoRI followed by purification on an agarose gel. The vector pMAL-cRI (NEB) is digested with EcoRI as well followed by CIP (calf intestinal alkaline phosphatase, Boehringer-Mannheim) treatment, then purified on an agarose gel. Two separated fragments are ligated with T4-ligase (Promega) in the presence of 5% PEG8000 (polyethyleneglycol 8000, Sigma) for one hour at 37° C. Ligate is transformed to SURE™ competent cells (Stratagene) according to the instruction manual, then pored onto LB plate containing ampicillin, X-gal and IPTG. Proper oriented clones are screened by either restriction enzyme digestion or DNA sequencing. The plasmid pMH2 which codes Silk Protein 2 is digested with both BamHI and XbaI to excise out the cDNA followed by filling 5'-end overhangs with Klenow fragment of *E. coli* polymerase I (USB), then purified on an agarose gel as above. Expression vector, pMAL-c or pMAL-p, is digested with StuI to produce the blunt ends followed by CIP treatment and purification on an agarose gel as well. Two purified fragments are ligated with T4-ligase, and transformed in SURE competent cells. Either restriction enzyme digestion or DNA sequencing is carried out to determine the orientation of the insert. *E. coli* cells containing either pMAL-cRI or pMAL-c vector produce spider silk in cytosol, while *E. coli* cells containing pMAL-p vector excrete spider silk in peri-plasma. The former product is purified in the same manner as in Example 4, but the latter product is recovered by treating cells simply with lysozyme at the concentration of 0.1 mg/ml on ice for 30 min followed by centrifugation to recover supernatant. Recovered protein is a fused protein with a part of maltose binding protein. Using a part of maltose binding protein, with an affinity column which is provided from NEB with the vectors, fused protein is purified. The excess maltose binding protein is removed by digesting the fused protein with the factor Xa which recognizes and cut between the maltose binding protein and spider silk. Factor Xa is provided from NEB as well.

All publications, including U.S. Patents, referred to in this application are herein incorporated by reference.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What we claim is:

1. An isolated DNA which codes for a protein comprising the amino acid sequence described in SEQ. ID. NO. 2.

2. An isolated DNA which codes for a protein comprising the amino acid sequence described in SEQ. ID. NO. 4.

3. An isolated DNA which encodes a protein comprising repeating units having amino acid sequences selected from the group consisting of SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, and SEQ ID NO:37, and mixtures thereof.

4. An isolated DNA molecule encoding a protein which comprises nucleotides encoding repeat units having the amino acid sequence Ala-Gly-Arg-Gly-Gly-Xaa-Gly-Gly-Zaa-Gly-Ala-Gly- (Ala)$_m$-Gly-Gly-Ala-Gly-Glu-Gly-Gly-Baa-Gly-Gly-Leu-Gly-Gly-Glu-Gly (SEO ID NO:7), wherein m is 6 or 7 and wherein Xaa, Zaa and Baa are leucine, tyrosine or glutamine and Xaa is not the same amino acid as Zaa.

5. An isolated DNA which encodes a protein comprising repeating units having amino acid sequences selected from the group consisting of SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:50, SEQ ID NO:51, SEQ ID NO:52, SEQ ID NO:53, SEQ ID NO:55, SEQ ID NO:56, SEQ ID NO:58, SEQ ID NO:59, SEQ ID NO:60, SEQ ID NO:61, and SEQ ID NO:62, and mixtures thereof.

6. An isolated cDNA which codes for a protein comprising repeating units wherein said repeating units are comprised of a sequence represented by the formula $$[(A)_m(X)_n]_p$$

wherein m is an integer of 4 to 10, n is an integer of 10 to 20, p is an integer of 1 to 100 and each X, which may be the same or different, is selected from the group consisting of P, G, A, Q, Y and L, wherein at least 50% of the X's are G.

7. The cDNA of claim 6, wherein p is 15 to 50.

8. The cDNA of claim 6, wherein p is 25 to 100.

9. An isolated cDNA according to claim 6, wherein m is 4 to 10, n is 10 to 20, and p is an integer of 1 to 100 and each X, which may be the same or different, is selected from the group consisting of G, A, Q, Y and L, wherein at least 50% of the X's are G.

10. The cDNA of claim 9, wherein p is 15 to 50.

11. The cDNA of claim 9, wherein p is 25 to 100.

12. A replicable vector containing the DNA of claim 1,2,3,4,5,6 or 9.

13. A host cell comprising the vector of claim 12.

14. A replicable vector according to claim 12, wherein said protein is one having a molecular weight from 100,000 to 300,000 daltons.

15. An isolated DNA molecule according to claim 4, wherein Xaa is glutamine.

16. An isolated DNA molecule according to claim 4, wherein the repeat units are separated by varying numbers of alanine or serine residues.

17. An *Escherichia coli* host cell comprising a plasmid comprising the cDNA of claim 8.

18. An *Escherichia coli* host cell comprising a plasmid comprising the cDNA of claim 9.

19. A plasmid pLM-4 which is contained in ATCC Deposit No. 68567.

20. A plasmid pMB-2 which is contained in ATCC Deposit No. 68568.

* * * * *